(12) United States Patent
Xu et al.

(10) Patent No.: US 11,375,895 B2
(45) Date of Patent: Jul. 5, 2022

(54) THREE-DIMENSIONAL INTEGRATED STRETCHABLE ELECTRONICS

(71) Applicant: THE REGENTS OF THE UNIVERSITY OF CALIFORNIA, Oakland, CA (US)

(72) Inventors: Sheng Xu, La Jolla, CA (US); Yang Li, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 455 days.

(21) Appl. No.: 16/500,507

(22) PCT Filed: Apr. 3, 2018

(86) PCT No.: PCT/US2018/025956
§ 371 (c)(1),
(2) Date: Oct. 3, 2019

(87) PCT Pub. No.: WO2018/187376
PCT Pub. Date: Oct. 11, 2018

(65) Prior Publication Data
US 2020/0085299 A1     Mar. 19, 2020

Related U.S. Application Data

(60) Provisional application No. 62/480,858, filed on Apr. 3, 2017, provisional application No. 62/576,807, filed on Oct. 25, 2017.

(51) Int. Cl.
*A61B 5/00*     (2006.01)
*A61B 5/296*    (2021.01)
(Continued)

(52) U.S. Cl.
CPC ............ *A61B 5/0002* (2013.01); *A61B 5/296* (2021.01); *H01L 21/486* (2013.01); *H01L 21/56* (2013.01);
(Continued)

(58) Field of Classification Search
CPC .................. A61B 5/0002; A61B 5/296; A61B 2562/0219; A61B 2562/0261;
(Continued)

(56) References Cited

U.S. PATENT DOCUMENTS 4,743,710 A    5/1988  Shieber
8,666,471 B2*  3/2014  Rogers ................ A61B 5/6867
                                                    607/116
(Continued)

FOREIGN PATENT DOCUMENTS

CN    102206417    10/2011

*Primary Examiner* — Carl J Arbes
(74) *Attorney, Agent, or Firm* — Stuart H. Mayer; Mayer & Williams PC

(57) ABSTRACT

A method of fabricating a stretchable and flexible electronic device includes forming each of the functional layers is by: (i) forming on an elastomer substrate a conductive interconnect pattern having islands interconnected by bridges; (ii) applying a conductive paste to the islands; (iii) positioning at least one functional electronic component on each island; and (iv) applying heat to cause the conductive paste to reflow. An elastomer encapsulant is formed over the functional electronic components and the conductive interconnect pattern on each of the functional layers. The elastomer encapsulant has a Young's modulus equal to or less than that of the substrate. The encapsulant includes a pigment to increase absorption of laser light. At least one via is laser ablated, which provides electrical connection to any two (Continued)

functional layers. The via is filled with solder paste to create a bond and electrical connection between the functional layers.

20 Claims, 50 Drawing Sheets

(51) Int. Cl.
*H05K 3/28* (2006.01)
*H01L 21/48* (2006.01)
*H01L 23/538* (2006.01)
*H01L 25/16* (2006.01)
*H01L 23/00* (2006.01)
*H01L 21/56* (2006.01)
*H01L 21/60* (2006.01)

(52) U.S. Cl.
CPC ...... *H01L 23/5384* (2013.01); *H01L 23/5385* (2013.01); *H01L 23/5386* (2013.01); *H01L 24/03* (2013.01); *H01L 24/81* (2013.01); *H01L 25/162* (2013.01); *H05K 3/284* (2013.01); *A61B 2562/0219* (2013.01); *A61B 2562/0261* (2013.01); *A61B 2562/0271* (2013.01); *A61B 2562/12* (2013.01); *A61B 2562/164* (2013.01); *H01L 2021/6024* (2013.01); *H01L 2224/03003* (2013.01); *H01L 2224/0311* (2013.01); *H01L 2224/0569* (2013.01); *H01L 2224/05551* (2013.01); *H01L 2224/05555* (2013.01); *H01L 2224/05582* (2013.01); *H01L 2224/05647* (2013.01); *H01L 2224/1132* (2013.01); *H01L 2224/81192* (2013.01); *H01L 2224/81815* (2013.01)

(58) Field of Classification Search
CPC ........ A61B 2562/0271; A61B 2562/12; A61B 2562/164; H05K 3/284; H01L 21/486; H01L 21/56; H01L 23/5384; H01L 23/5385; H01L 23/5386; H01L 24/81; H01L 25/162; H01L 2021/6024; H01L 2224/03003; H01L 2224/0311; H01L 2224/05551; H01L 2224/05582; H01L 2224/05547; H01L 2224/0569; H01L 2224/1132; H01L 2224/81192; H01L 2224/81815
See application file for complete search history.

(56) References Cited

U.S. PATENT DOCUMENTS

| | | |
|---|---|---|
| 2002/0160296 A1 | 10/2002 | Wolk |
| 2010/0002402 A1* | 1/2010 | Rogers .................. H05K 1/028 361/749 |
| 2011/0244208 A1 | 10/2011 | Saka |
| 2012/0165759 A1 | 6/2012 | Rogers |
| 2013/0041235 A1 | 2/2013 | Rogers |
| 2013/0333094 A1 | 12/2013 | Rogers et al. |
| 2014/0303452 A1 | 10/2014 | Ghaffari |
| 2017/0094774 A1 | 3/2017 | Adel et al. |
| 2017/0341347 A1 | 11/2017 | Nakamura |

\* cited by examiner

Figure 1B
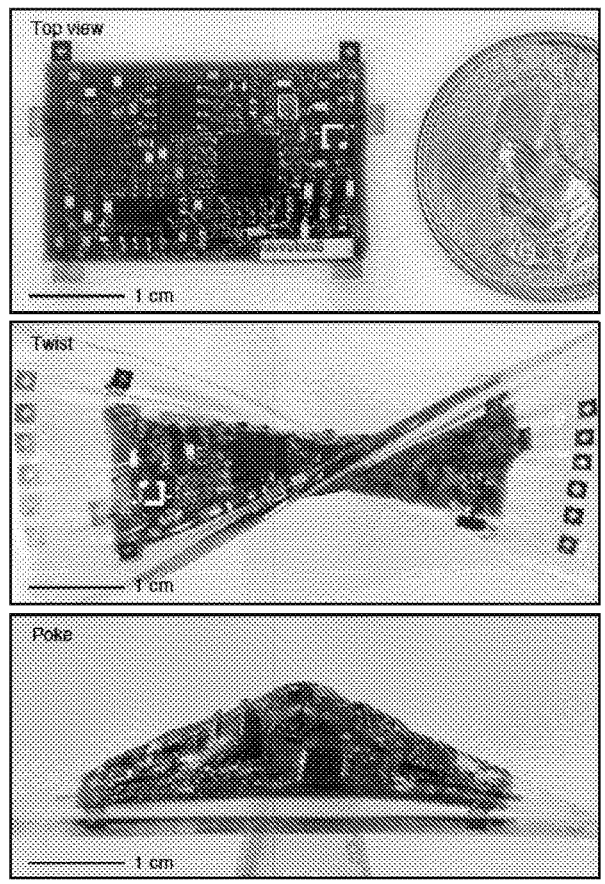
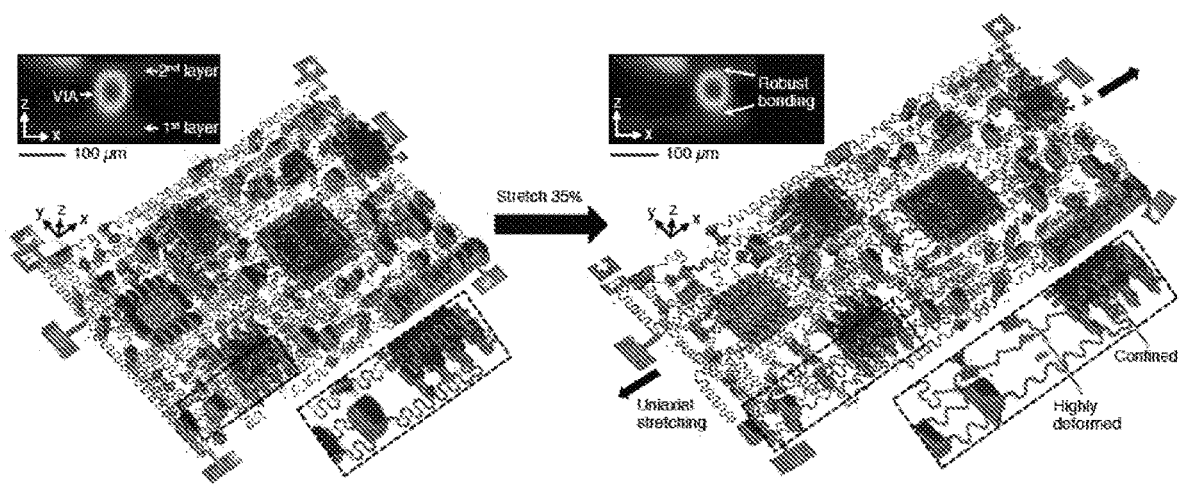
Figure 1C

Figure 2C
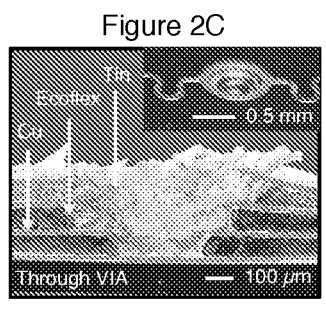
Figure 2D
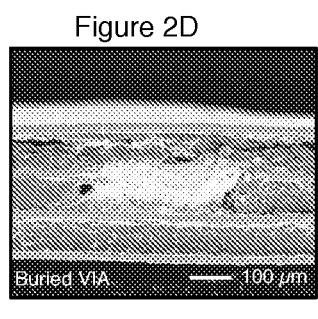
Figure 2E
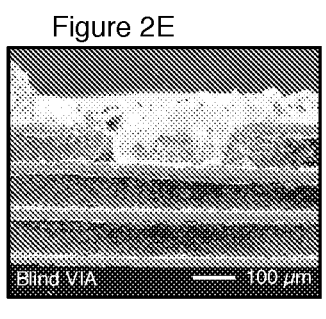
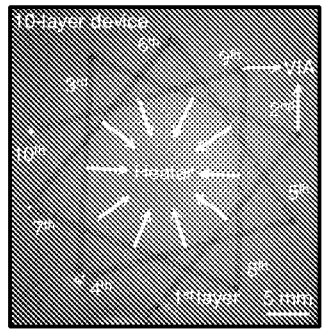
Figure 2F
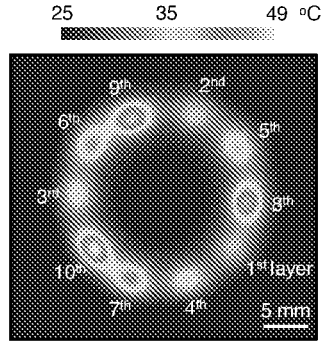
Figure 2G
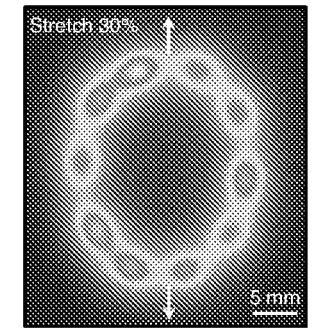
Figure 2H

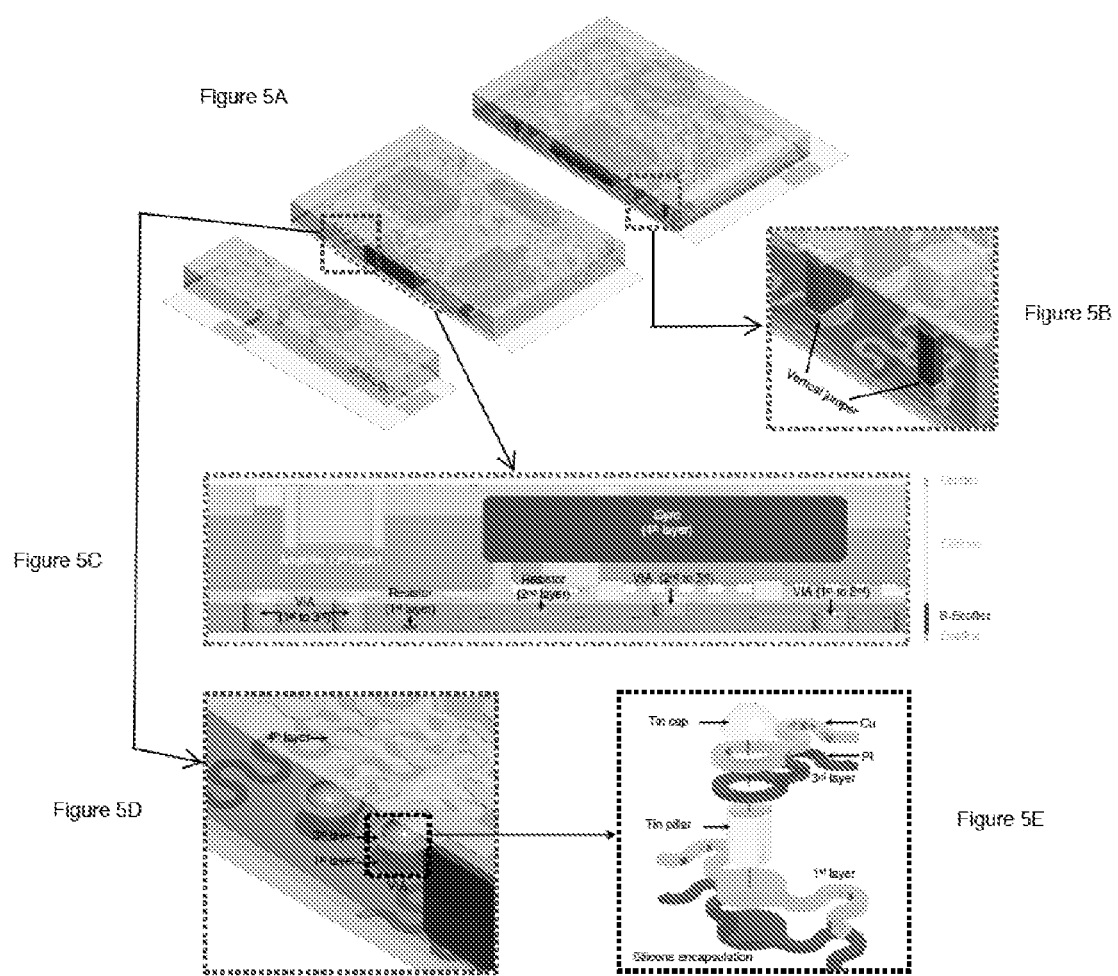

Figure 10A
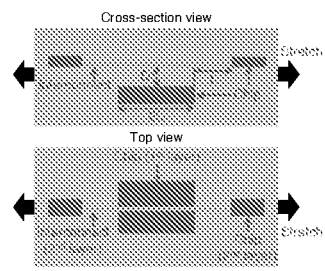
Figure 10C
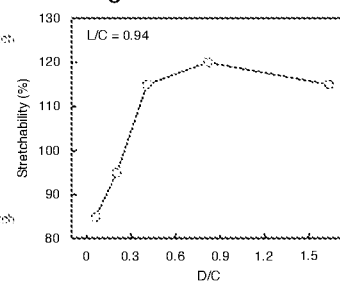
Figure 10E
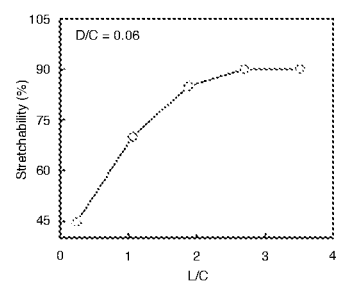
Figure 10B    L/C = 1.06; D/C = 0.06;
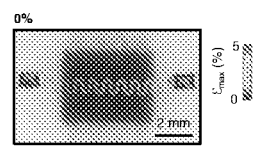
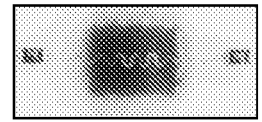
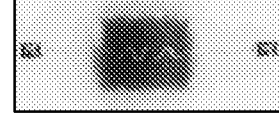
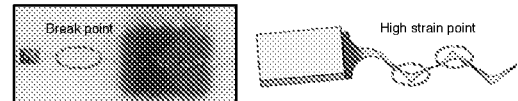
Figure 10D    L/C = 1.88;
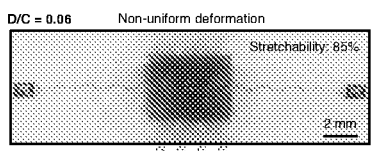
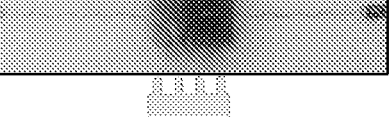
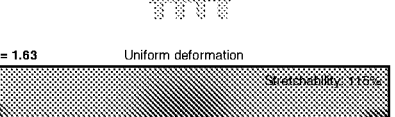

Figure 12A
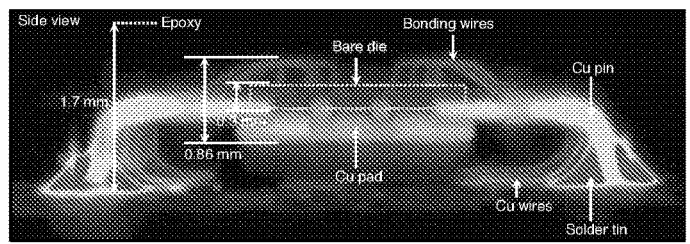
Figure 12B
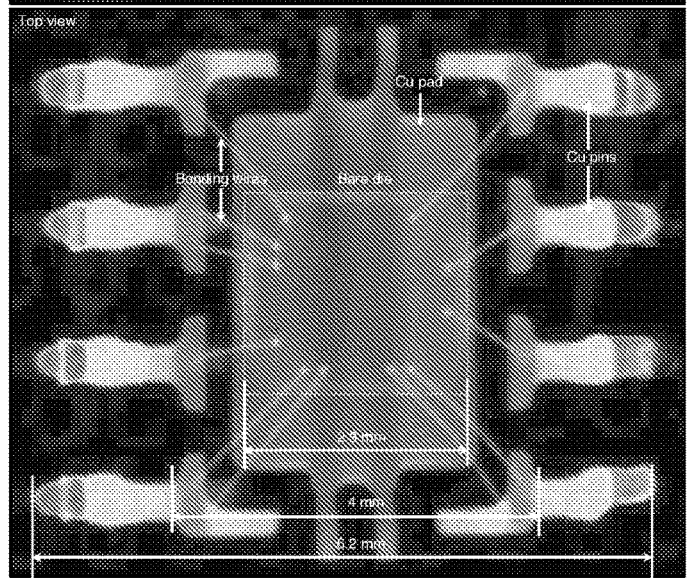
Figure 12C
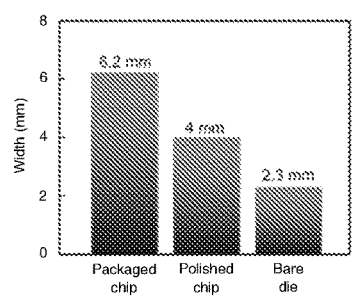
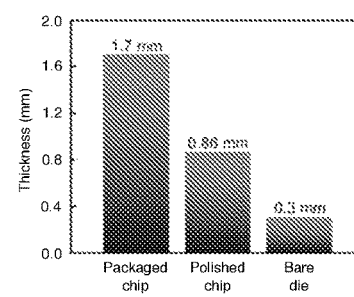
Figure 12D

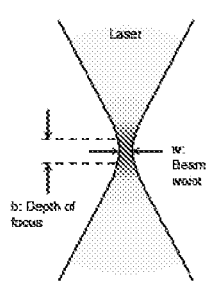
Figure 13A
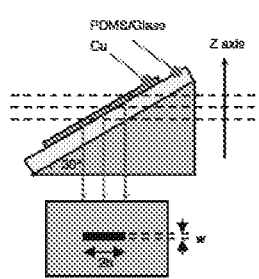
Figure 13B
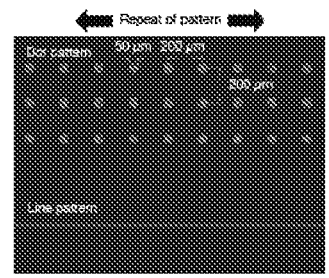
Figure 13C
Figure 13D
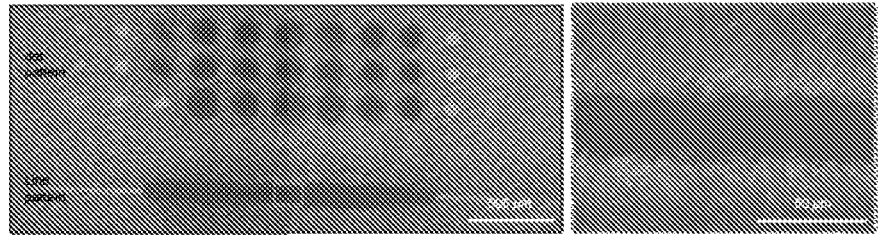
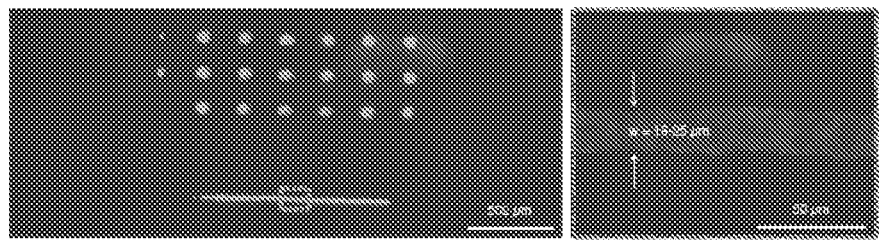

Etching pattern design

Etching results

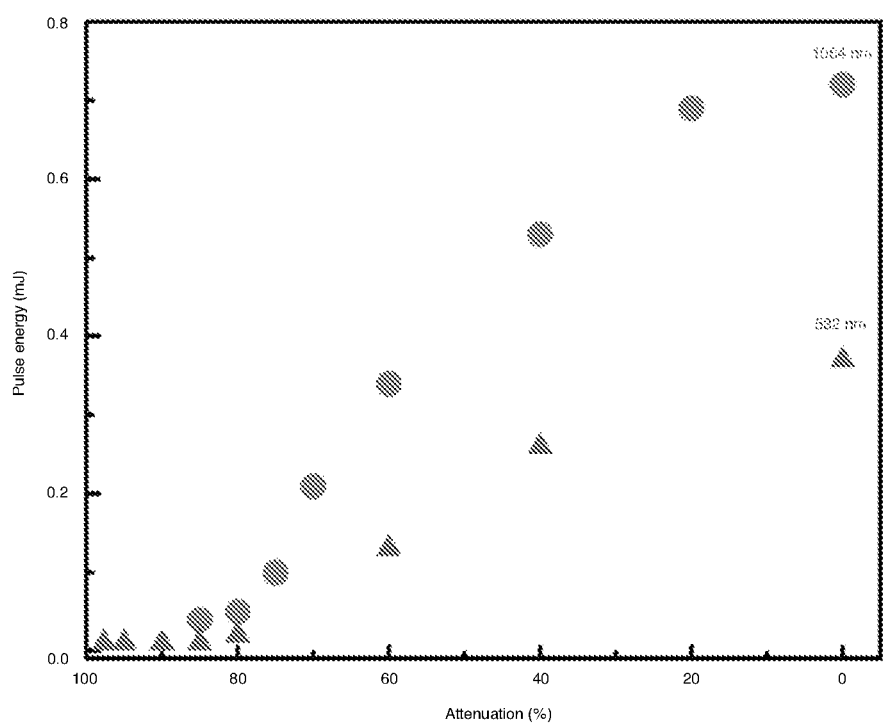

Figure 18A

| Green Laser 532 nm | | | | | | Critical attenuation for etching Cu | | | | | Laser condition: 50 cycles |
|---|---|---|---|---|---|---|---|---|---|---|---|
| Attenuation | 97.5% | 95% | 90% | 85% | 80% | 75% | 70% | 60% | 40% | 20% | 0% |
| Cu | | | | | | | | | | | |
| Polyimide | | | | | | | | | | | |
| Black Ecoflex | | | | | | | | | | | |
| Green Ecoflex | | | Critical attenuation for etching the other materials | | | | | | | | |
| Yellow Ecoflex | | | | | | | | | | | |
| Trans. Ecoflex | | | | | | | | | | | |

Figure 18B

| IR Laser 1064 nm | | | | | | | Critical attenuation for etching Cu | | | | Laser condition: 50 cycles |
|---|---|---|---|---|---|---|---|---|---|---|---|
| Attenuation | 97.5% | 95% | 90% | 85% | 80% | 75% | 70% | 60% | 40% | 20% | 0% |
| Cu | | | | | | | | | | | |
| Polyimide | | | | | | | | | | | |
| Black Ecoflex | | | | | | | | | | | |
| Green Ecoflex | | | | | | Critical attenuation for etching the other materials | | | | | |
| Yellow Ecoflex | | | | | | | | | | | |
| Trans. Ecoflex | | | | | | | | | | | |

Figure 27A 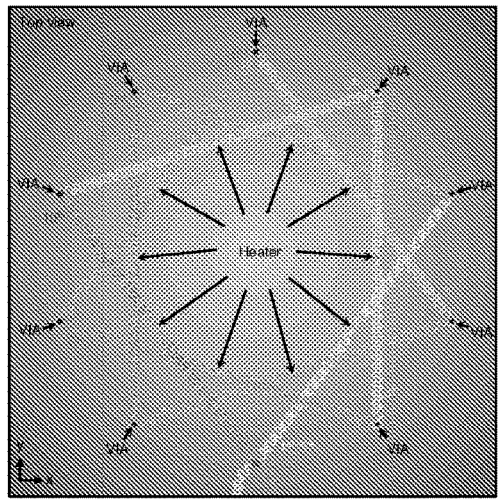 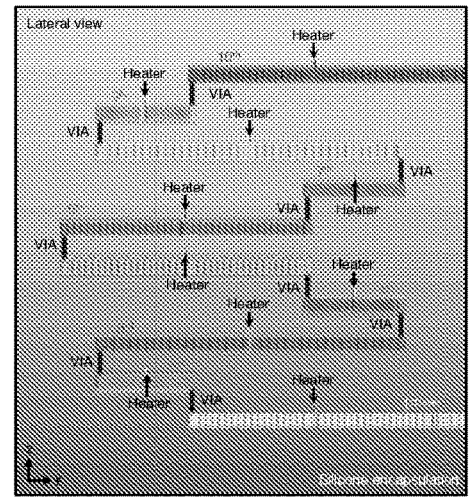
Figure 27B 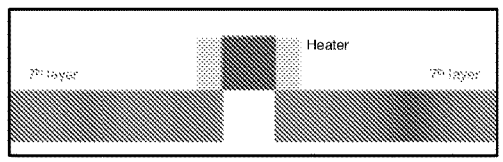 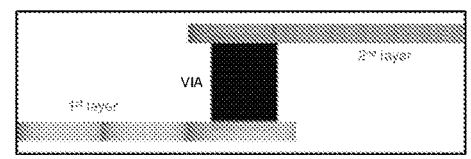
Figure 27C 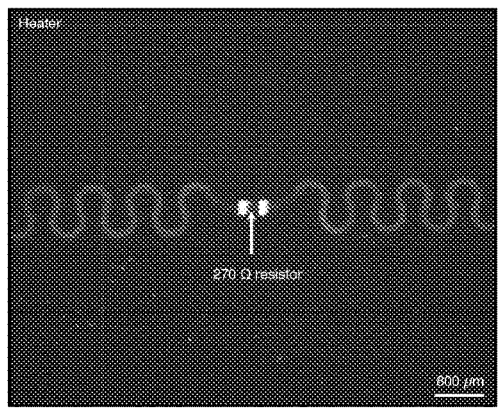 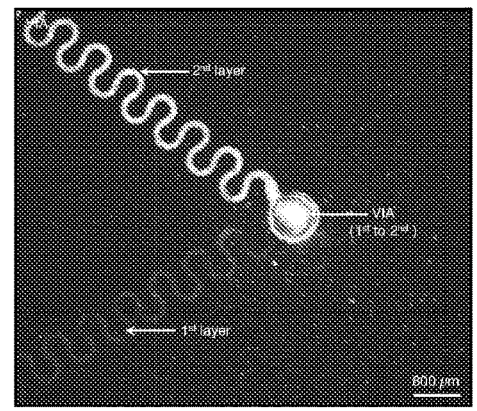

Figure 28A
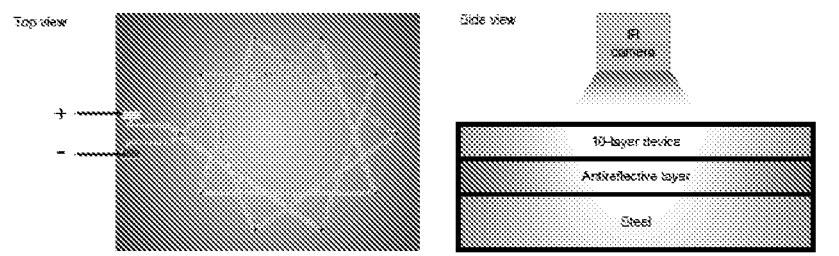
Figure 28B
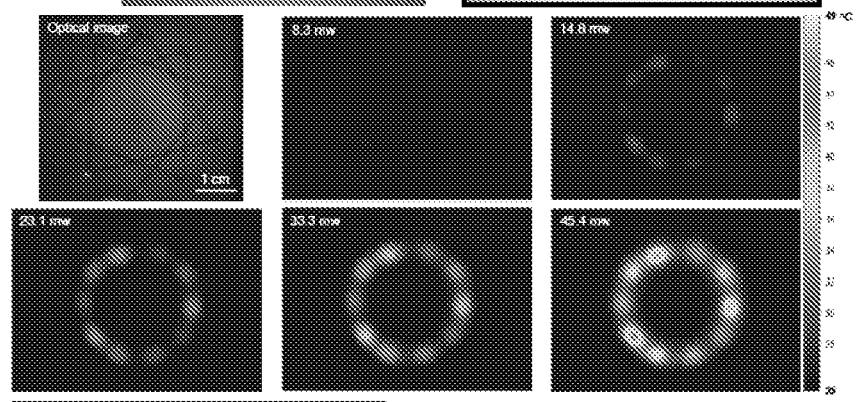
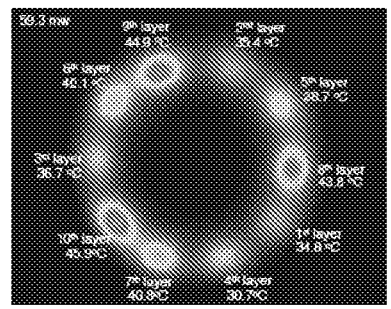 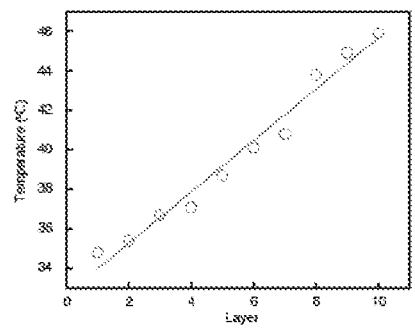
Figure 28C

Layer by layer fabrication

Alignment marker

| | CAD design | Top view | Tilted view |

Hardware: iPhone 6 Plus; Software: NRF Connect

Figure 38
Strain sensor circuit diagram
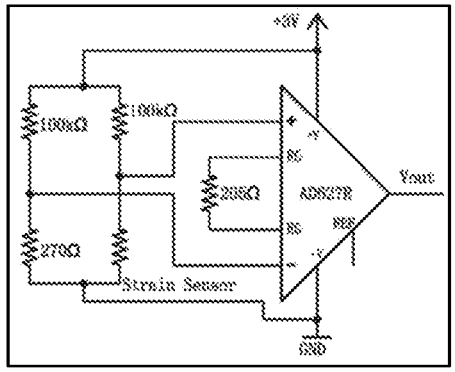
Epidermal potential circuit diagram
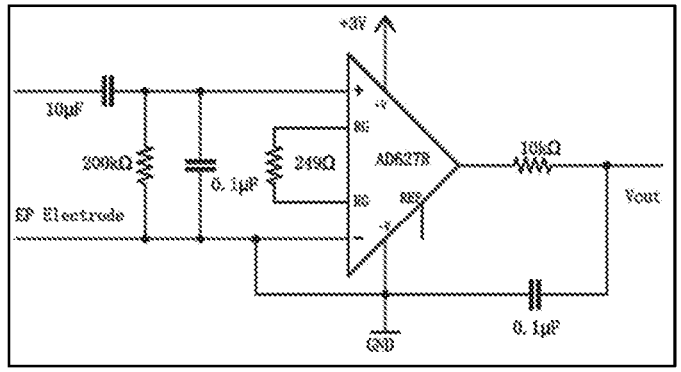
Bluetooth circuit diagram
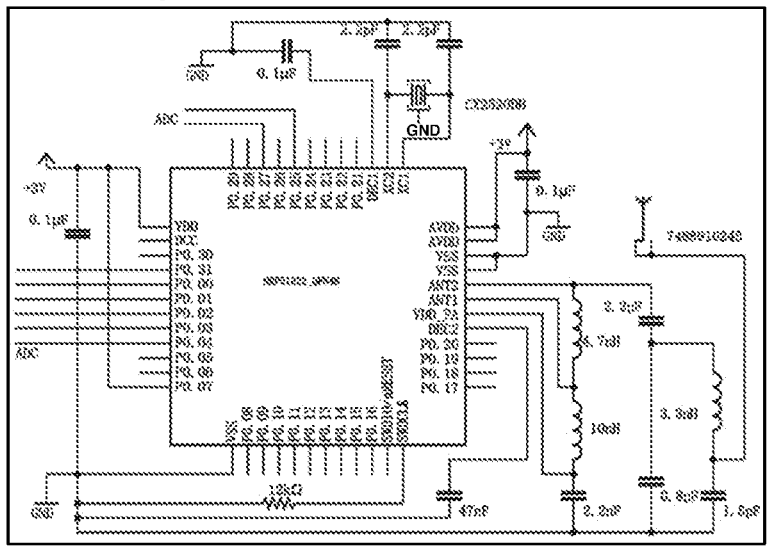
Temperature sensor circuit diagram
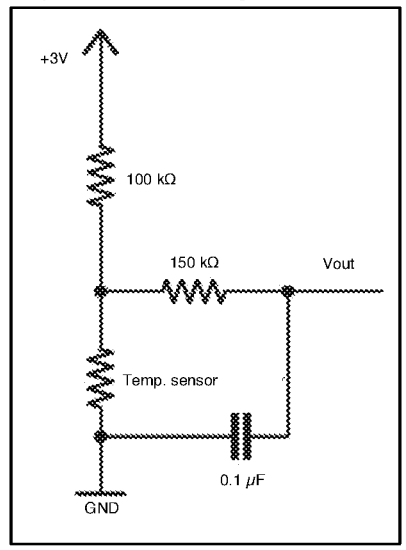
Gyroscope circuit diagram
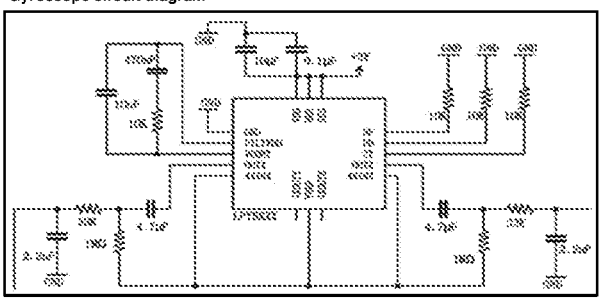
Accelerometer circuit diagram
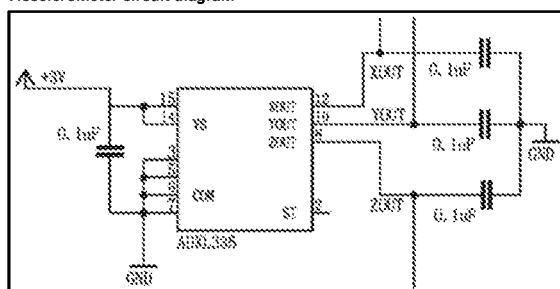

Figure 40

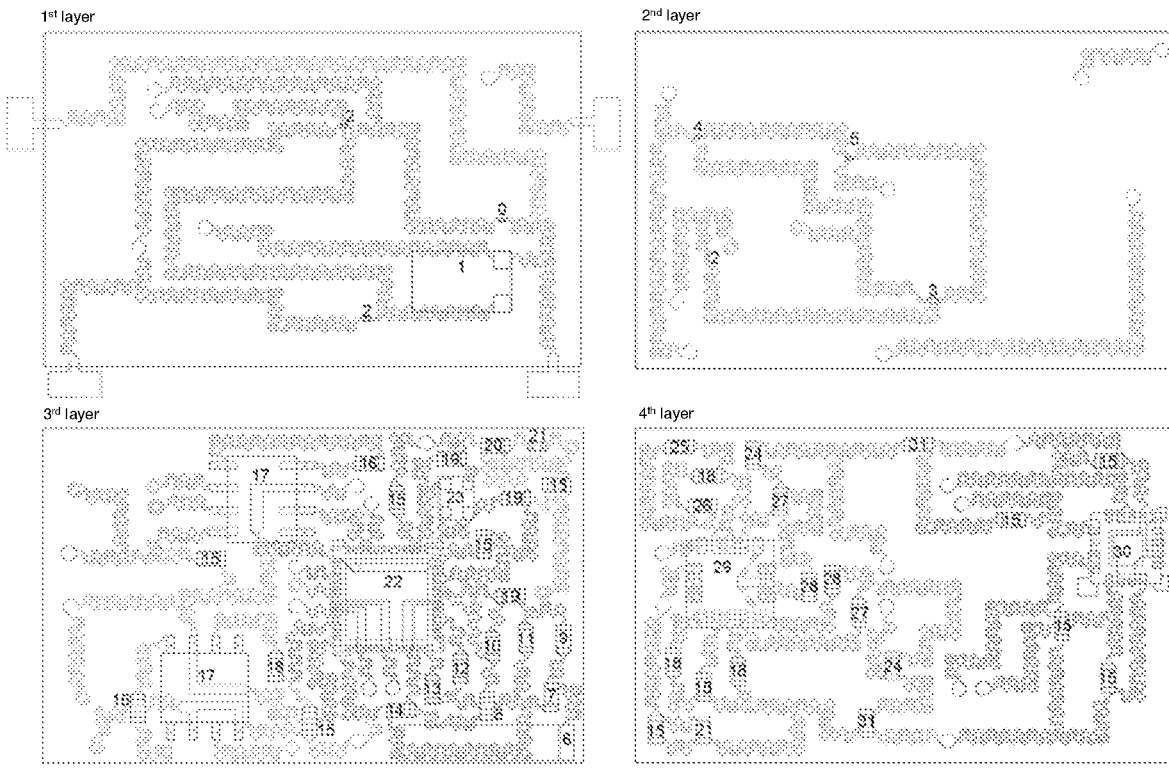

| Device Number | Type | Value | Manufacturer Part Number | Device Number | Type | Value | Manufacturer Part Number |
|---|---|---|---|---|---|---|---|
| 0 | Resistor | 270 Ohm | ERJ-XGNJ271Y | 16 | Resistor | 249 Ohm | CR0603-FX-2490ELF |
| 1 | Strain sensor | N/A | BF350-3AA | 17 | Amplifier | N/A | AD627BRZ-R7 |
| 2 | Resistor | 100K Ohm | RC0402F104CS | 18 | Resistor | 10K Ohm | CR0603-FX-1002HLF |
| 3 | Thermistor | N/A | NCP03WF104F05RL | 19 | Capacitor | 2.2 pF | C0603C229C5GACTU |
| 4 | Capacitor | 0.1 µF | CL02A104KQ2NNNC | 20 | Resistor | 200K Ohm | CR0603-JW-204ELF |
| 5 | Resistor | 150K Ohm | ERJ-XGNJ154Y | 21 | Capacitor | 10 µF | GRM155C80J106ME11D |
| 6 | Antenna | N/A | 7488910245 | 22 | Bluetooth | N/A | NRF51822-QFAC-T |
| 7 | Capacitor | 1.5 pF | CL10C1R5BB8NNNC | 23 | Crystal | N/A | CX2520DB16000D0GPSC1 |
| 8 | Inductor | 10 nH | L-14C10NJ4T | 24 | Resistor | 33K Ohm | CR0603-FX-3302ELF |
| 9 | Inductor | 3.3 nH | L-14C3N3SV4T | 25 | Capacitor | 10 nF | GRM188R71H103KA01D |
| 10 | Inductor | 4.7 nH | L-14C4N7SV4T | 26 | Capacitor | 470 nF | C1608X7R1C474K080AC |
| 11 | Capacitor | 0.8 pF | CL10C0R8BB8NNNC | 27 | Capacitor | 4.7 µF | CL10B475KQ8NQNC |
| 12 | Capacitor | 47 nF | C0603C473K1RACTU | 28 | Resistor | 1M Ohm | CR0603-JW-105ELF |
| 13 | Resistor | 12K Ohm | CR0603-JW-123ELF | 29 | Gyro | N/A | LPR503ALTR |
| 14 | Capacitor | 2.2 nF | GRM1885C1H222JA01D | 30 | Accelerometer | N/A | ADXL335BCPZ |
| 15 | Capacitor | 0.1 µF | GRM188R71C104KA01D | 31 | Capacitor | 2.2 µF | GRM188R61C225KE15D |

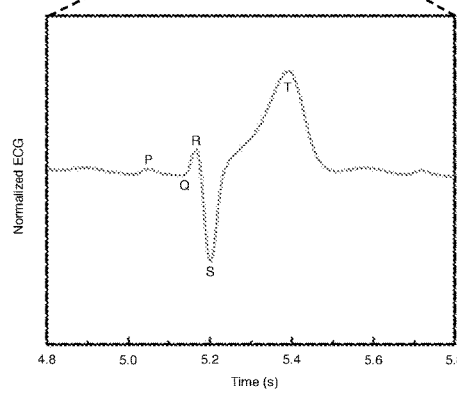
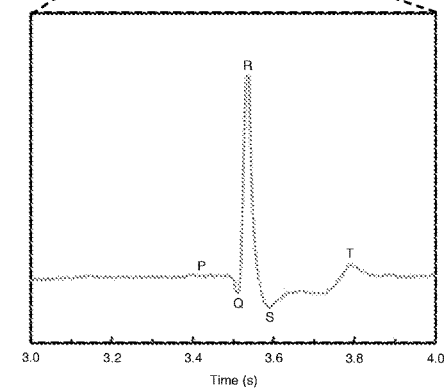

Figure 43A
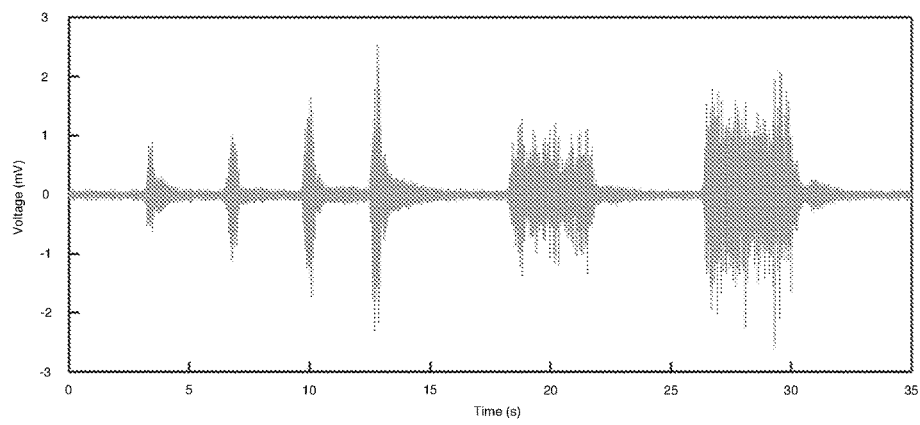
Figure 43B
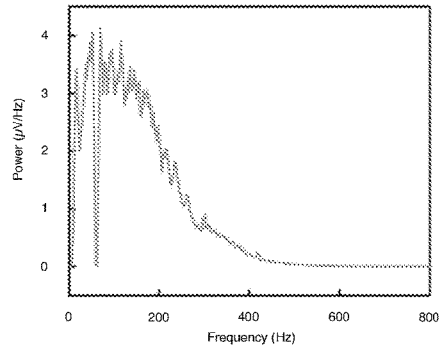
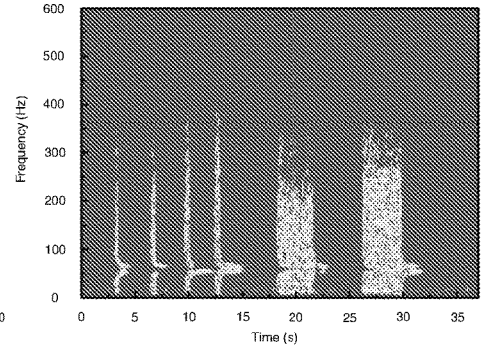
Figure 43C

Figure 47A
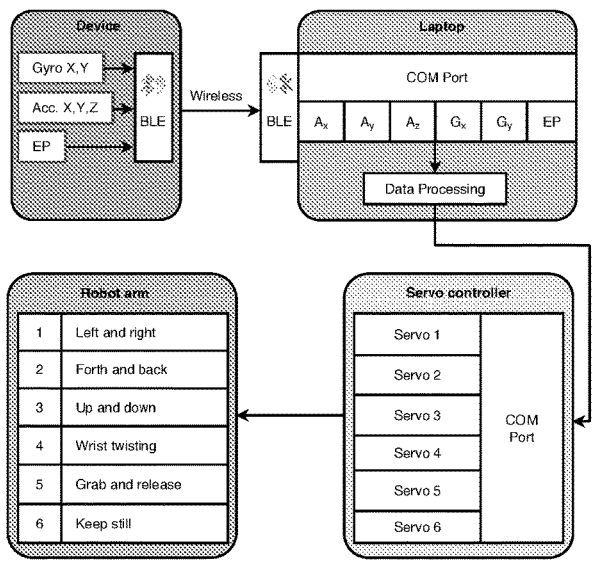
Figure 47B
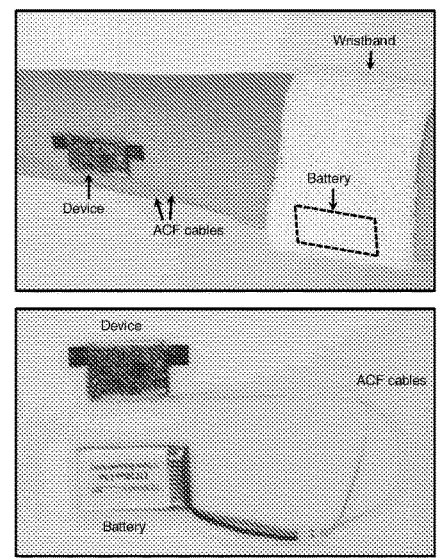
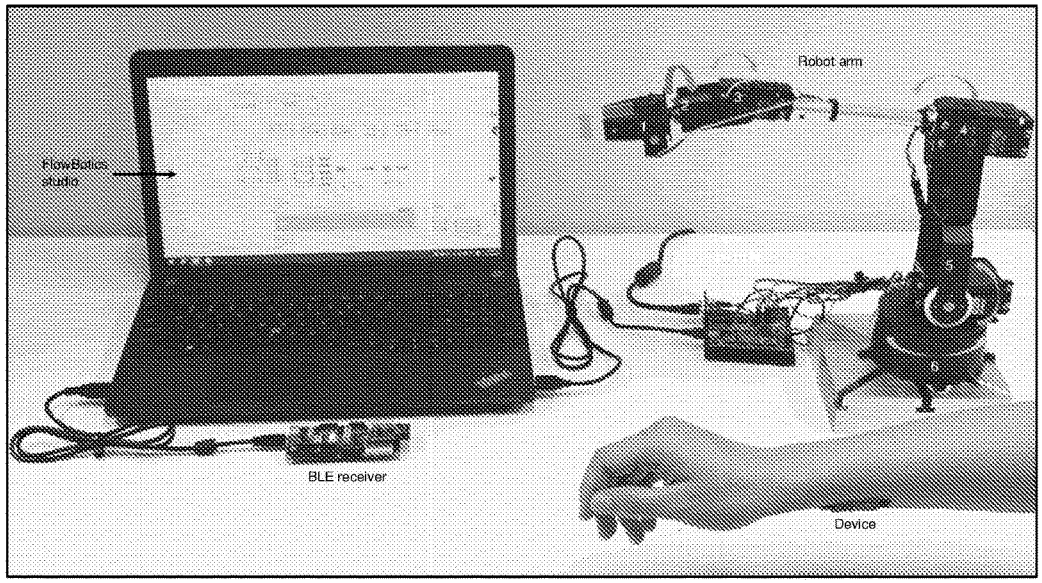
Figure 47C

THREE-DIMENSIONAL INTEGRATED STRETCHABLE ELECTRONICS

CROSS-REFERENCE TO RELATED APPLICATIONS

This application is a National Phase of PCT/US2018/025956, filed Apr. 3, 2018, which claims benefit of priority to U.S. Provisional Patent Application Ser. No. 62/480,858, filed Apr. 3, 2017 and U.S. Provisional Patent Application Ser. No. 62/576,807, filed Oct. 25, 2017, owned by the assignee of the present application and herein incorporated by reference in its entirety.

BACKGROUND

Stretchable electronics attract wide research interests due to its potential applications in fields such as healthcare, consumer electronics, and human-machine interface. These devices currently exist, however, only in large area, low-density single layer formats, which cannot meet the growing demands for higher levels of integration and functional complexity. Incorporating commercial-off-the-shelf (COTS) components on the stretchable substrates represents a leap forward by building on the strength of decades of integrated circuit developments. Nevertheless, the surface density of functional components in a single layer will reach a bottleneck because of mechanical design constraints. Physical stacking of two layers of stretchable circuits has been proposed, which doubles the area density of functional components. However, with electrical isolation between layers, the growth of function density will only be linear. A major challenge is in the formation of interlayer electrical connectivity.

SUMMARY

Described herein is a three-dimensional (3D) integrated stretchable and flexible system with interlayer electrical connectivity that has a design which exponential growth of function density. The engineering framework for this system enables not only higher integration levels but also new functions that are challenging for single-layer designs. In one aspect, the stretchable electronics is built layer by layer by transfer printing pre-designed stretchable circuits on each layer of elastomer. Vertical interconnect accesses (VIAs) that are formed by laser ablation and controlled soldering allow the connection density to accommodate state-of-the-art circuit components.

In another aspect, a method of fabricating a stretchable and flexible electronic device is presented. In accordance with the method, at least three functional layers are formed. Each of the functional layers is formed by: (i) forming a conductive interconnect pattern on an elastomer substrate, the conductive interconnect structure including islands interconnected by bridges; (ii) applying a conductive paste to the islands; (iii) positioning at least one functional electronic component on each of the islands; and (iv) applying heat to cause the conductive paste to reflow. An elastomer encapsulant is formed over the functional electronic components and the conductive interconnect pattern on each of the functional layers. The elastomer encapsulant has a Young's modulus equal to or less than a Young's modulus of the elastomer substrate. The elastomer encapsulant includes a colored pigment that increases absorption of a selected laser wavelength by the elastomer encapsulant. At least one via is laser ablated. The via provides electrical connection to any two layers in the three functional layers using laser light at the selected laser wavelength. The at least one via is filled with solder paste and heat is applied to cause the conductive paste to reflow, thereby establishing a bond and an electrical connection between the functional layers.

In one example the formation of the elastomer encapsulant includes spin coating the elastomer encapsulant over the functional electronic components and the conductive interconnect pattern on each of the functional layers.

In one example the conductive interconnect pattern is defined by laser ablating a predefined pattern in a bilayer that includes a metal layer and a polymide layer disposed on a substrate and the conductive interconnect pattern is transferred to the functional layer using a water-soluble tape.

In one example filling the at least one via with solder paste includes dispensing solder paste into the at least one via by screen printing or dropping casting.

In one example establishing an electrical connection between two of the functional layers is accomplished by vertically arranging a zero-resistance jumper between the two functional layers.

In one example the bridges interconnecting the islands in the conductive interconnect pattern have a serpentine configuration.

In one example the functional electronic components are selected from the group consisting of sensors, active electronic components, and passive electronic components.

In one example the active electronic components are selected from the group consisting of amplifiers and RF components.

In one example the passive electronic components are selected from the group consisting of resistors, capacitors, and inductors.

In one example at least one of the functional electronic components includes a multichannel sensing system having a wireless communication circuit.

In one example at least one of the functional electronic components includes an accelerometer and at least another of the functional electronic components includes a gyroscope.

In one example at least another of the functional electronic components includes a strain sensor.

In one example at least another of the functional electronic components includes a temperature sensor.

In one example at least another of the functional electronic components includes a local field potential sensor.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. These and various other features will be apparent from a reading of the following Detailed Description and a review of the associated drawings.

BRIEF DESCRIPTION OF THE DRAWINGS

FIGS. 1A-1C show one example of a stretchable and flexible electronic device having multiple functional layers that each include one or more functional electronic elements.

FIGS. 2A-2H illustrate aspects of the fabrication of the vias and a 10-layer decagram stretchable heater.

FIGS. 5A-5E is a schematic illustration of one example of the three-dimensional integrated stretchable and flexible system.

FIGS. 10A-10E show experimental and finite element analysis (FEA) studies of the mechanical coupling between layers of the multilayered device.

FIGS. 12A-12B show XCT images of a typical functional chip (i.e., the amplifier) and summarized dimensions of the packaged chip, polished chip, and bare die and FIGS. 12C-12D show summarized width and thickness data of the chip.

FIGS. 13A-13D show an evaluation of the effective laser beam size and depth of focus.

FIG. 17 shows the laser pulse energy controlled by the lens attenuation system.

FIGS. 18A-18B show the ablation of different materials with different laser wavelengths.

FIGS. 27A-27C illustrate the 10-layer stretchable decagram device structure.

FIG. 28A illustrates the thermal imaging setup for the 10-layer stretchable decagram device, FIG. 28B shows thermal images of the device with different heating power and FIG. 28C is a temperature summary of heaters in different layers.

FIG. 38 is a summary of the circuit design for the multilayered stretchable system.

FIG. 40 summaries the chips used in the multilayered stretchable system.

FIGS. 43A-43C show EMG signals acquired from the forearm to show the signal frequency spectrum.

FIGS. 47A-47C show a robotic arm controlling system.

DETAILED DESCRIPTION

Overview

Figure 1A:
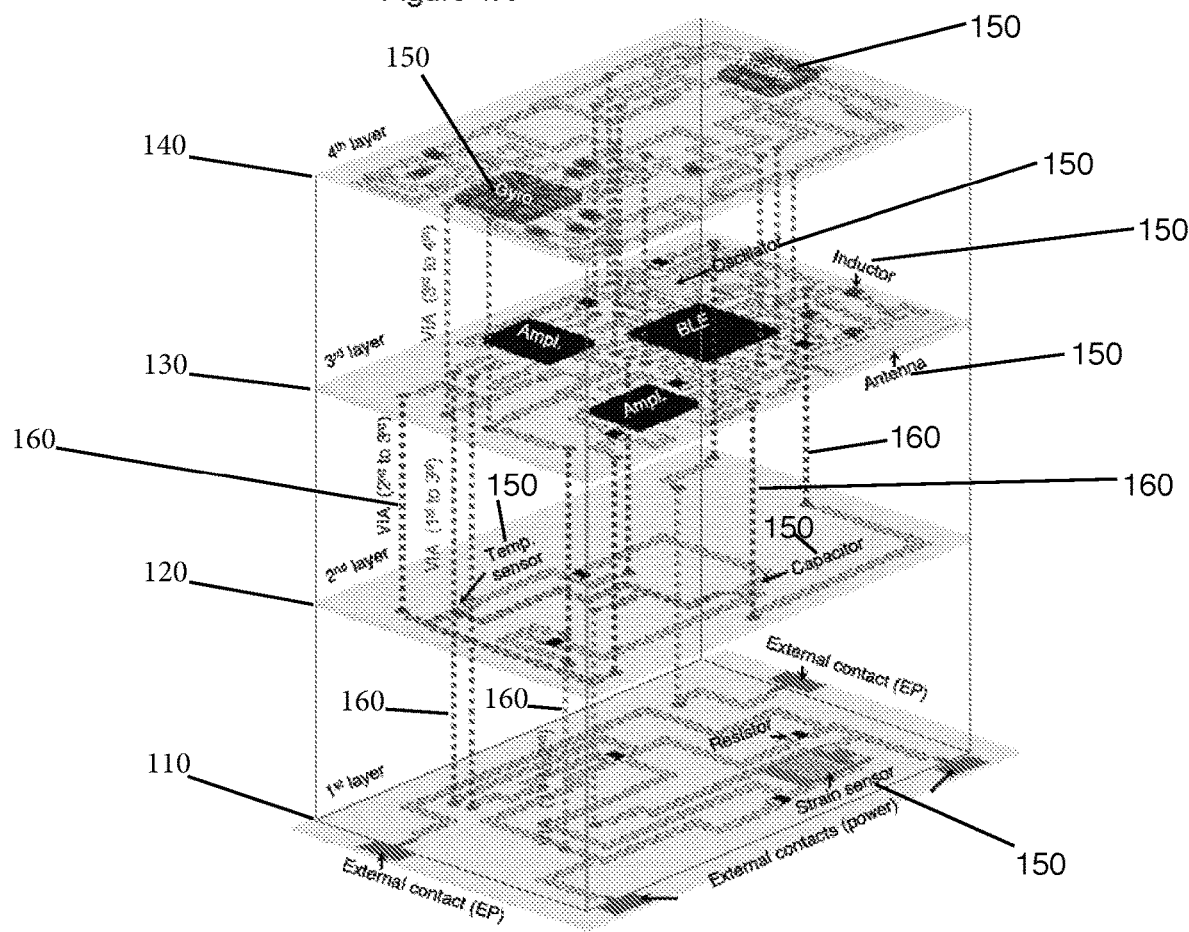

FIGS. 1A-1C show one example of a stretchable and flexible electronic device having multiple functional layers that each include one or more functional electronic elements. While the example shown in FIGS. 1A-1C have four functional layers, more generally any number of functional layers may be employed, and in some embodiment three or more functional layers may be employed. In (A) of FIG. 1, an exploded schematic view of the device is shown. In this example the device includes functional layers 110, 120, 130 and 140. Each functional layer includes one or more functional electronic elements 150. Vias 160 are used for inter-layer electrical connections.

As discussed in more detail below, the device is built functional layer by functional layer. Each functional layer employs an "island-bridge" layout to accommodate the mechanical mismatch between the rigid functional components and the silicone elastomer matrix. Each island hosts a functional component, ranging from electrodes and sensors, to active (amplifiers and RF components), and passive (resistors, capacitors, and inductors) components. The components are interconnected in-plane by stretchable "bridges"—bilayers of Cu/Polyimide (PI) thin film in a serpentine geometry that buckles in response to matrix deformation. VIAs for interlayer connection are created from conductive fillings in craters or channels in silicone. The dashed lines in FIG. 1A indicate the positions of the VIAs in the system, with the integrated and cross-sectional schematics shown in more detail below in connection with FIGS. 5A-5E. In between layers, an ultra-low modulus silicone is used to encapsulate the components for mechanical robustness and minimal constraint on the overall device stretchability. The overall device dimension is ~30×19×2 (L×W×T) mm$^3$ (see (b) in FIG. 1), comparable to a U.S. dollar coin. The final system achieved 50% stretchability in vertical, 35% in horizontal, and 20% in equal-biaxial directions (discussed in more detail below in connection with FIGS. 6-8). Reversible elastic stretchability can be achieved at a vertical strain of 30%, a horizontal strain of 25%, and a biaxial strain of 15%. The device can be cycled for more than 2000 times with 10% uniaxial strain at a frequency of 0.5 Hz (discussed in more detail below in connection with FIGS. 9A-9B). The exceptional compliance and robustness of the system when twisted and poking are shown in (B) of FIG. 1, which are optical micrographs of the system in freestanding, twisted at 90°, and poked with a dome height of ~8 mm, highlighting its superb mechanical compliance and robustness.

To visualize the mechanical behavior of the multilayer system, we imaged the 3D configuration of the device at 0 and 35% strain with micro x-ray computed tomography (micro-XCT). This is illustrated in (C) of FIG. 1, which shows XCT images of the system at 0 and 35% uniaxial tensile strain. The top left insets of (c) show the zoomed-in cross-sectional views of a VIA between two adjacent layers. The VIA connection remains intact under stretching. The lower right insets highlight the interlayer mechanical coupling that leads to nonuniform deformation in the Cu interconnects. The XCT imaging resolution is 9 µm.

A major difference between the multilayer device shown herein from a single layer configuration is the mechanical coupling between layers. The chips/interconnects can add mechanical loading to the local elastomer matrix and result in strain non-uniformity in nearby layers. Strain is concentrated in areas in between the rigid components, and achieves a minimal level in areas directly above or below the rigid components. Therefore, the embedded serpentine interconnects are not deformed uniformly across the entire device area. The size of the non-uniformly strained area is dependent on two factors: the size of the rigid component, and the separation between the rigid component and the stretchable interconnect. Detailed experimental and finite element analysis (FEA) results show that the non-uniformly strained area increases with increasing the rigid component size and decreasing the separation (discussed in more detail below in connection with FIGS. 10A-10D).

Cross-sectional XCT images of the device at 0 and 35% strain (shown in the insets of (C) in FIG. 1) depicts the VIA behavior under stretch. The VIAs do not show delamination or significant deformation. A complete cross-sectional view shows the four-layer Cu interconnect layout, the active and passive components, and the interlayer VIAs (discussed in more detail below in connection with FIGS. 11A-11E). The overall dimensions of the multilayer system are limited by the plastic packaging material thickness of the COTS chips. For example, an amplifier bare die is 0.3 mm thick, much thinner than its packaged thickness of 1.7 mm (discussed in more detail below in connection with FIGS. 12A-12D). If bare dies are used for all of the components, it would be possible to decrease the overall system dimension to ~15× 9.5×0.6 mm$^3$.

VIA Formation

To form the VIAs, the elastomer matrix needs to be selectively removed with micron scale precision before a conductive filling is deposited. The VIA size needs to be small to minimize stress localization. Moreover, the VIAs are built in a complex material system—silicone and PI on top of Cu pads in our case (discussed in more detail below in connection with (E) in FIG. 5). Since silicones are notoriously difficult to etch, we employ laser ablation, a direct-write mass removal method (22), as a fast, precise, and scalable VIA formation strategy. With a beam waist of 25 µm and a depth of focus of 600 µm, the laser can etch a VIA in silicone with a depth of 100 µm and a diameter as small as 45 µm (discussed in more detail below in connection with FIGS. 13A-13D and 14A-14B). The laser ablation process is also used to pattern the Cu serpentine interconnects with a line width of 25 µm, streamlining the fabrication process (discussed in more detail below in connection with FIG. 15).

Selectivity for VIA formation is achieved by three considerations. First, the laser wavelength is selected to have a low impact on Cu structural integrity. The laser absorption by Cu shows that absorption at 1064 nm is about 8 times weaker than at 532 nm, as shown in (A) of FIG. 2. Second, due to the low absorption of visible-IR range nanosecond laser by silicone, we incorporate dyes in the elastomer to enhance absorption and therefore lower the ablation threshold. Silicone that incorporates black dye (3% wt, Silc Pig®, Smooth-On, discussed in more detail below in connection with FIG. 16) is found to have the highest absorption at 1064 nm. Femtosecond laser can also be used without dye due to its nonlinear absorption at high intensities. Third, the laser pulse energy is optimized by tuning the optical attenuation (discussed in more detail below in connection with FIGS. 21A-21B) and its effect on different materials is studied (discussed in more detail below in connection with FIGS. 18A-18B). Below a threshold energy, laser excitation will not provide sufficient thermal energy for material ablation. The threshold energies for different materials (including silicone with different dyes) are summarized in (B) of FIG. 2 (1064 nm) and FIG. 19 (532 nm). The ablation threshold for Cu varies from 0.34 mJ with 1064 nm laser to 0.02 mJ with 532 nm laser, corresponding to the Cu absorption at these laser wavelengths discussed above. The threshold for black silicone and PI with 1064 nm laser is 0.1 mJ and 0.05 mJ, respectively. Therefore, pulse energies in the range of 0.1 mJ-0.34 mJ allows selective removal of the PI and black silicone in the presence of Cu (discussed in more detail below in connection with FIGS. 14A-14B and 20A-20B).

We demonstrate three types of VIAs with 1064 nm nanosecond pulsed laser ablation: through VIA—open on both sides, buried VIA—open on neither side, and blind VIA—open only on one side of the stretchable circuit. Fabrication is carried out on soft multilayered silicone-Cu structure (discussed in more detail below in connection with FIGS. 21A-21B). The VIA width and depth are controlled by laser writing pattern and ablation pulse numbers. Increasing the pulse number will increase the ablation of all materials. With a well-designed process parameters (discussed in more detail below in connection with FIG. 22A-22C), sophisticated VIA structures are demonstrated (discussed in more detail below in connection with FIG. 23).

FIG. 2 shows in (C)-(E) cross-sectional electron dispersive spectroscopy mapping graphs of through, buried, and blind VIAs fabricated in silicone elastomers. Silicone elastomer provides insulation between Cu in each layer; VIAs form the electrical connection through the conductive filling. The nonuniform shapes of the VIAs are caused by the cross-sectional sample preparation processes. The inset of (C) in FIG. 2 shows the tilted view of the through VIA with an increasing diameter from 300 μm at the $1^{st}$ layer to 600 μm at the $4^{th}$ layer, ensuring sufficient contact area between the Cu pad and the conductive fillings, $Sn_{42}Bi_{57.6}Ag_{0.4}$ solder in this case. Flux solution is used to remove Cu oxide layer generated by laser heating (discussed in more detail below in connection with FIGS. 24A-24B and 25A-25B), which would otherwise weaken the solder bonding. The solder paste is dispensed into the VIAs by screen printing (discussed in more detail below in connection with FIGS. 26A-26B).

Figures 2A, 2B:
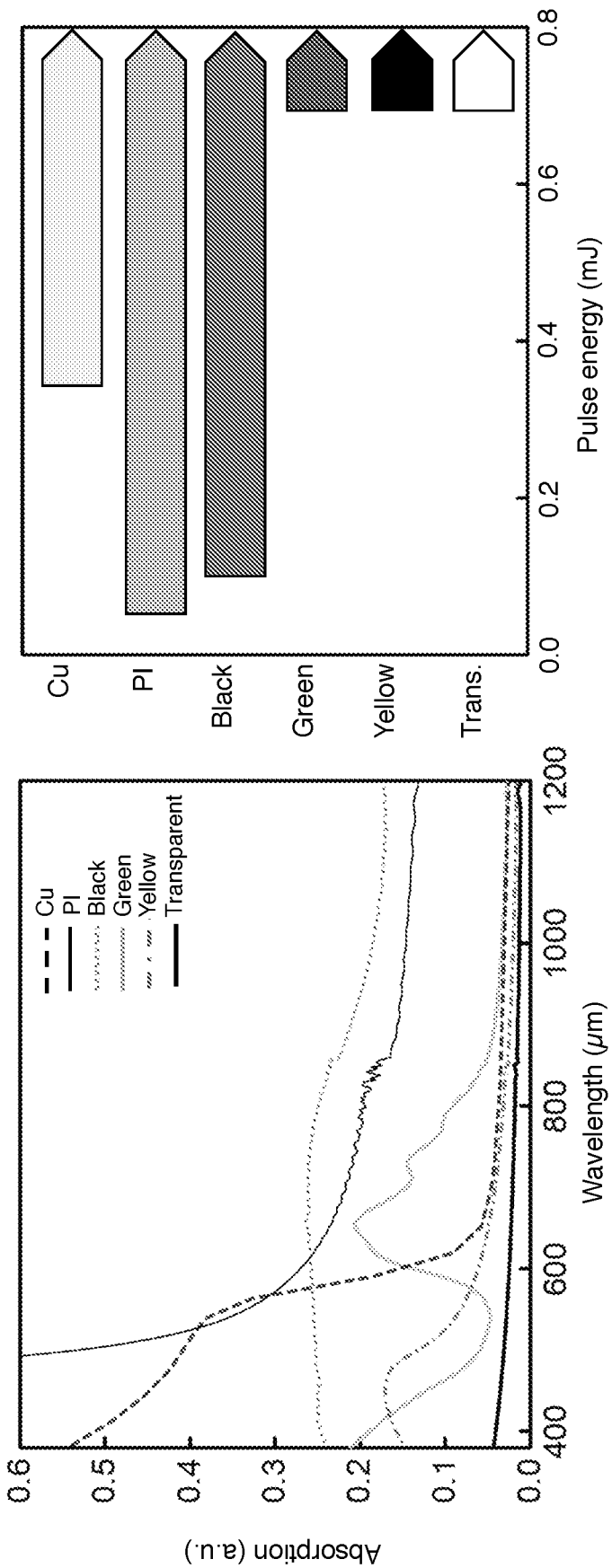
Figure 3A:
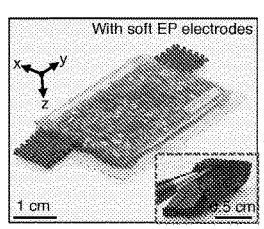
FIGS. 3A-3H show optical images and operational data from a four-layer stretchable and flexible electronic device.
Figure 3B:
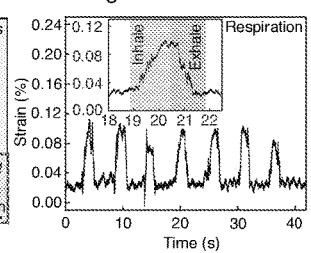
Figure 3C:
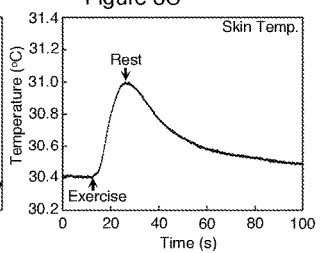
Figure 3D:
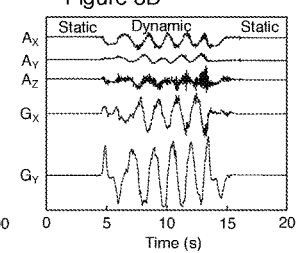
Figure 3E:
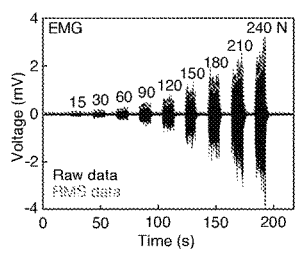
Figure 3F:
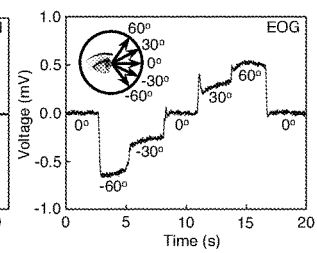
Figure 3G:
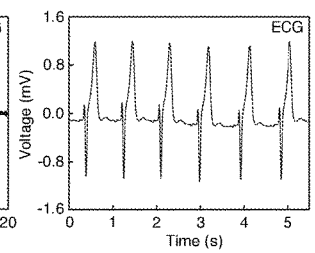
Figure 3H:
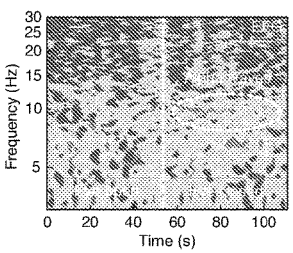

A 10-layer stretchable heater was fabricated to demonstrate the scalability of this process. FIG. 2 in (F) shows the top view of the 10-layer device (see FIGS. 27A-27B for a detailed schematic illustration of the device structure). All the layers are connected in series, with a total thickness of 1.1 mm. Each layer has a heater in the middle of the Cu interconnection and a VIA at the vertex of the decagram. The device is designed to have a decagram layout: each layer is designed to have a heater at the midpoint of the connection line, and a VIA at the vertex. The thermal image of the powered decagram heater with 59.3 mW power for each heater is captured in (G) of FIGS. 2A-2H and FIGS. 28A-28C. The depth of the heater embedded in the elastomer decreases from the $1^{st}$ layer to the $10^{th}$ layer. Therefore, the observed temperature increases sequentially. The temperature difference at each heater location originates from the different layer depths from the device top surface. The thermal image of the device is shown in (H) of FIG. 2 under 30% uniaxial strain; the temperature difference becomes insignificant due to the decrease of the device thickness, and thus the depth variations.

Multi-Channel Data Acquisition for Vital Signal Monitoring

The 3D integration enables not only high component densities in stretchable electronics, but also new functions that are challenging to implement with conventional single-layer designs of a reasonable footprint size. An example of such new functions is Bluetooth, which involves large amounts of passive components and complex wiring. In the illustrative device as designed in (A) of FIG. 1, we have incorporated a strain sensor in Wheatstone bridge scheme and releasable contact pads for power and local field potentials (first layer), a temperature sensor with a low pass filter (second layer), a system-on-chip Bluetooth integrated circuit with a 2.4 GHz antenna, an impedance matching circuit, and a local field potential amplifier (third layer), and a gyroscope and an accelerometer (forth layer). The four-layer device was fabricated layer by layer by transfer printing (discussed in more detail below in connection with FIGS. 29A-29D). The VIA diameter is 500 μm to accommodate the maximum interconnection distortion of about 150 μm (discussed in more detail below in connection with FIGS. 30A-30F) and maximum alignment error of about 120 μm (discussed in more detail below in connection with FIGS. 31A-31B and 32A-32C) in transfer printing.

The device is designed to record electrophysiological signals from the human body when attached to the skin by van der Waals forces. Intimate contact with the skin is key to acquiring high signal-to-noise-ratio signals due to its low interfacial parasitic capacitance. The device is connected with two 8×8 $mm^2$ soft electrodes as shown in (A) of FIG. 3, which is an optical image of the system integrated with CNT/silicone electrodes for electrophysiological potential (EP) measurements. The inset shows an optical image of a deformed electrode. The sensors are soft and sticky and can achieve conformal contact to the skin without any gels. Each electrode is made from a multiwall carbon nanotube (CNT)/silicone (Silbione®, Elkem Silicones) composite. Because of its low Young's modulus (40 kPa, discussed in more detail below in connection with FIGS. 33A-33B) compared with that of human epidermis (140 to 600 kPa, (1)), the CNT/silicone composite conforms to the skin without causing discomfort, and bypasses the need for conductive gels as a contact promoter. Its high electrical conductivity, low piezoresistance (discussed in more detail below in connection with FIGS. 34A-34B), and long-term stability ensure high signal-to-noise-ratio (discussed in more detail below in connection with FIGS. 35A-35D) and a lifetime of more than half a year (discussed in more detail below in connection with FIGS. 36A-36B).

Powered by a 3 V pouch cell, the multi-functional soft system can be used to simultaneously record human respiration, skin temperature, and body motion when mounted on the chest. The chest movement when breathing is detected with the strain sensor. FIG. 3 shows in (B)-(D) signal measurements with the device mounted on the chest. (B) of FIG. 3 shows the measured bending strain corresponding to repeated inhaling and exhaling. The skin surface temperature is recorded with the temperature sensor, showing a rapid increase with physical exercise and slow recovery with rest (see (C) in FIG. 3). Signals from the accelerometer along x, y, and z axes, $A_x$, $A_y$, and $A_z$, and the gyroscope along x and y axes, $G_x$ and $G_y$, are recorded during walking (see (D) in FIG. 3). The device can communicate wirelessly via Bluetooth Low Energy 4.0 technology with a smartphone or a laptop at distances of up to 10 m. The received signal strength indicator varies from −55 dBm at 0.5 m to −80 dBm at 10 m (discussed in more detail below in connection with FIG. 37). The circuit design, device workflow, and components used are discussed in more detail below in connection with FIGS. 38-40).

The local field potential amplifier can be applied to record various electrophysiological signals depending on the device location. When mounted on the forearm, electromyogram (EMG) is recorded with different grasping forces, calibrated with the commercial hand dynamometer. This is shown in (E) of FIG. 3, where root mean square is calculated to quantify the increasing EMG signal intensity. When mounted on the side head, electrooculograph (EOG) is acquired with gaze angles from −60° to +60°. The results are shown in (F) of FIG. 3. When mounted on the chest or abdominal area, electrocardiograph (ECG) is recorded with P, Q, R, S, and T waveforms clearly identifiable. These results are shown in (G) of FIG. 3 and FIG. 41. When mounted on the forehead, electroencephalograph (EEG) is recorded, with distinguishable signals during mental exercise with open eyes and relaxation with closed eyes. This is illustrated in (H) of FIG. 3. The alpha rhythms with frequencies from 8 to 13 Hz in EEG during the closed-eye state clearly indicate the activity of the visual cortex in an idle state. Additional experimental details about the electrophysiological sensing position, and EMG and EOG data processing are discussed in more detail below in connection with FIGS. 42 to 45C).

Wireless High-Degree Robotic Arm Control

Figure 4A:
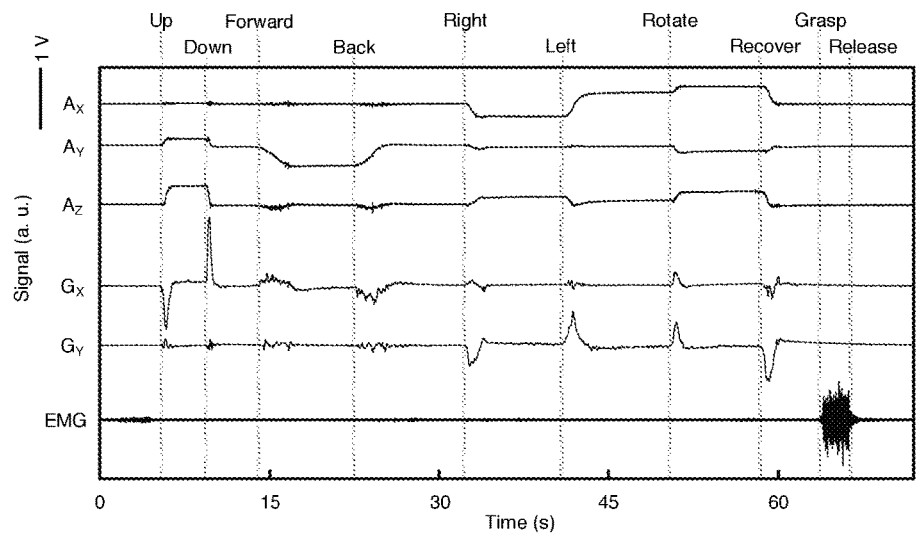
FIGS. 4A-4B illustrate aspects of the wireless control of a robotic arm using one example of the stretchable and flexible electronic device described herein.
Figure 4B:
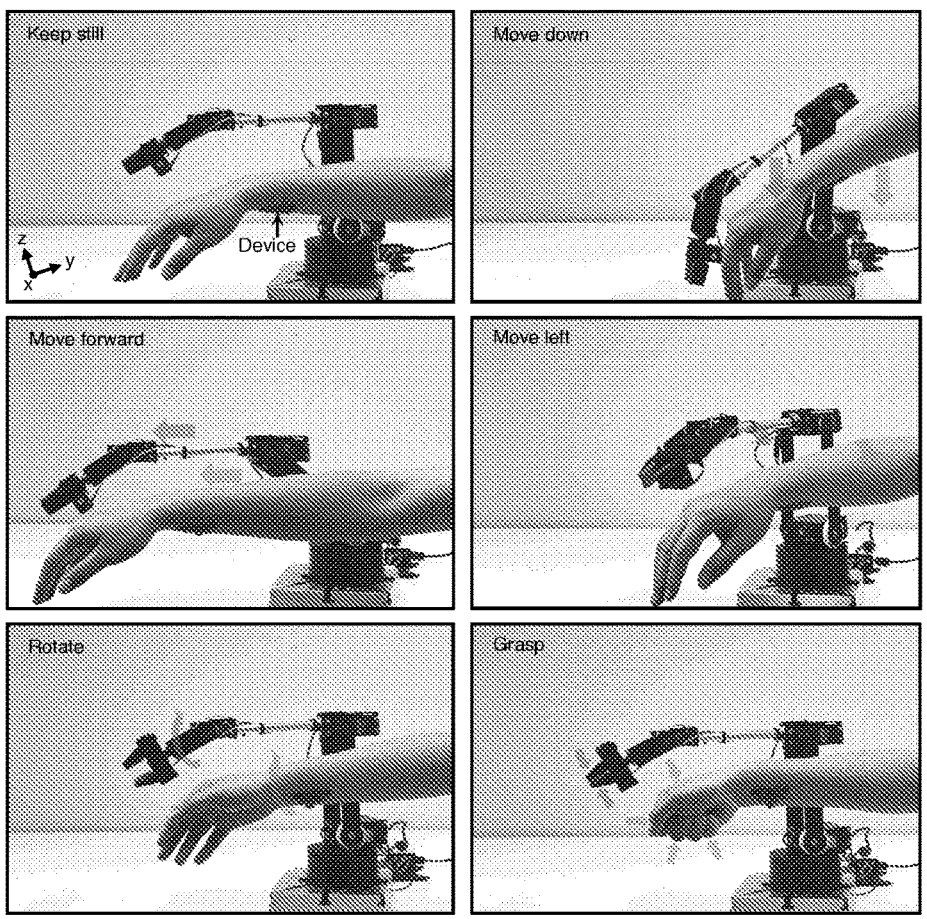

An exemplary application of the 3D integrated stretchable system is a noninvasive human-machine interface. The rich variety of signals from the human body can be used as a source of command for controlling robotics and prosthetics. The stretchable multifunctional device is mounted on a human forearm through van der Waals forces, and used to wirelessly control a robotic arm (Lynxmotion AL5D arm with upgraded wrist rotate and SSC-32U USB board communication, discussed in more detail below in connection with FIG. 46). Six signals acquired on the arm, including three-channel acceleration, two-channel angular velocity, and EMG signals, are used to control the robotic arm with six degrees of freedom, as shown in FIGS. 4A and 4B. With real time wireless data communication and algorithm analysis, the robotic arm can quickly identify and imitate the human arm gesture.

A graph of the acceleration ($A_x$, $A_y$, and $A_z$), angular velocity ($G_x$ and $G_y$), and EMG data acquired from different arm motions with the device mounted on the forearm is shown in (A) of FIG. 4. The acceleration data are used to control the translational movement, the angular velocity data are used to control the rotational movement, and the EMG signals are used to control the grasping of the robotic arm. Pictures showing the robotic arm controlled by the actions of the human arm are shown in (B) of FIG. 4. With real time wireless data communication and algorithm analysis, the robotic arm can quickly identify and imitate the human arm gesture.

The design and fabrication methods presented here establishes the engineering basis for building 3D integrated stretchable electronic systems, which not only enables exponential growth of the function density, but also opens up new functionalities with complex interconnect layouts that are challenging in single-layer designs. The results represent a key step in the developmental roadmap of soft wearable electronics. Similar principles can be applied to stretchable systems built with other material ensembles. The stretchable eight-channel sensors that allow the extraction of a suite of signals from the human body in an unprecedentedly compact soft format, and the Bluetooth enabled by multilayer interconnected circuits demonstrated here can lead to new venues in smart connected healthcare, wireless control schemes for human-machine interface, and internet-of-things.

Design Rationale for the Multifunctional Circuit

Bluetooth (chip 22 shown in FIG. 40, discussed below) collected eight channels of signals simultaneously from the accelerometer (along x, y, and z directions), gyroscope (along x and y directions), strain sensor, temperature sensor, and electrophysiological module, with 10-bits analog digital converter (ADC) for converting analog signals of each channel to digital signals. Capacitors of 0.1 g (chip 15 in FIG. 40) were used to decouple the power supply. All clocks in Bluetooth were derived from the 16 MHz oscillator (chip 23 in FIG. 40). The Bluetooth sent out the signals by a 2.4 GHz antenna (chip 6). The signals could be received at 10 meters away by a separate Bluetooth.

The strain sensor (chip 1 in FIG. 40) was embedded in a Wheat-Stone bridge that was specially designed with ~350Ω resistance. The bridge output signals to the amplifier (chip 17, upper, in FIG. 40). After 820 times amplification, the signal of zero-strain was 1.97 V, which was then transmitted to the Bluetooth.

The electrophysiological module acquired signal from the Cu pads in first layer with a filter comprised of chips 15, 20, and 21 at the top right corner of the third layer in FIG. 40. The signal was amplified for 820 times (chip 17, lower, in FIG. 40), and then collected by the Bluetooth.

The temperature sensor was a negative temperature coefficient thermistor. The signal passed a filter comprised of chips 4 and 5 (FIG. 40), and was then transmitted to the Bluetooth.

The accelerometer (chip 30 in FIG. 40) could generate three channels of accelerations along three orthogonal axes. All channels were filtered by a bypassing capacitor (chip 15 in FIG. 40) before feeding into the Bluetooth.

The gyroscope was decoupled by chips 15 and 21 (FIG. 40) at the left bottom corner of the forth layer in FIG. 40. Two channels of angular velocities were filtered by a band-pass filter that was connected to the gyroscope in series.

Topological structure design of the device aims to minimize the interconnect complexity in each layer and number of VIAs between the layers. The strain sensor and temperature sensor were placed in the first two layers that were close to the skin to minimize the possible signal attenuation. To reduce the surface roughness of the first and second layers of the device due to the height variation of the chips, chips in these two layers were chose to be with a thickness smaller than the encapsulating Ecoflex. Specifically, chips with 01005 packaging that had a thickness of 0.13 mm were selected. For the third and fourth layers, we chose chips with 0603 packaging, with 0.8 mm in width and 1.6 mm in length, to simplify the bonding process.

Mechanical Pattern Design of the Serpentine Electrodes

Figure 48:
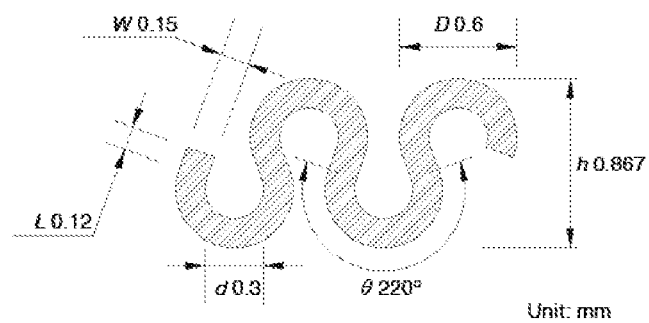
FIG. 48 shows the mechanical pattern design for one example of the serpentine electrodes.

As shown in FIG. 48, a horseshoe serpentine design was employed as the interconnect between the components, with 0.6 mm for external diameter (d), 0.3 mm for internal diameter (d), 220° for curvature (θ) 0.12 mm for ribbon length (L), and 0.15 mm for ribbon width (W). The total height of each horseshoe h was 0.867 mm.

There were three criteria for choosing these parameters: (1) The width and the narrowest part in the serpentine should be wider than the resolution of the laser ablation (25 μm); (2) The total height of the horseshoe interconnect should be suitable for the density of chip pins. The space between adjacent pins of the chips should be sufficient for accommodating the interconnects. (3) d/W, L, and θ should be as large as possible to maximize the device stretchability.

Fabrication of the Interconnect Network

A layer of PMMA (495K, A6) was coated on the glass with a spin speed of 1500 rpm for 30 s, and was cured by soft baking on a hot plate at 150° C. for 1 min. Next, spin coating formed a 100 μm thick layer of Ecoflex (Smooth-On, Easton, Pa., 1:1) over the PMMA. The Ecoflex was cured at room temperature for 2 h. A layer of polydimethylsiloxane (PDMS, Sylgard 184 silicone elastomer, 20:1) was coated on a separate clean glass slide at 3000 rpm for 30 s, followed by curing in an oven at 110° C. for 30 min. A Cu sheet (20 μm thick, Oak-Mitsui, Inc.) was coated with polyimide (PI, from poly(pyromellitic dianhydride-co-4,40-oxydianiline) amic acid solution, PI2545 precursor (HD MicroSystems)) at 4000 rpm for 60 s, soft baked on a hotplate at 110° C. for 3 minutes, 150° C. for 1 min and fully cured in a nitrogen oven at 300° C. for 1 h sequentially, and then transferred on the surface of the prepared PDMS/Glass substrate. Interconnect layout was designed by the AutoCAD software and input into laser system for the Cu patterning. Next, the laser (1064 nm), with pulse energy 0.42 mJ, pulse width 1 µs, frequency 35 KHz, and mark speed 500 mm/s, was used to ablate the Cu film into the designed pattern. After removing the residual, the Cu pattern was picked up by water soluble tape (3M, Inc.) for transfer printing onto prepared Ecoflex/PMMA/Glass substrate or existing matrix of the device.

Assembly of the Chip Components

Both the Ecoflex substrate and interconnections on the water-soluble tape (exposing the PI side of the Cu electrode) were activated by UV ozone for 3 mins. For the first layer, the interconnection was directly laminated on the Ecoflex substrate and heated in the oven at 80° C. for 15 minutes to enhance the bonding between the PI layer and the Ecoflex. Then the water-soluble tape was removed by room temperature tap water. After drying by the air gun, the Cu interconnection was cleaned by flux (WOR331928, Worthington, Inc.) to remove the surface oxide layer, which would benefit the formation of Cu/Sn alloy for enhanced electrical bonding. The $Sn_{42}Bi_{57.6}Ag_{0.4}$ alloy paste (Chip Quick Inc. SMDLTLFP-ND, low melting point of 138° C.) was screen-printed onto Cu pads with a shadow mask (thickness 75 µm). Polished chips with reduced dimensions were well aligned on the Cu pads, reflowed by baking on a hotplate at ~150° C. for 5 minutes, and then cooled down to room temperature to form good wetting properties.

VIA Formation and Aligned Transfer Printing

Concentrated color pigments (Silc Pig, Smooth On, Inc.) were used to modify silicone absorptivity for selective etching of silicone from Cu. Ecoflex part A was mixed with the pigments (1.5% wt of the part A) first, followed by adding Ecoflex part B (A:B=1:1 by weight). With spin coating, the existing circuit layer was fully encapsulated with 100 µm thick layer of colored silicone. A thin film shadow mask was used to separate the external Cu pads (for EP and power contacts) from the silicone encapsulation. After taking away the mask, the device was put into oven at 80° C. for 30 minutes to fully cure the silicone.

Then laser ablation was used to create VIAs through the silicone. There are two things to be noted. First is to align the designed CAD VIA pattern with the device. Second is to form the VIAs, by selectively removing the silicone without damaging bottom Cu pad.

1. Strategies for Laser Alignment

Laser alignment meant to match the existing pattern in the sample to the pattern on the CAD design file that would be processed by the laser. At least two alignment markers were installed in each pattern. These markers indicated the positions of x, y, theta of patterns in the camera on the laser cutting equipment. There were two ways to align both patterns, by either moving the sample using the mechanical stage or changing the pattern location and orientation in the CAD design. In our study, we used the latter way because it was more accurate and convenient than the former one. Detailed procedures are listed below:

1) Add Alignment Markers on the Sample

Each sample needed at least two alignment markers to identify its location coordinates (x, y, and theta). So, two alignment markers were added at point A $(X_A, Y_A)$ and point B $(X_B, Y_B)$ on both the sample pattern and the CAD design file.

2) Calibrate the Laser Ablation Location in the Camera

Once making a laser ablation marker on a dummy sample, we could see the actual ablation locations on the sample of points A and B from the CAD design. We then recorded the locations of the markers in the camera sight, which would be used as the reference positions.

3) Check the Alignment Discrepancy Between the Sample and the CAD Design

The sample with location points A and B was placed on the stage. Comparing with the reference positions, we could see location difference between the position in the camera sight and the one on the CAD design file, i.e., $(\Delta X_A, \Delta Y_A)$ and $(\Delta X_B, \Delta Y_B)$.

4) Match the Pattern Location in the CAD File to the Actual Sample Location

Shift and rotate the pattern location on the CAD file to cancel the discrepancy, $(\Delta X_A, \Delta Y_A)$ and $(\Delta X_B, \Delta Y_B)$.

5) Start Laser Ablation

After the location discrepancy between the patterns in the CAD design and the actual sample was cancelled, we then started laser cutting using the parameters discussed in the text above.

2. Strategies for Selectively Etching Silicone

Ideally, selective etching was to control the laser process parameters that allowed ablating silicone without damaging the Cu underneath. To do that, first, the silicone was modified with black pigments to increase its laser absorption. Second, suitable laser wavelength was chosen. Cu has much less absorption in near infrared region than the other common laser wavelengths, such as green or UV laser, as shown in FIG. 2A. Therefore, the laser with wavelength 1064 nm was chosen to reduce the potential ablation of Cu. Finally, laser ablation parameters were systematically studied, as shown in FIG. 2B and discussed in more detail below in connection with FIGS. 18A and 18B. The optimum laser parameters to selectively etch black silicone were determined to be: pulse energy 0.14 mJ, pulse width 1 µs, frequency 35 KHz, and mark speed 500 mm/s. With well-designed laser writing patterns (discussed in more detail below in connection with FIG. 22), the etched silicone VIA diameter can be as small as ~45 µm, with an aspect ratio of ~2 and a silicone etching rate of ~1 µm per etching cycle.

With 100 cycles laser etching, VIAs were drilled through the silicone to expose the Cu pad underneath. During the high temperature laser ablation process, oxide would form on the Cu pad surface, and should be removed by flux. Otherwise it would retard the formation of alloy between the solder paste and the Cu pad and thus weaken the bonding strength at the interface. For VIAs with small diameters (45~500 µm), because of the hydrophobicity of the elastomeric surface, isopropanol alcohol (IPA) was used to mix with flux to improve the wetting and therefore cleaning outcomes, as shown in FIGS. 24A-24B and 25A-25B. By screen printing, the VIAs were fully filled by $Sn_{42}Bi_{57.6}Ag_{0.4}$ solder paste. With mild heating on the hotplate at 150° C. for 5 minutes, the paste in the VIAs was transferred into tin pillars, which were bonded to the bottom Cu pads with good wetting properties.

Figure 31A:
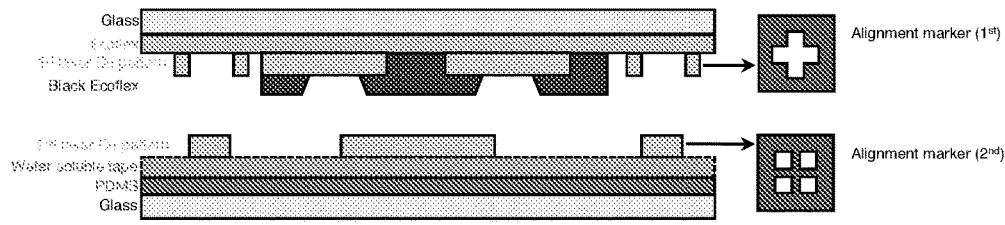
FIGS. 31A-31B show the setup for aligned transfer printing.
Figure 31B:
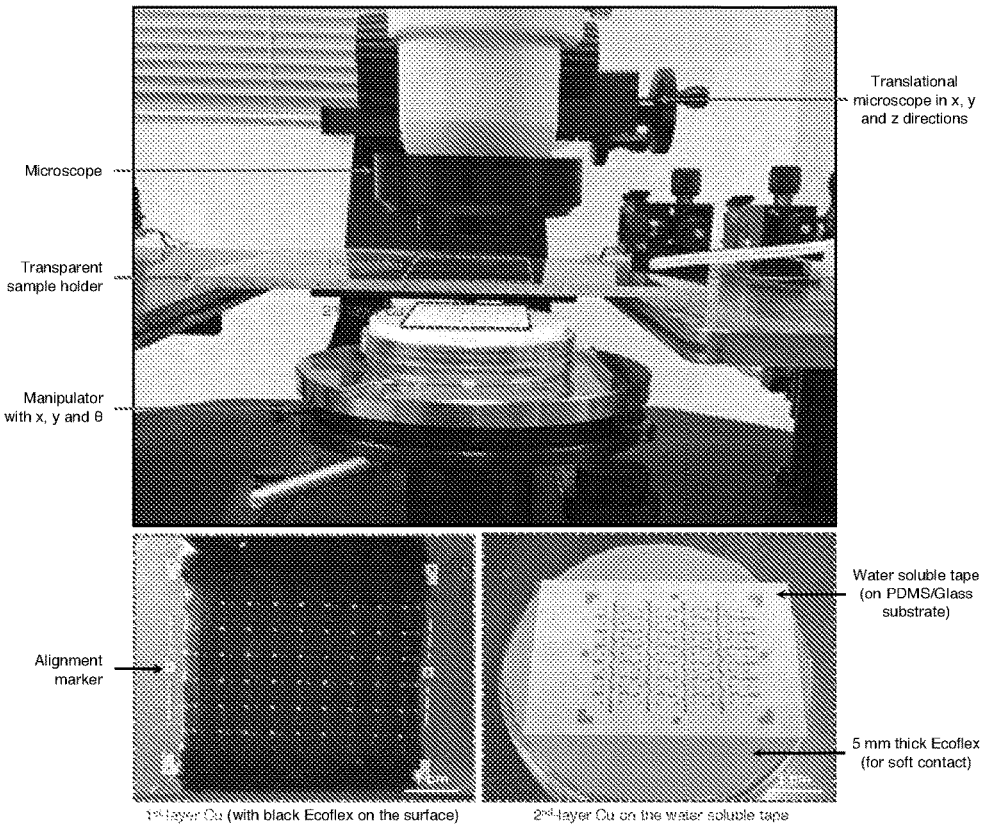

The alignment of the subsequent layer of VIA patterns with the existing island-bridge matrix was achieved by transfer printing under the microscope with integrated positioning systems, as shown in FIGS. 31A-31B. After picked up by the water soluble tape, the new layer was attached on a PDMS/Glass substrate to prevent it from curling. The existing matrix was put on a thick Ecoflex substrate (thickness 5 mm) to achieve a soft contact, which will avoid any potential damage to the device. UV ozone was used to activate both the new layer and the existing matrix for 3 minutes. With the alignment markers and positioning systems, the new layer was aligned with the existing matrix. As Ecoflex is stickier than PDMS, the new layer would be transferred from the PDMS substrate to the Ecoflex matrix, followed by heating in oven at 80° C. for 30 minutes and dissolving the water-soluble tape. The VIA structure, as shown in FIG. S1E, has a circular Cu pad in the bottom layer, a tin pillar through the silicone, an open circular Cu pad in the top layer, and a tin cap. The tin cap formed by screen printing the tin paste followed by heating on the hotplate bonded the tin pillar to the top Cu pad.

Overall Device Structure Design

The four-layer stretchable system: the first two layers were fully encapsulated with silicone (Ecoflex, Smooth-On, Easton, Pa., Young's modulus E=60 kPa) that helped recover the Cu interconnects after stretching. The third layer and forth layer, which had a handful of thicker chips, were integrated in a way that the thick chips were positioned to avoid directly stacking on top of each other to keep the overall device thickness at a minimal level. These two layers were encapsulated with an ultralow modulus solid silicone elastomer (Silbione RT, Gel 4717 A/B, Bluestar Silicone, USA, E=5 kPa) with a core/shell structure to minimize the interfacial strain and improve the overall stretchability on the system level.

The ten-layer stretchable system: the device had 10 layers with one heater in each layer and one VIA at each corner. The heaters in the 10 layers were connected by the VIAs in series and powered by a DC supply.

Silbione/Multiwalled Carbon Nanotubes (CNTs) Composites for EP Sensing

CNTs (1% wt of the part A) were firstly used to mix with Silbione part A (Silbione RT, Gel 4717 A/B, Bluestar Silicone, USA). After 2-hour stir, part B was added (A:B=1:1 by weight). Glass with a layer of deposited polytetrafluoroethylene (PTFE) was used as the substrate to fabricate the composites. The thickness of the composites was controlled to be ~1 mm. After one day at room temperature, the fabricated electrode was fully cured and could be slowly removed from the substrate. The fresh electrodes were sticky enough to be directly attached on the skin for the EP sensing. Due to the high conductivity and stability of CNTs (33), the electrodes can achieve high-quality signal for long-term EP monitor. After several measurements, the electrodes could be recycled by cleaning with IPA to remove any dirt or dead skin cells.

Robot Arm Control System

Figure 42:
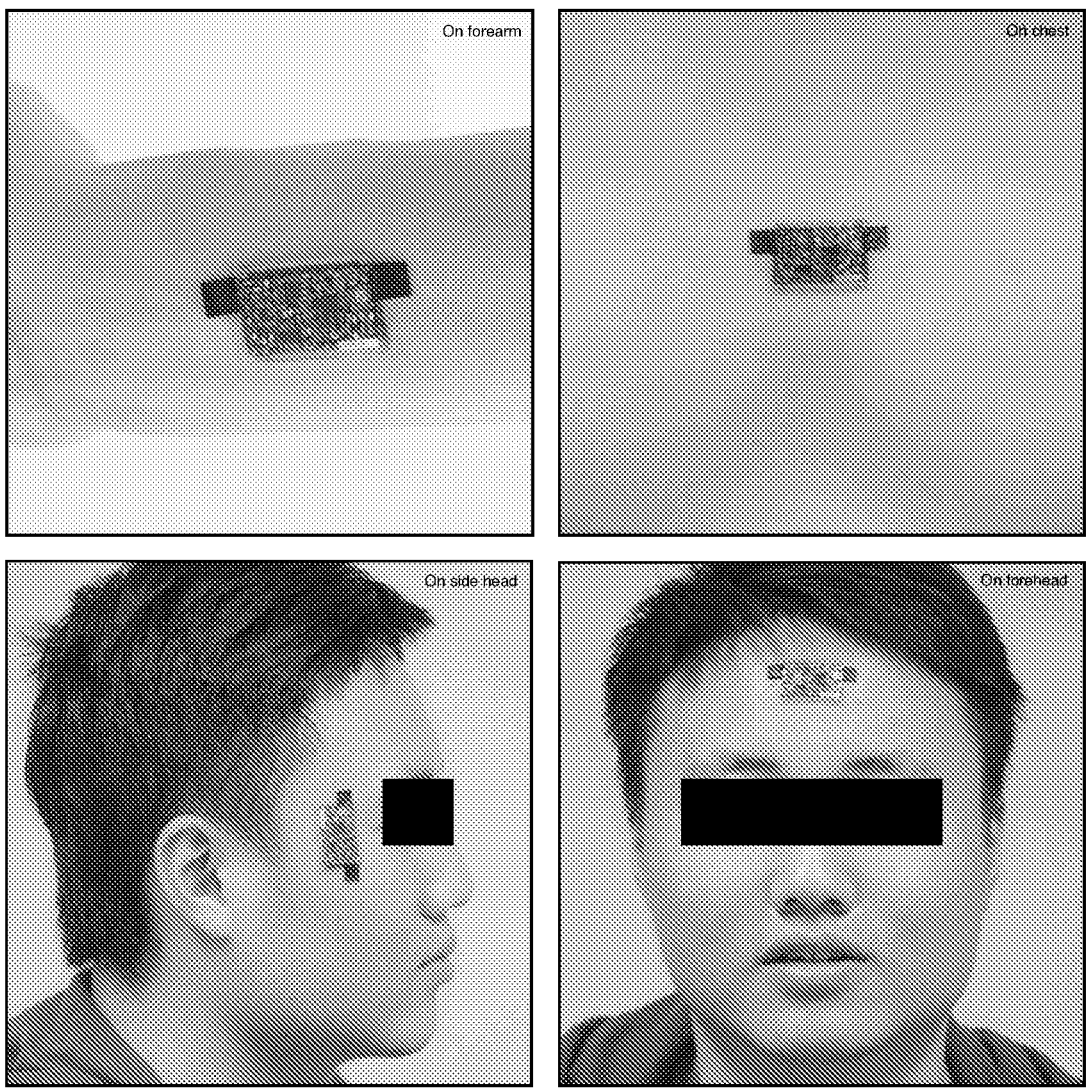
FIG. 42 are optical images showing the positions where the EP signals are acquired: on the forearm for EMG, on the chest for ECG, on the side head for EOG, and on the forehead for EEG.

The transmitting Bluetooth in the device collected signals from the accelerometer, gyroscope, strain, temperature, and EP modules, and then packaged and sent these data to the receiving Bluetooth wirelessly by protocol S130. The receiving Bluetooth was connected to a development board (BLE400), so that these packages could be delivered to a laptop through COM ports. Both Bluetooth chips were programmed by Keil μVision V5.14 to configure the resolution of ADC and packaging logics. Resolution of the gyroscope was around 0.014°/s and resolution of the accelerometer was around 300 μg, which allowed the stretchable system to capture the small motions of the human arm with high fidelity. The control software (FlowBotics Studio, RobotShop Inc.) in the laptop disassembled the package from the COM ports, calculated the sensing data, and output motion value through SSC-32U USB board for each servo of the robot arm (Lynxmotion AL5D arm with upgraded wrist rotate). Setup for the robot control system is shown in FIG. 42.

Additional Details

FIGS. 5A-5E is a schematic illustration of one example of the three-dimensional integrated stretchable and flexible system. An overview of a four-layer stretchable device with two cross-section cuts to highlight the design features is shown in (A) of FIG. 5. (B), (C), and (D) of FIG. 5 show zoomed-in views of the cuts. In particular, (B) shows vertical zero-resistance jumpers that are used as the electrical connection between the $3^{rd}$ layer and $4^{th}$ layer, to accommodate some thick chips. The first three layers use tin based VIAs as the interlayer connection. (C) shows that the four-layer device has functional sensors and passive components in each layer with VIAs among these layers for interlayer electrical connections. The stretchable system is packed in core-shell structures, with Ecoflex as the shell and ultra-low Young's modulus Silbione as the core, to increase the stretchability of the overall system. B-Ecoflex indicated Ecoflex mixed with the black dye for laser ablation. (D) and (E) of FIG. 5 show a cross-section view and an exploded view, respectively, of a typical tin based VIA. The serpentine interconnect is composed of bilayers of Cu/PI. With screen-printing, the tin pillar and tin cap are fabricated to achieve solid electrical bonding.

Figure 6:
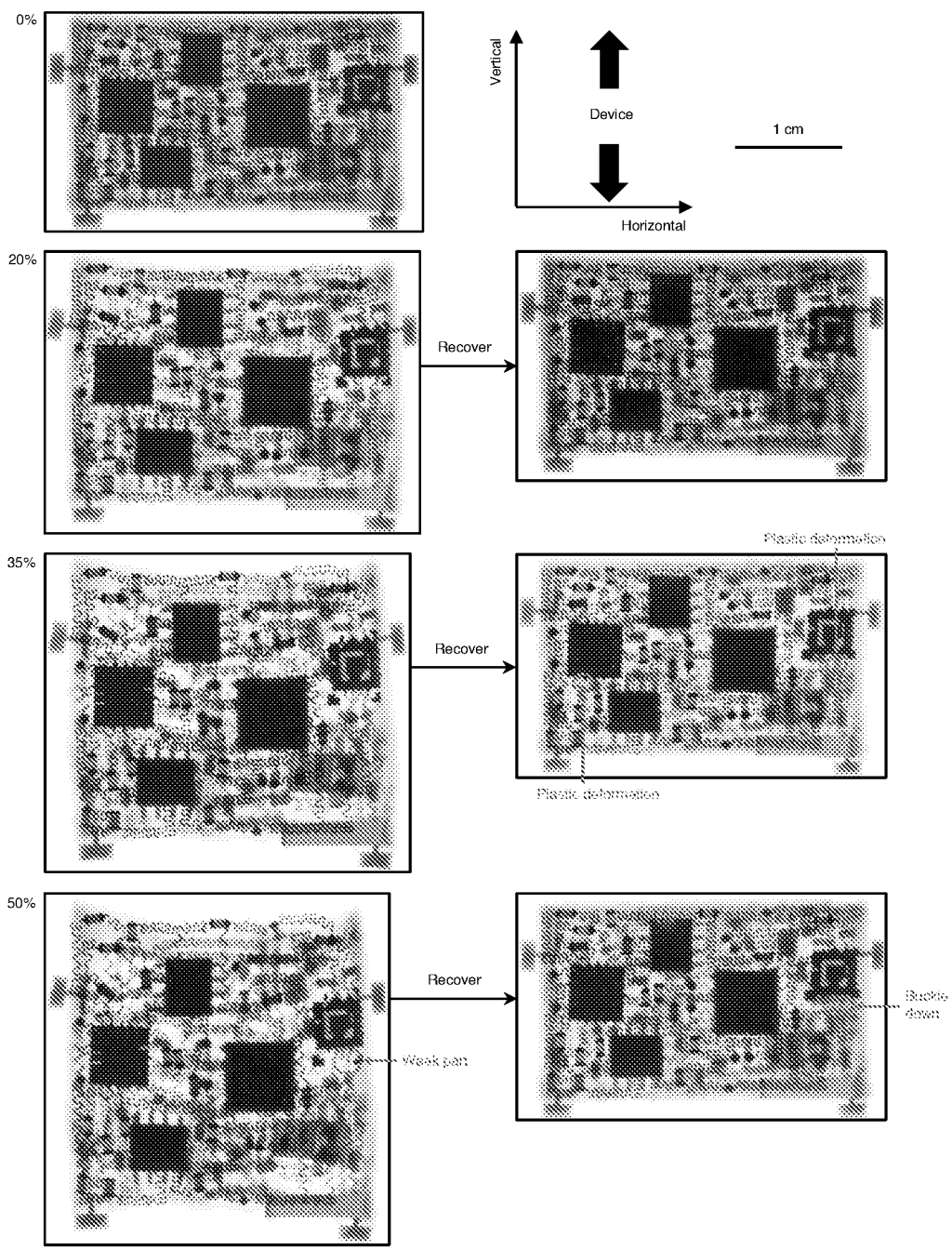
FIG. 6 shows experimental results of buckling deformations across the entire circuit under uniaxial stretching along the vertical direction.

FIG. 6 show experimental studies of buckling deformations across the entire circuits under uniaxial stretching along the vertical direction. The failure strain in the vertical direction is ~50% with weak points at the interconnect between the accelerometer and capacitor. Plastic deformation begins at ~35% strain.

Figure 7:
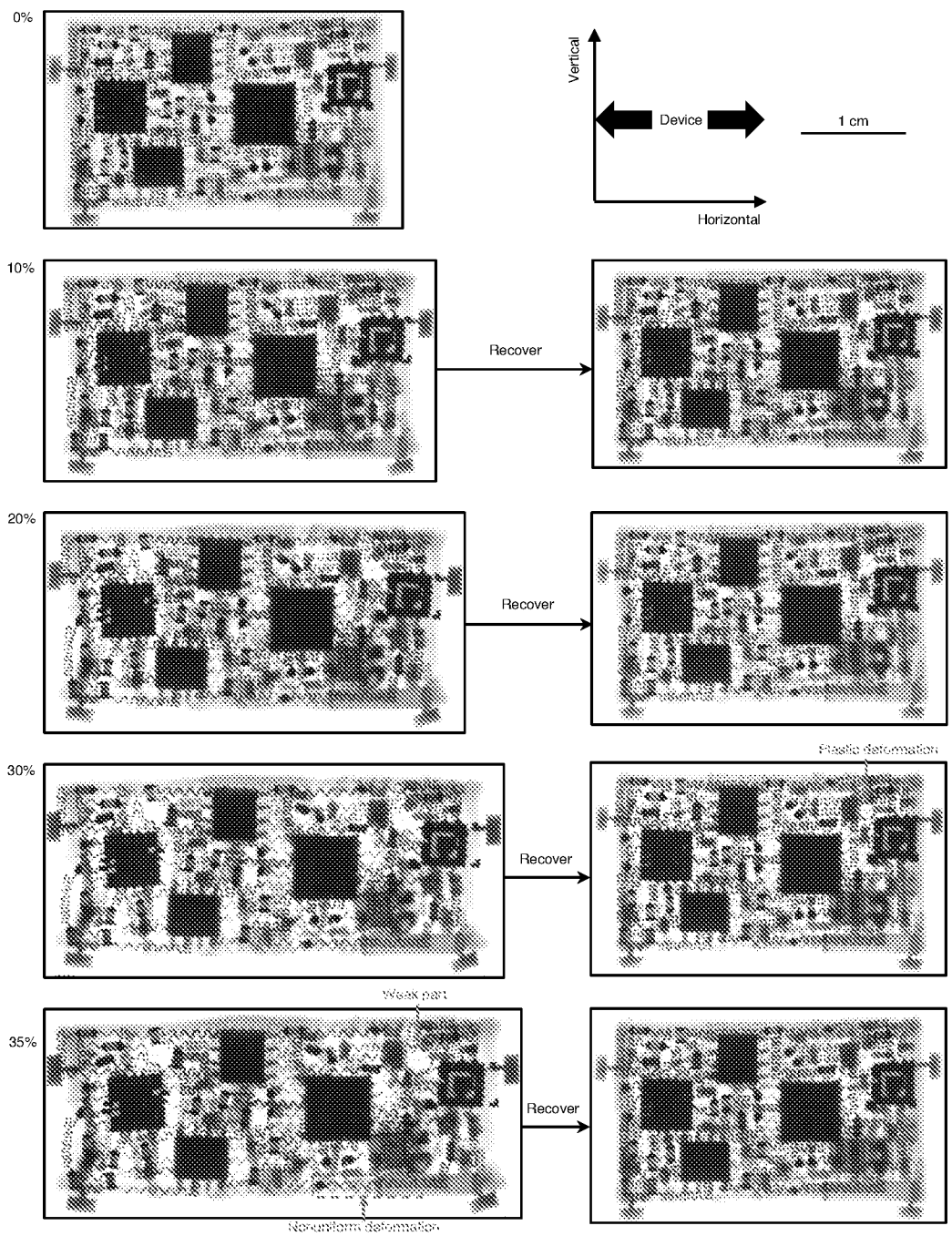
FIG. 7 shows experimental results of buckling deformations across the entire circuit under uniaxial stretching along the horizontal direction.

FIG. 7 show experimental studies of buckling deformations across the entire circuit under uniaxial stretching along the horizontal direction. The failure strain in the horizontal direction is ~35% with weak points at the interconnect between the crystal oscillator and capacitor. Plastic deformation begins at ~30% strain.

Figure 8:
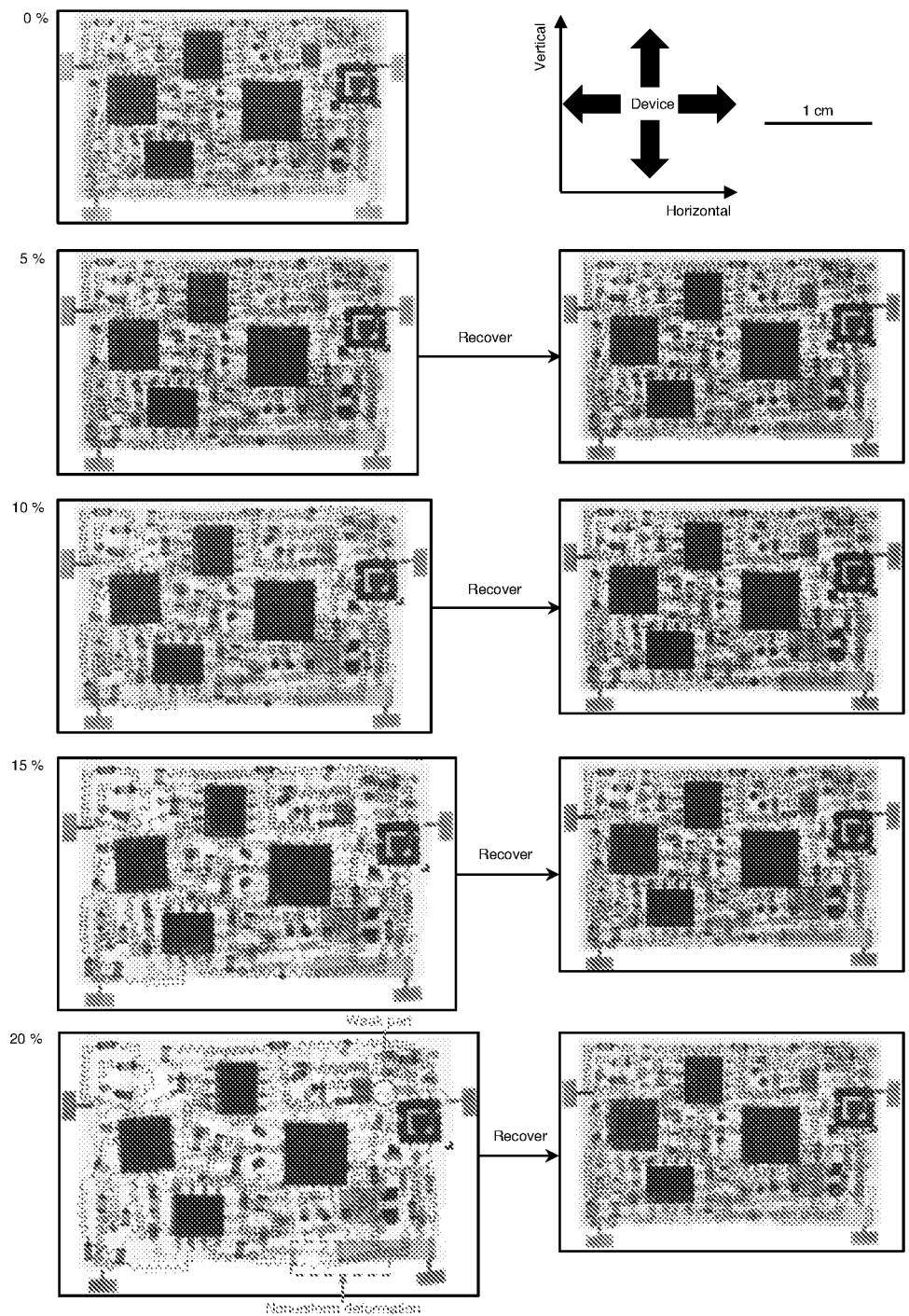
FIG. 8 shows experimental results of buckling deformations across the entire circuit under biaxial stretching.

FIG. 8 show experimental studies of buckling deformations across the entire circuit under biaxial stretching. The failure strain for biaxial stretching is ~20% with weak points at the interconnect between the crystal oscillator and capacitor.

Figure 9A:
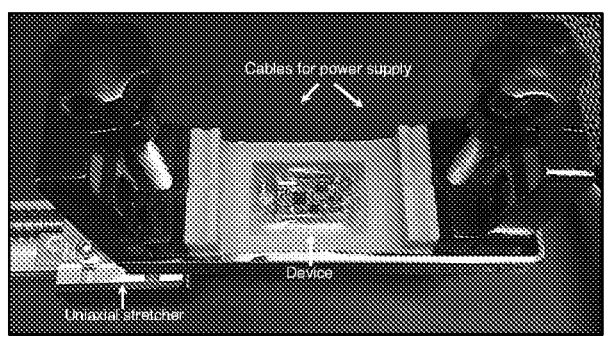
FIGS. 9A-9B show a fatigue test of the three-dimensional integrated stretchable device with 10% uniaxial strain at frequency of 0.5 Hz.
Figure 9B:
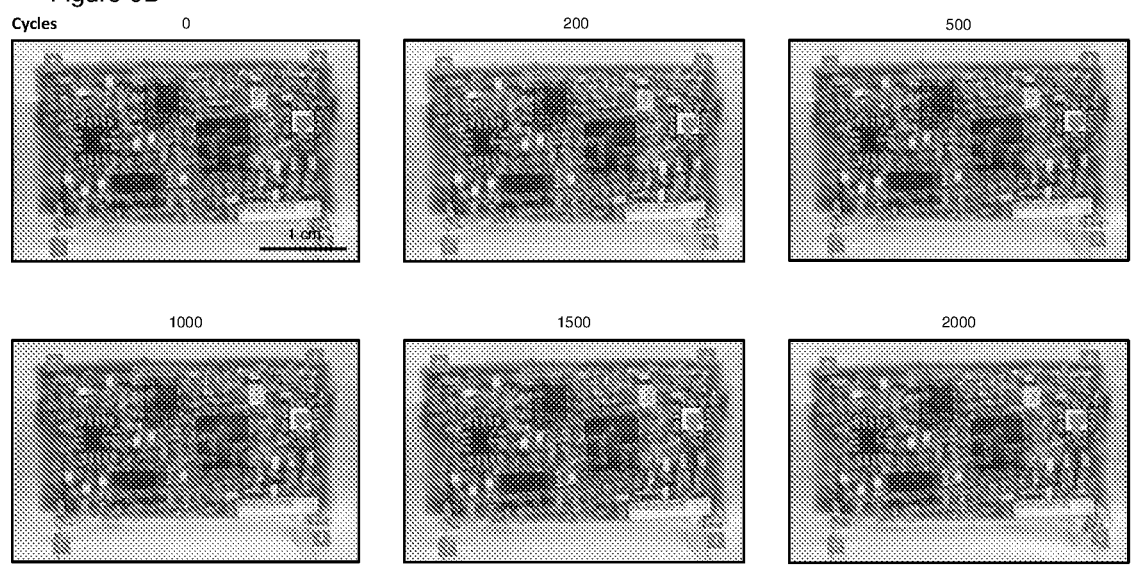
Figure 11A:
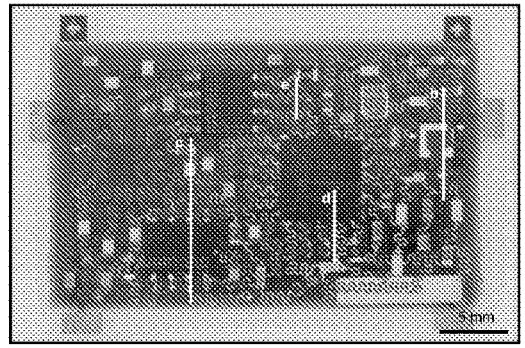
FIG. 11A shows an optical image of a three-dimensional integrated stretchable device and FIGS. 11B-11E show X-ray computed tomography (XCT) images illustrating the cross-sectional structure of the three-dimensional integrated stretchable device.
Figure 11B:
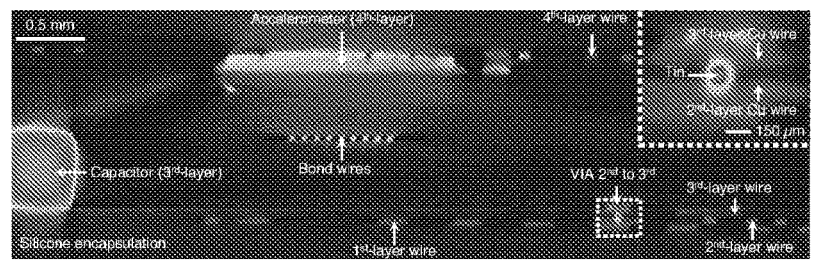
Figure 11C:
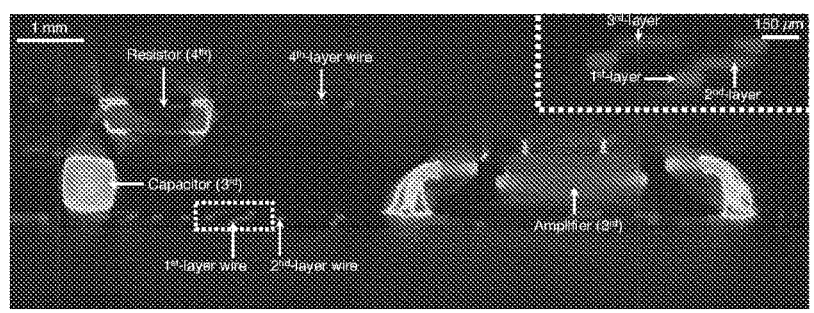
Figure 11D:
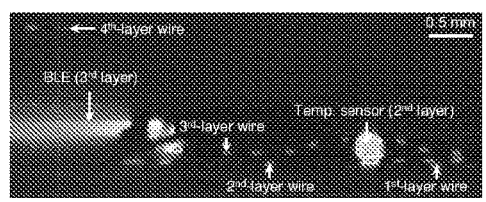
Figure 11E:
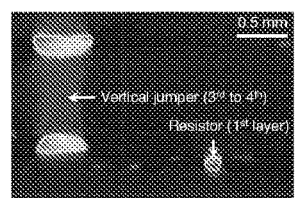

FIGS. 9A-9B show a fatigue test of the three-dimensional integrated stretchable device with 10% uniaxial strain at frequency of 0.5 Hz. (A) of FIG. 9 shows the setup for the cycling test. A customized electrically controlled stretcher is used to apply 10% uniaxial strain to the device. Two cables with minimal mechanical footprint provide connection to an external power supply to the device. Bluetooth signals transmitted from the device are used as an indicator to identify whether the device is damaged during cycling test. FIG. 9 in (B) shows images of the device after different numbers of cycles. The device remains functional after being cycled for more than 2000 times. The failure mechanism can possibly be the debonding of the components from the Cu pads or the breakage of the interconnects in some strain concentrated areas, which is still under active investigation.

FIGS. 10A-10E show experimental and finite element analysis (FEA) studies of the mechanical coupling between layers of the multilayered device. FIG. 10 in (A) is a schematic cross-section and top view of a representative part of interest in the multilayered device. (B) in FIG. 10 shows experimental and FEA results for the multilayered device with uniaxial strain from 0% to 75%. Due to the constraint from the rigid chips, the strain distribution is nonuniform, as shown from the FEA strain distribution ($\varepsilon_{max}$) for the device. With 75% strain, the serpentine interconnect was broken at the points of highly localized principal strain. (C) in FIG. 10 shows the overall stretchability as a function of the normalized serpentine-chip separation distance D/C. Stretchability is enhanced with increasing the separation distance when D/C<0.4 for the decreased mechanical coupling, and then tend to saturate when D/C>0.4. (D) in FIG. 10 shows experimental and FEA results for the multilayered device to show the decreased mechanical coupling between the layers by increasing the D/C. The interconnect strain distribution is nonuniform for low D/C (e.g., 0.06) and tend to be uniform for high D/C (>0.4). (E) in FIG. 10 show the overall stretchability as a function of normalized non-constrained interconnect length L/C. Stretchability is enhanced with increasing the non-constrained interconnect length when L/C<2.7, and then plateaus when L/C>2.7.

FIGS. 11A-11E show X-ray computed tomography (XCT) images illustrating the cross-sectional structure of the three-dimensional integrated stretchable device. (A) shows an optical image of the integrated device, with markers showing the cross-sectional positions corresponding to (B), (C), (D), and (E) in FIG. 11 show and label the key components and structures.

FIGS. 12A-12D show XCT images of a typical functional chip (i.e., the amplifier) and summarized dimensions of the packaged chip, polished chip, and bare die. (A) and (B) shows XCT images illustrating the amplifier structure in side and top views, respectively. It mainly contains the functional silicon bare die, Cu pins, bonding wires between the bare die and pins, and epoxy packaging (transparent in the XCT images). (C) and (D) summarize the width and thickness of the chip with packaging, after polishing, or only bare die. This information can provide design guidelines for using different types of components to build stretchable electronics for different purposes.

FIGS. 13A-13D show an evaluation of the effective laser beam size and depth of focus. (A) is a schematic illustration of the laser beam. There are two key parameters: the beam waist (w) and depth of focus (b). (B) shows a Cu foil on a 30° tilted surface to be processed using the laser with the pattern design shown in (C). According to the ablation results, shown in (D), and tilted angle degree, the laser beam waist and depth of focus can be calculated to be ~25 µm and ~600 µm, respectively.

Figure 14A:
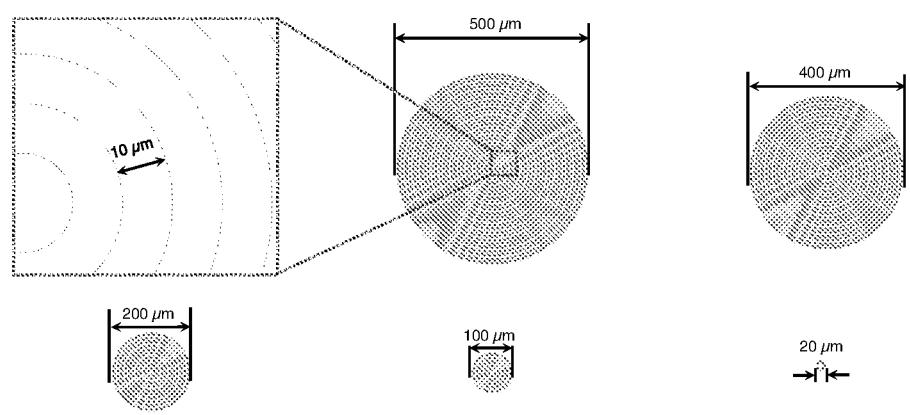
FIGS. 14A-14B show an evaluation of the laser fabricated VIA resolution in silicone.
Figure 14B:
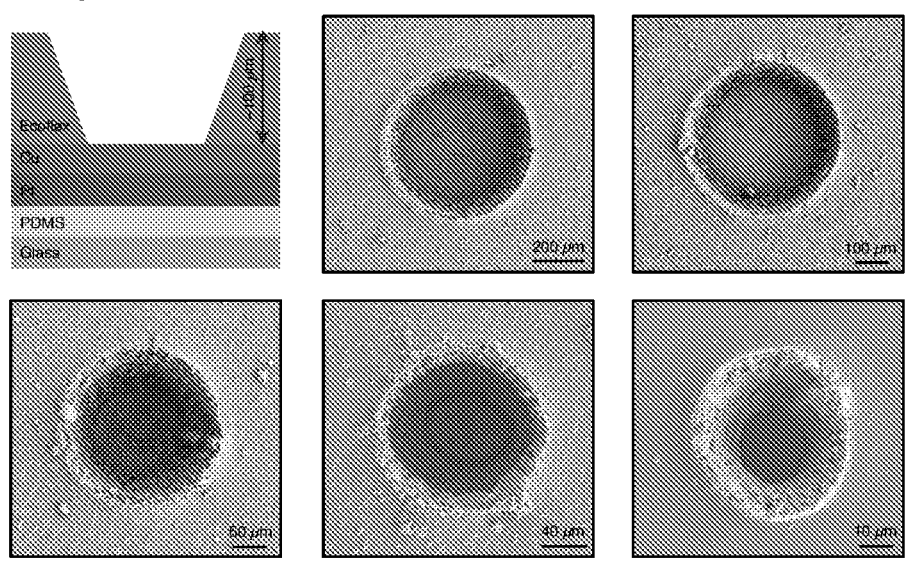

FIGS. 14A-14B show an evaluation of the laser fabricated VIA resolution in silicone. (A) shows the pattern design of the laser ablation with diameters from 500 µm to 20 µm. (B) shows selective ablation of silicone on the top of the Cu with the corresponding laser pattern shown in (A). The smallest diameter of VIA that can be fabricated on 100 µm thick silicone is ~45 µm, as shown in the lower right image in (B).

Figure 15:
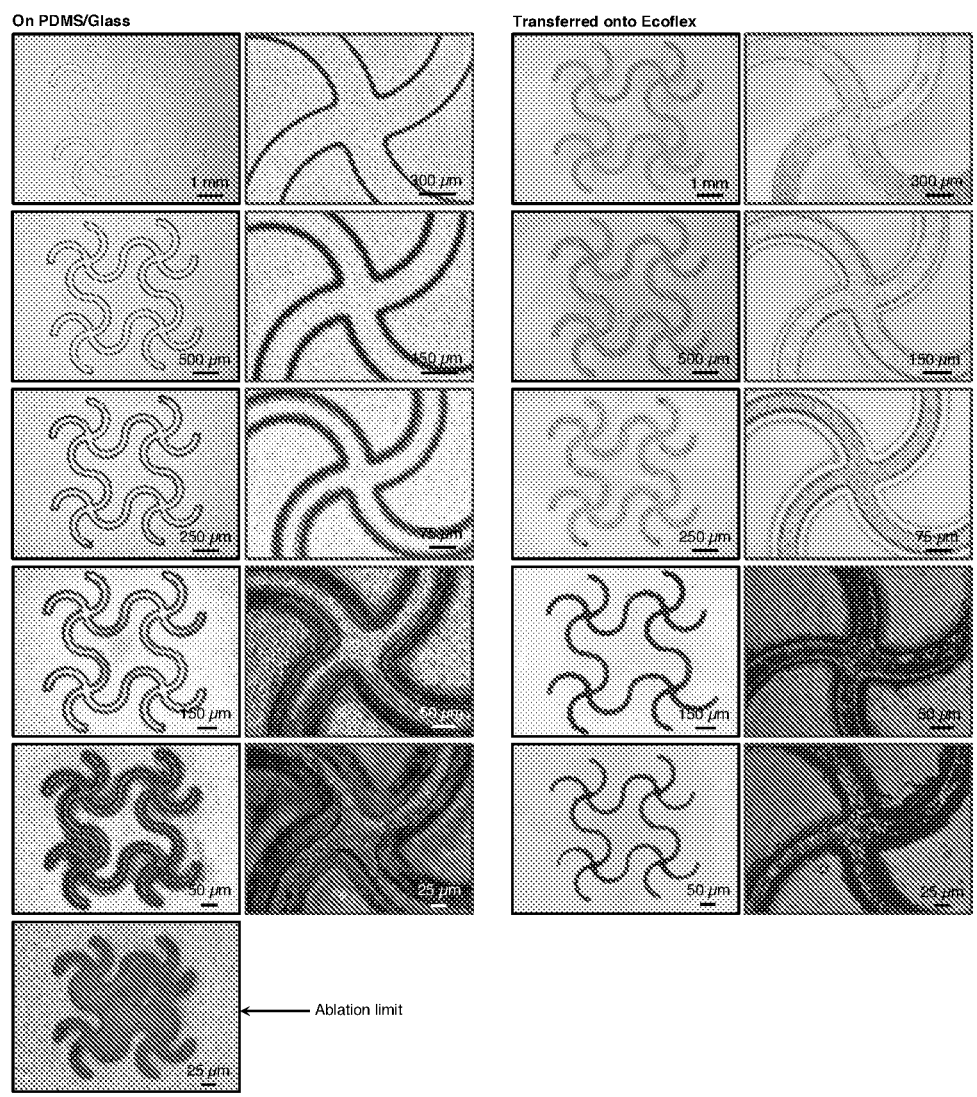
FIG. 15 shows an evaluation of pattern resolution of laser ablation in Cu/PI films.

FIG. 15 shows an evaluation of pattern resolution of laser ablation in Cu/PI films. Parameters of wavelength 1064 nm, pulse energy 0.42 mJ, and 10 cycles are used to write the serpentine pattern in the Cu/PI on the PDMS/glass substrate. Then the patterned Cu/PI electrodes are transferred onto the Ecoflex substrate with a water-soluble tape. The patterned electrodes, before transfer (left two columns) and after transfer (right two columns), with width ranging from 300 µm (first row) to 10 µm (second to the last row), are shown. For electrodes with width less than 10 µm, as shown in the last row, the PDMS substrate is not sticky enough to hold very thin electrodes that would be delaminated by the pressure waves from the laser ablation. The black color on the electrode is due to the thermal oxide on the Cu surface.

Figure 16:
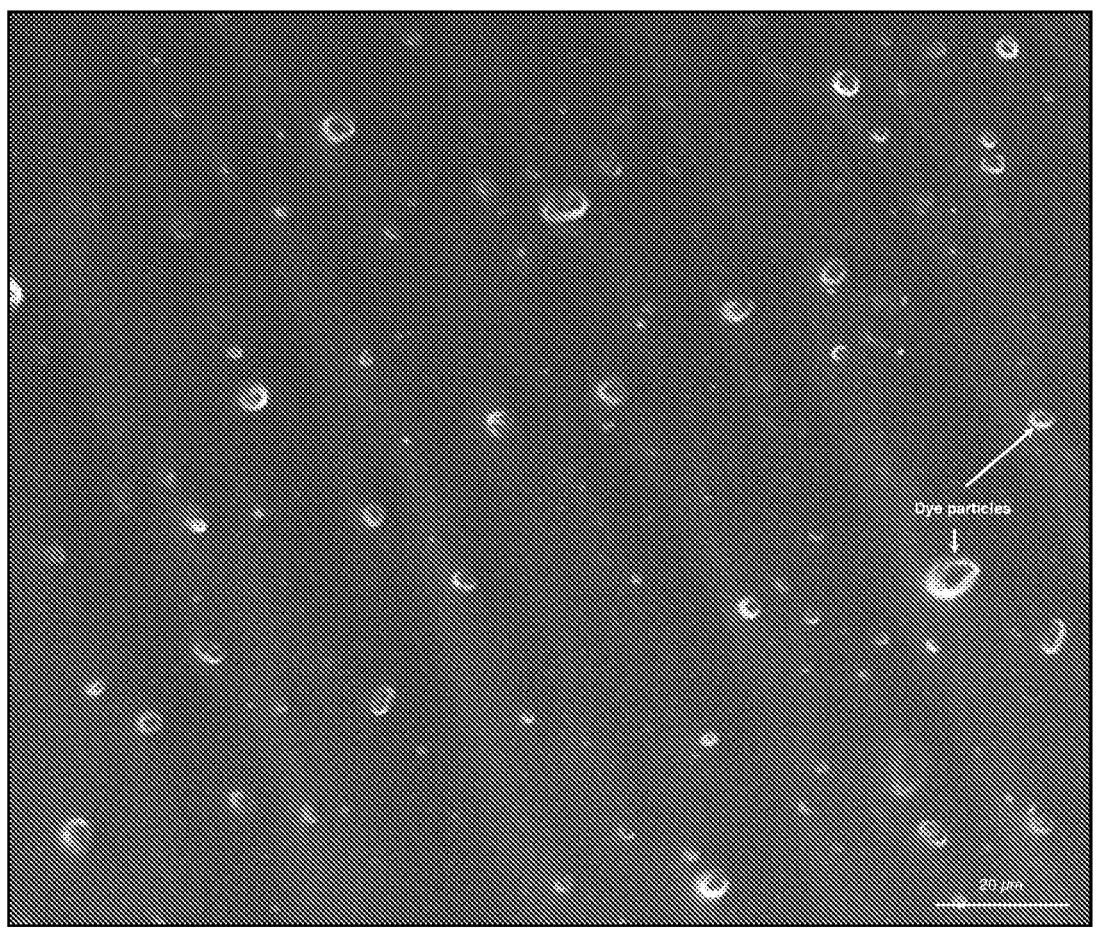
FIG. 16 is an SEM image of the silicone modified with 3% wt black dye.

FIG. 16 is an SEM image of the silicone modified with 3% wt black dye. The uniformly distributed small particles with diameters ranging from 2 to 5 µm can increase the light absorption of the silicone.

FIG. 17 shows the laser pulse energy controlled by the lens attenuation system. The Nd:YAG laser pulse energy is calibrated by an energy meter.

FIGS. 18A-18B show the ablation of different materials with laser wavelengths of (A) 532 nm and (B) 1064 nm. For 532 nm, laser ablation can be used to etch Cu, PI, and silicone without and with dye modifications. For 1064 nm, laser ablation is suitable to etch Cu, PI, and the silicone modified with only the black dye. Materials, whose critical attenuation is larger than Cu, can be selectively ablated in the presence of Cu.

Figure 19:
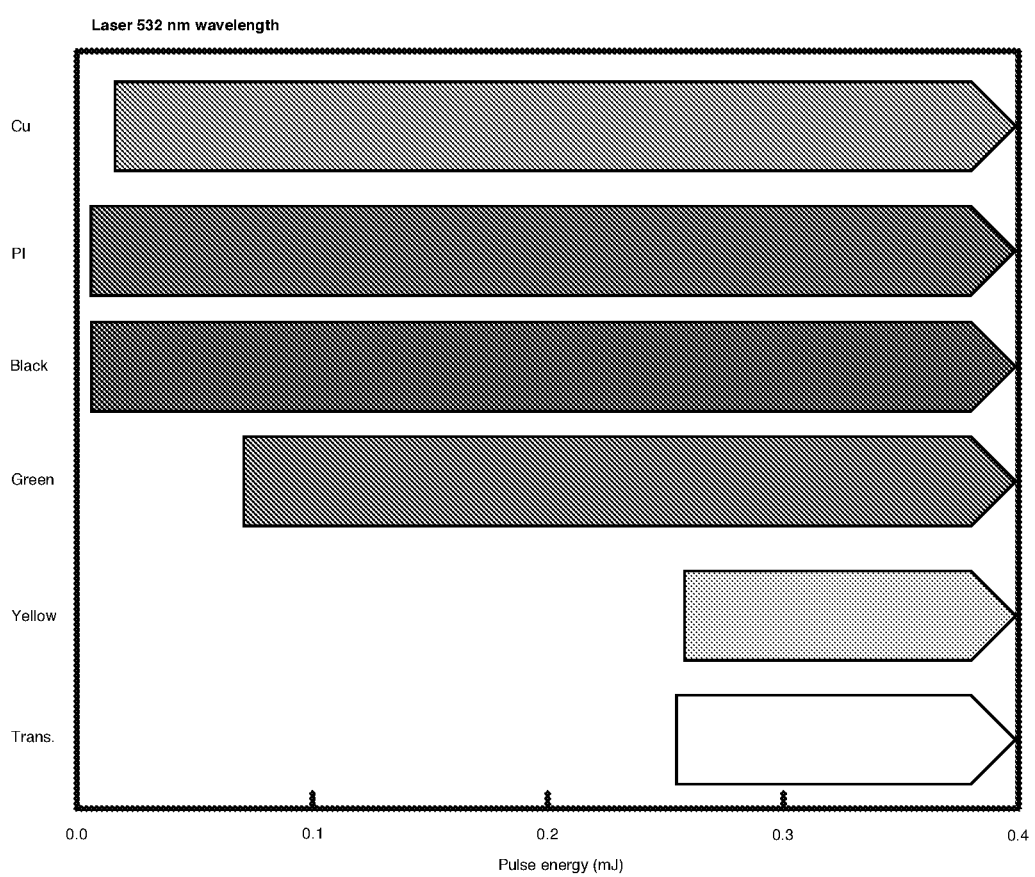
FIG. 19 shows the ablation pulse energy of laser with 532 nm wavelength light for Cu, PI, and silicone with different colors.

FIG. 19 shows the ablation pulse energy of laser with 532 nm wavelength light for Cu, PI, and silicone with different colors. The threshold pulse energies for Cu, PI, and black silicone are too close to allow selective ablation.

Figure 20A:
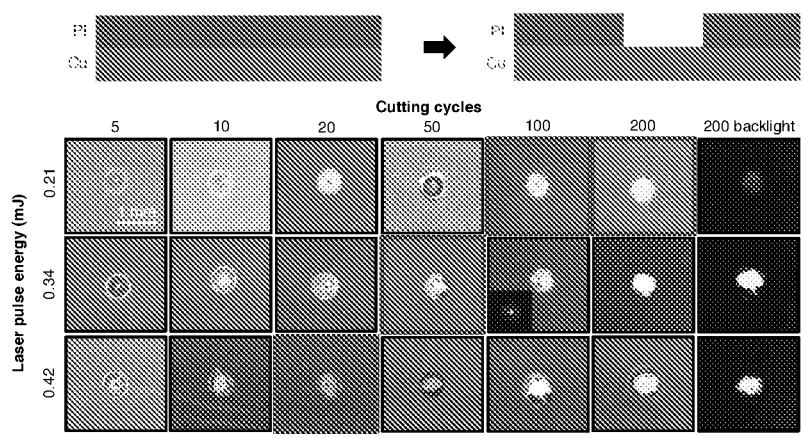
FIGS. 20A-20B show the selective laser ablation of Cu and PI.
Figure 20B:
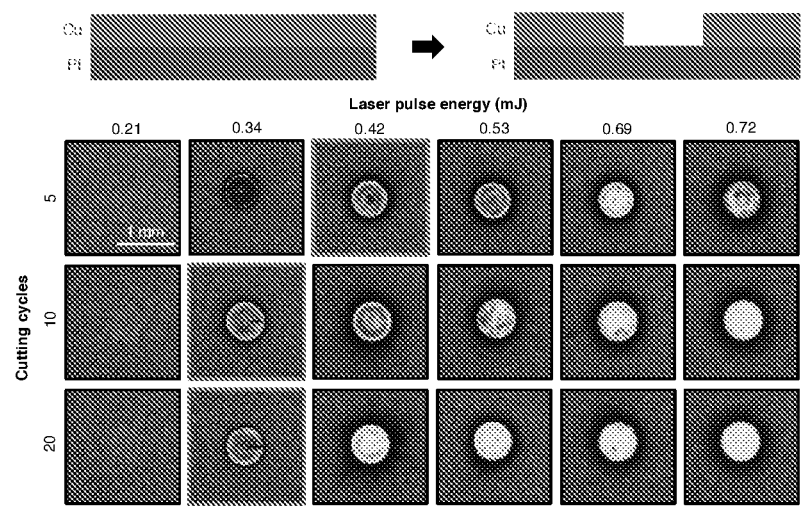

FIGS. 20A-20B show the selective laser ablation of Cu (~20 µm) and PI (~14 µm). Laser (1064 nm) with different pulse energies or ablation cycles is used to selectively remove PI on Cu (a) or Cu on PI (b). As the critical pulse energy for PI (0.05 mJ) is lower than Cu (0.34 mJ), it's easy to selectively remove PI from the bottom Cu by controlling the laser pulse energy at 0.21 mJ. No matter how many processing cycles are used, the bottom Cu is still safe, as shown in the first row of (A). To remove Cu from PI is very difficult, but can be achieved by controlling the processing cycles. If more cycles are used, the bottom PI will also be ablated, as shown in (B).

Figure 21A:
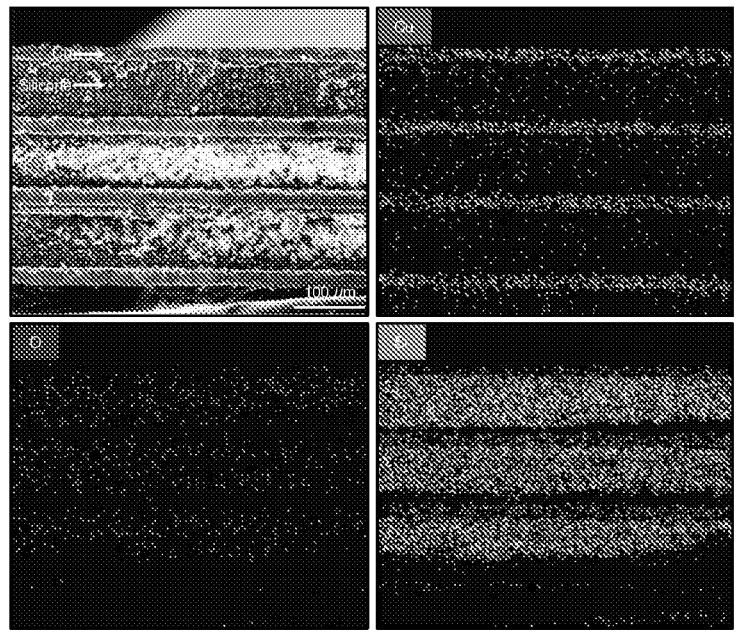
FIGS. 21A-21B show a multilayer Cu insulated by soft silicone to fabricate the VIAs.
Figure 21B:
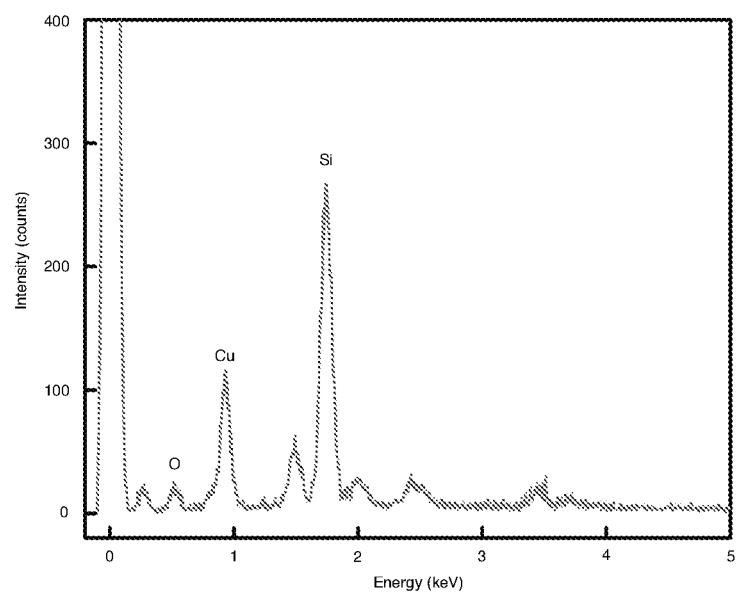

FIGS. 21A-21B show a multilayer Cu insulated by soft silicone to fabricate the VIAs. (A) shows a SEM image and corresponding EDS mapping graphs of the multilayer structure. (B) shows an EDS spectrum of the elements included in the sample.

Figure 22A:
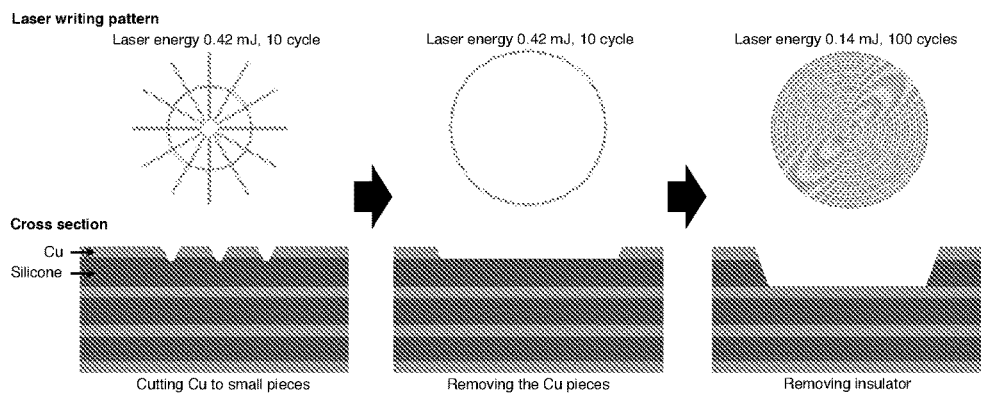
FIGS. 22A-22C illustrate the design of a laser ablation process for selectively ablating Cu and black silicone to build a through VIA.
Figure 22B:
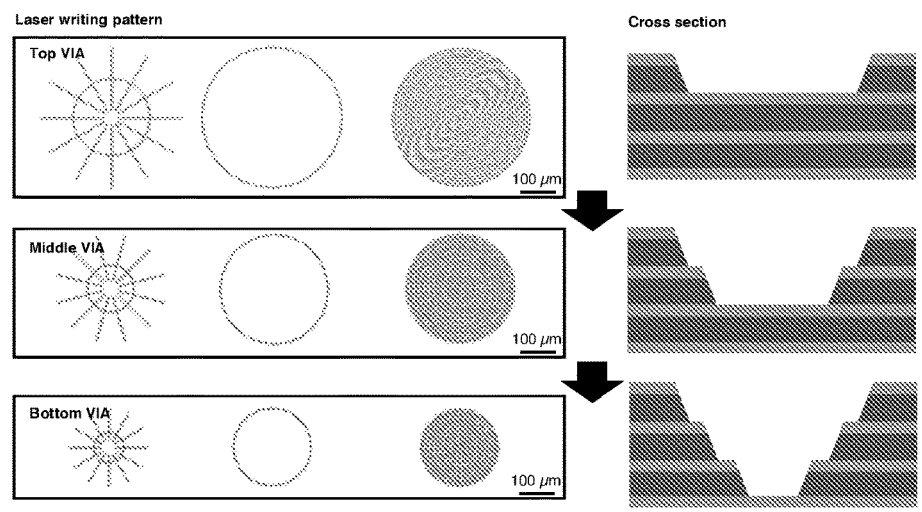
Figure 22C:

FIGS. 22A-22C illustrate the design of a laser (operating at 1064 nm) ablation process for selectively ablating Cu and black silicone to build a through VIA. (A) shows a laser cutting pattern design (top row) and corresponding schematics showing the ablation results (bottom row). With the first pattern, Cu will be cut into small pieces. With the second pattern, Cu will delaminate from the silicone substrate automatically, due to the thermal residual stress. (B) shows serial pattern designs to build the through VIA. (C) shows schematics (left) and a SEM image (right) of the through VIA.

Figure 23:
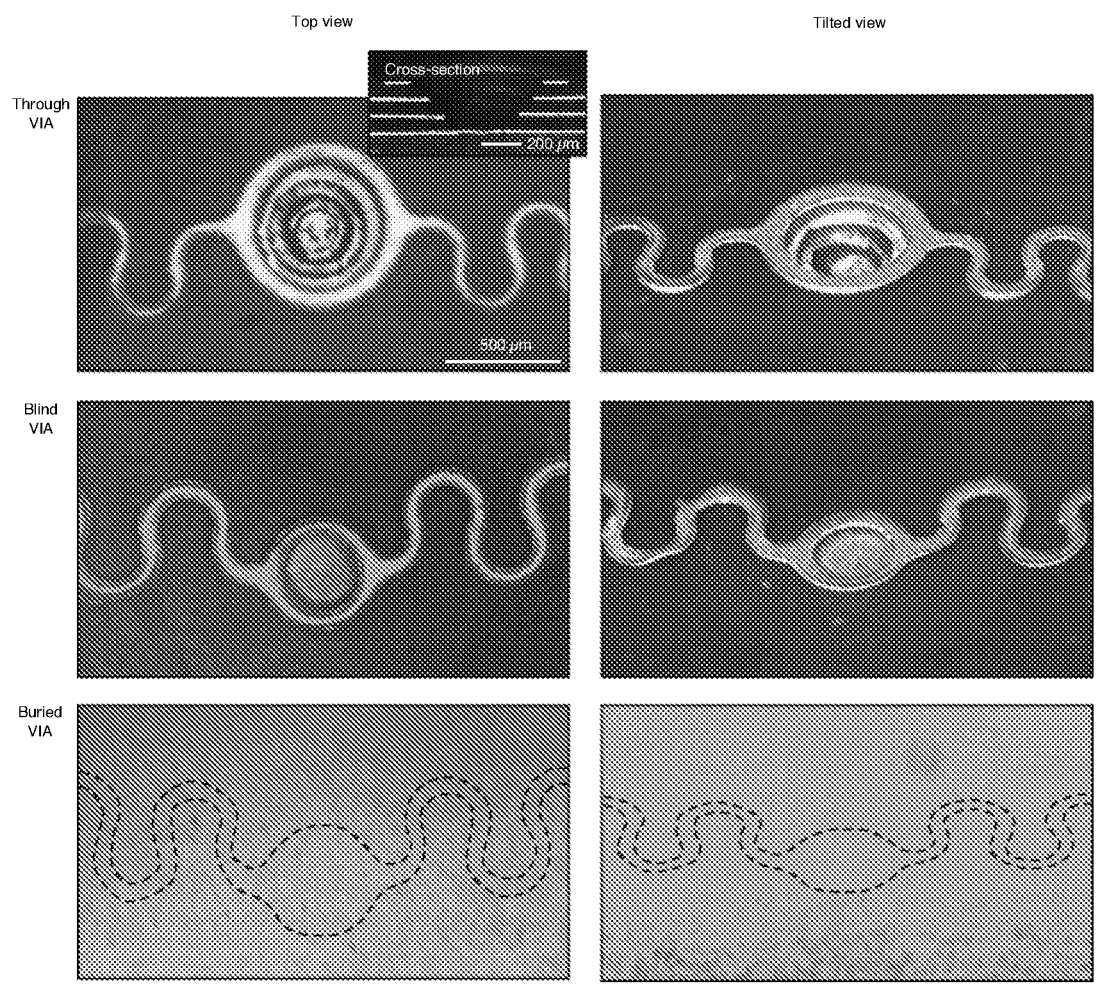
FIG. 23 shows images of all three types of VIAs.

FIG. 23 shows images of all three types of VIAs. Optical images show the top view and tilted view of the VIAs. All images share the same scale bar. The inset figure shows the cross-section of the through VIA.

Figure 24A:
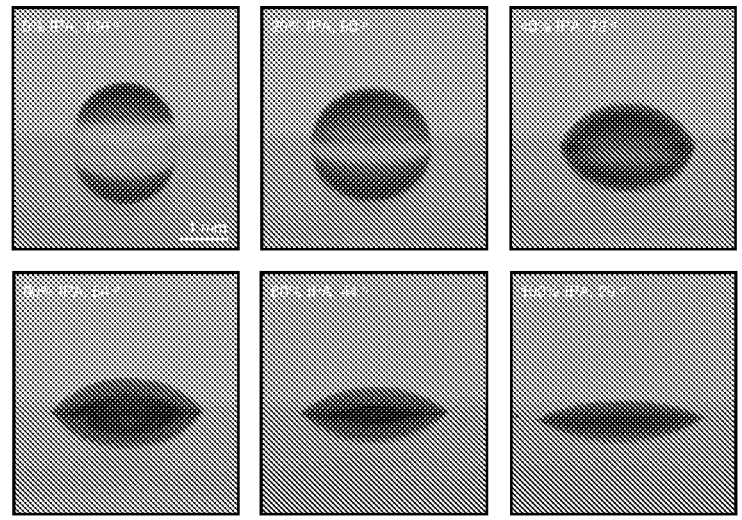
FIGS. 24A-24B illustrate control of the contact angle of flux (aqueous solution) with silicone (black Ecoflex) by mixing with IPA.
Figure 24B:
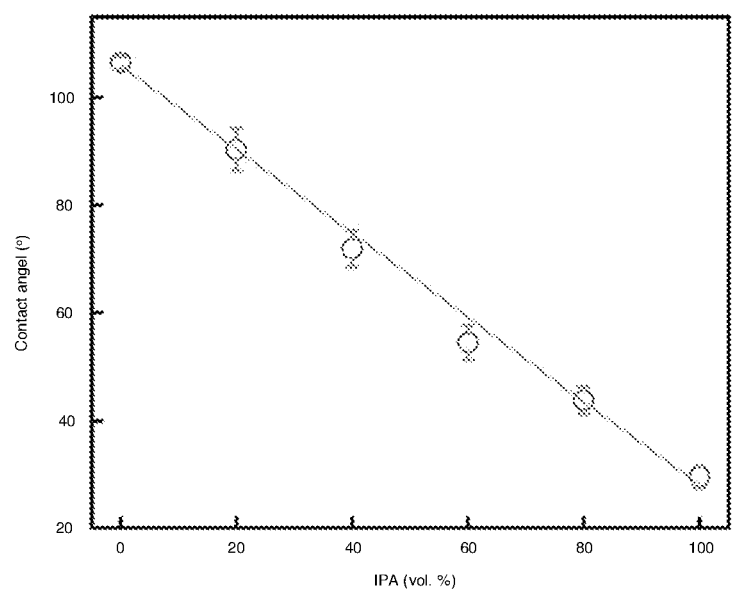

FIGS. 24A-24B illustrates control of the contact angle of flux (aqueous solution) with silicone (black Ecoflex) by mixing with IPA. (A) shows images illustrating the contact angle of flux mixed with IPA of volume percentile from 0% to 100%. All images share the same scale bar. (B) shows the linear relationship between the contact angle and IPA volume percentile.

Figure 25A:
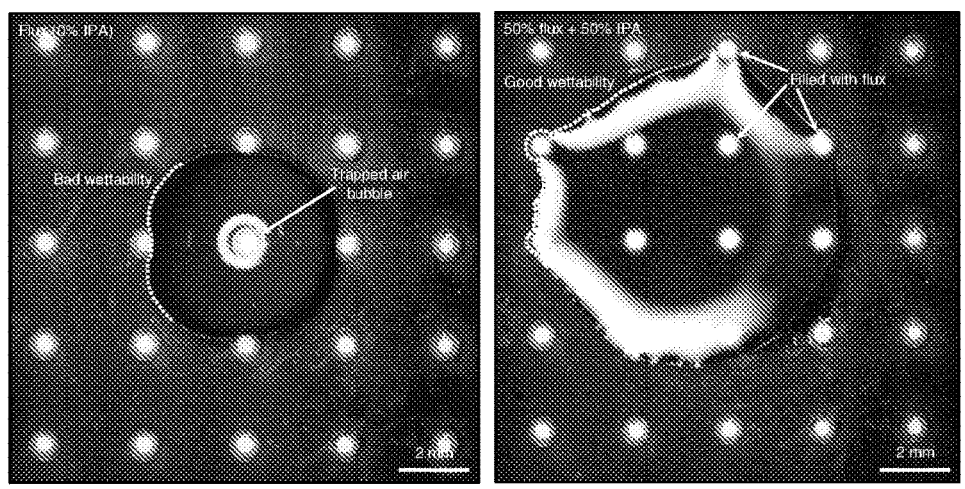
FIGS. 25A-25B are a comparison of the VIA surface with and without Cu oxide by flux.
Figure 25B:
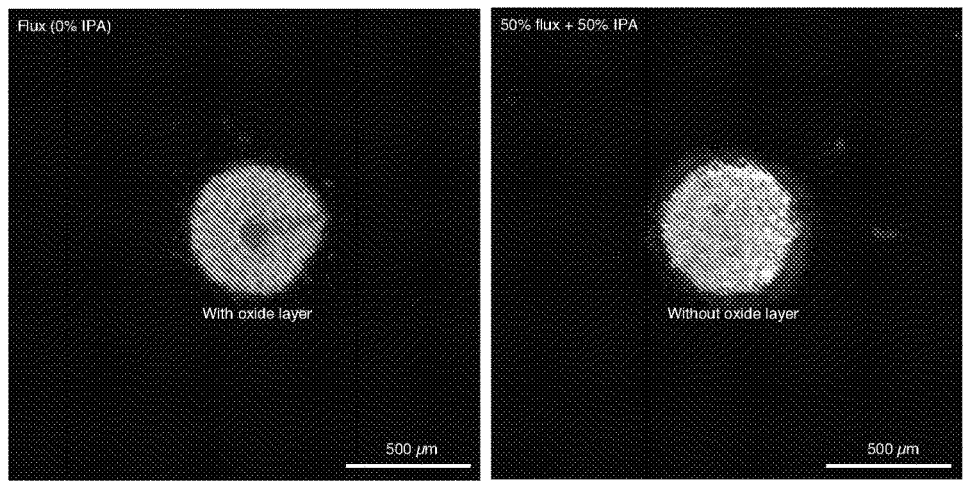

FIGS. 25A-25B are comparisons of the VIA surface with and without Cu oxide by flux. (A) shows the wettability of flux only (left) and 50% flux+50% IPA (right). The flux cannot go into the VIAs due to its large contact angle with silicone. With 50% IPA, the contact angle decreases, which improves the wettability on silicone. Each droplet volume is ~80 μL. (B) is a comparison of cleaned Cu surfaces with flux only (left) and 50% flux+50% IPA (right).

Figure 26A:
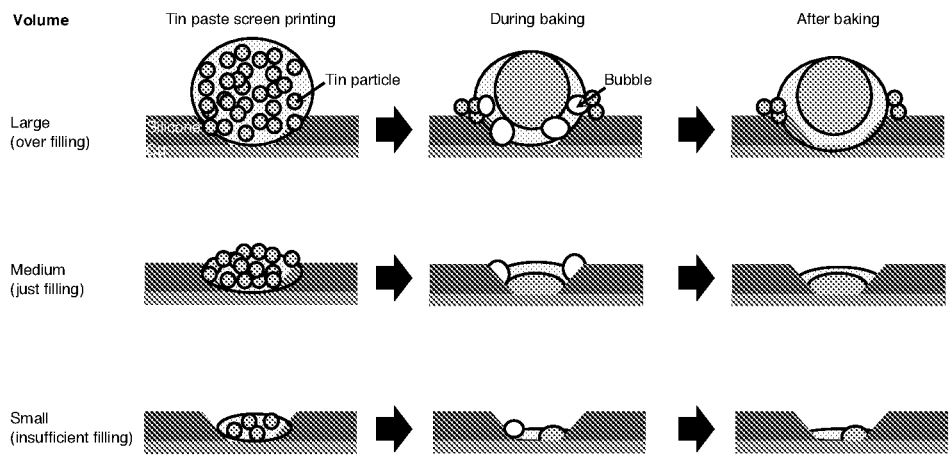
FIGS. 26A-26B is a schematic illustration of curing the tin paste with different amounts of paste by screen-printing.
Figure 26B:
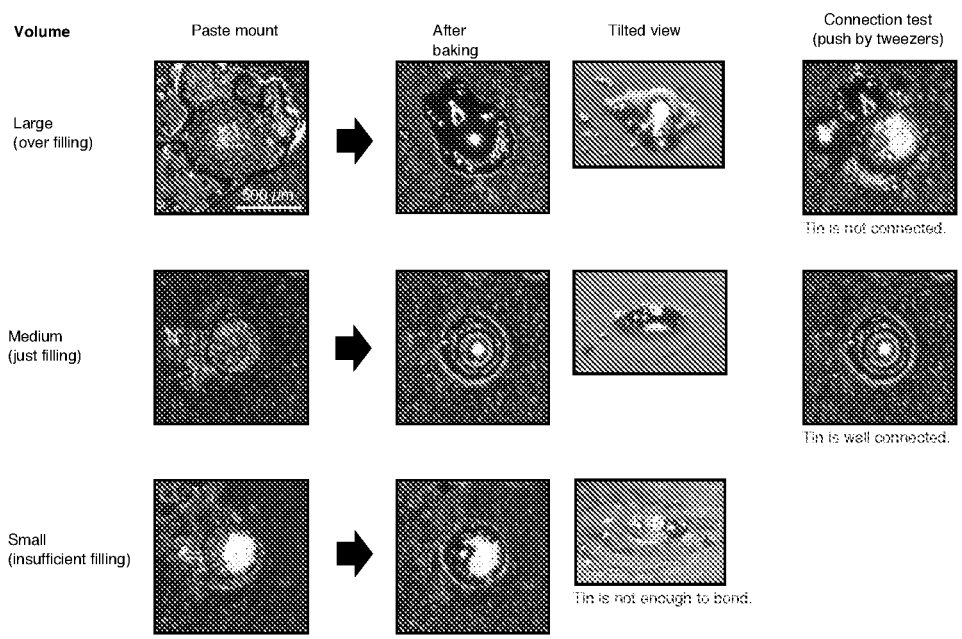
Figure 29A:
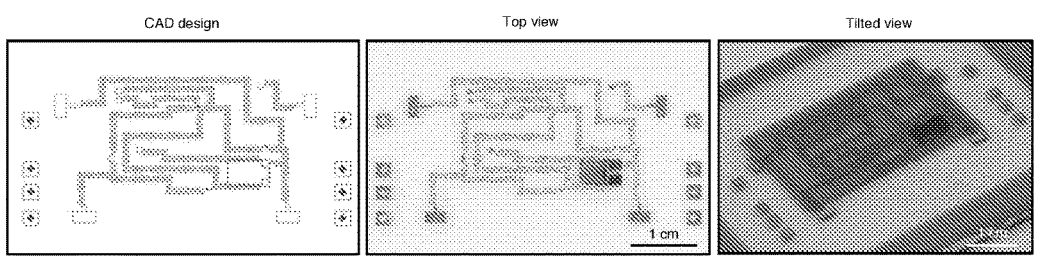
FIGS. 29A-29D illustrate the layer by layer fabrication process for the four-layer stretchable system.
Figure 29B:
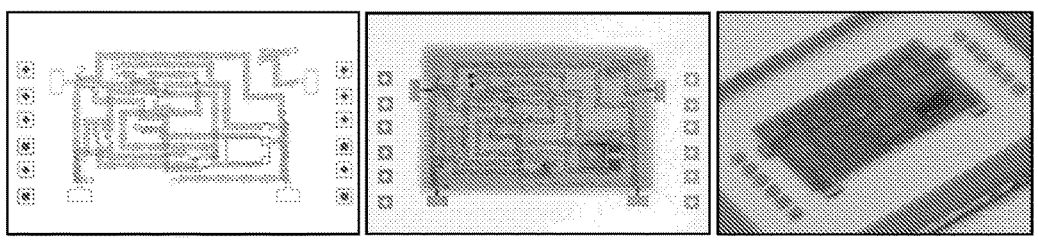
Figure 29C:
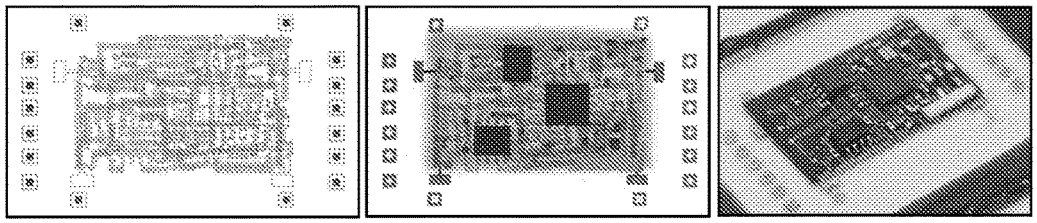
Figure 29D:
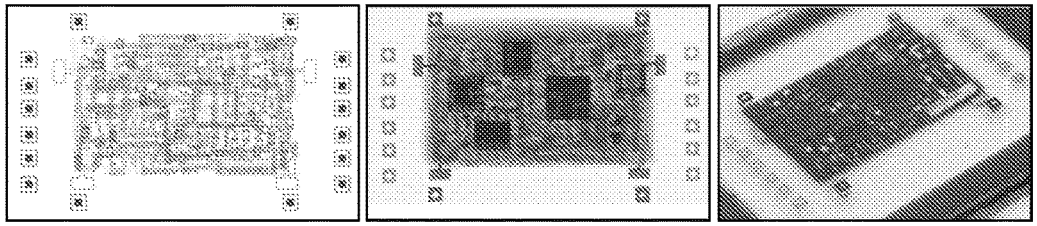
Figure 30A:
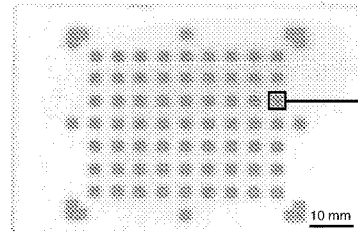
FIGS. 30A-30F show an evaluation of interconnection distortion during the transfer printing process.
Figure 30B:
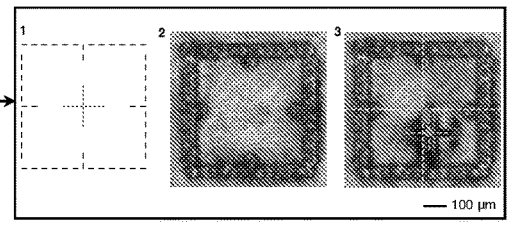
Figure 30C:
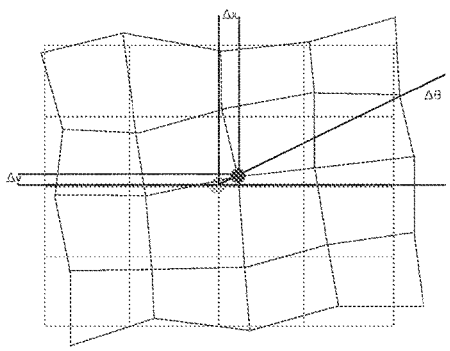
Figure 30D:
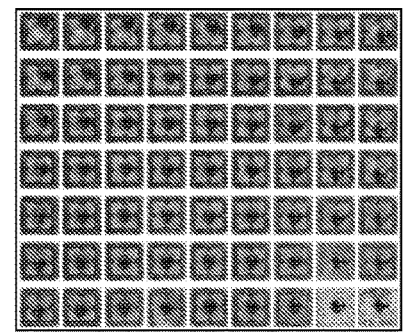
Figure 30E:
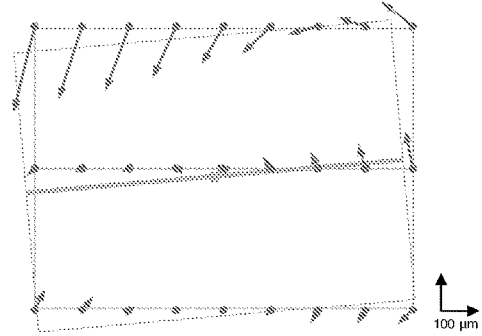
Figure 30F:
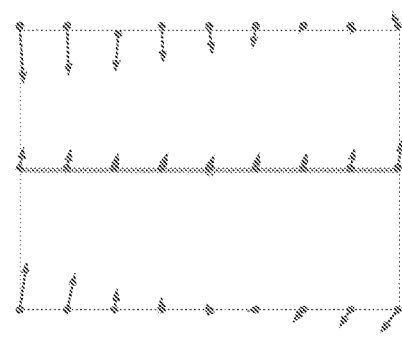

FIGS. 26A-26B are schematic illustrations of curing the tin paste with different amounts of paste by screen-printing. (A) illustrates that during baking, small tin particles will melt and merge to form big tin balls. At the same time, the flux will boil and generate some bubbles. If there is too much paste, the flux will generate too many bubbles that will push the tin ball to separate from the bottom Cu. On the other hand, if the paste amount is not enough, it will not be able to cover the entire bottom Cu pad surface. Therefore, suitable amount of paste is necessary to form robust and reliable bonding with the exposed Cu pads. (B) shows experimental results illustrating the bonding behavior. All images share the same scale bar.

FIGS. 27A-27C illustrates the 10-layer stretchable decagram device structure. (A) is a schematic top view (left) and cross sectional view (right) showing the multilayered device structure. The device has 10 layers, with a heater in each layer and a VIA vertically connecting the adjacent layers in series. The entire device is fully encapsulated by silicone. (B) shows the detailed schematics and (C) shows optical images of the heater (left) and VIA (right).

FIGS. 28A-28C illustrate the thermal imaging setup for the 10-layer stretchable decagram device. (A) is a schematic top and cross sectional views of the setup. An external DC supply is used to drive the device. An IR camera (ThermApp® TH, resolution 384×288 pixels, sensitivity <0.07 K) is used to image the temperature distribution on the device surface. A steel board at the bottom is used as the heat sink to increase the thermal dissipation of the device. An antireflective layer (a white paper or black plastic) is used to decrease the IR reflection from the environment. (B) shows thermal images of the device with different heating power. (C) is a temperature summary of heaters in different layers.

FIGS. 29A-29D illustrate the layer by layer fabrication process for the four-layer stretchable system. The images show the fabrication process from the (A) $1^{st}$ layer to the (D) $4^{th}$ layer, in CAD design (first column), device top view (second column), and device titled view (third column).

FIGS. 30A-30E show an evaluation of interconnection distortion during the transfer printing process. (A) shows an overview of a test sample. B(1) shows the alignment marker design, black line for $1^{st}$ ablation (before transfer) and red line for $2^{nd}$ ablation (after transfer); Examples of actual laser marker are shown in B(2) before transfer and in B(3) after transfer. (C) shows the schematic laser alignment error (with horizontal shift Δx, vertical shift Δy, and rotation Δθ) and sample distortion after transfer. (D) is a compiled photo of alignment markers at each location. The arrows in (E) show the total misalignment between the $1^{st}$ and $2^{nd}$ laser ablation patterns, which include both the laser alignment error and transfer distortion. By calculation, the location discrepancies and laser alignment error are Δx, Δy, Δθ: −29 μm, −24 μm, 0.14°, respectively. (F) shows the transfer distortion, regardless of the laser alignment. (Maximum distortion: 152 μm, Average distortion in rms: 14 μm).

FIGS. 31A-31B show the setup for aligned transfer printing. The multilayered device is fabricated layer by layer. The subsequent layer should be well-aligned with the existing layers for VIA connections. (A) is a schematic illustration of the alignment. Every layer has the marker for alignment. The layer to be transferred is on water soluble tape and fixed by PDMS temporarily. (B) shows the alignment system, composed of a microscope and a mechanical stage. The first layer is fixed on a transparent holder and the second layer is placed on a 5 mm thick Ecoflex. The Ecoflex is used as the buffer for soft contact with the first layer, which will protect the sample from excessive pressure.

Figure 32A:
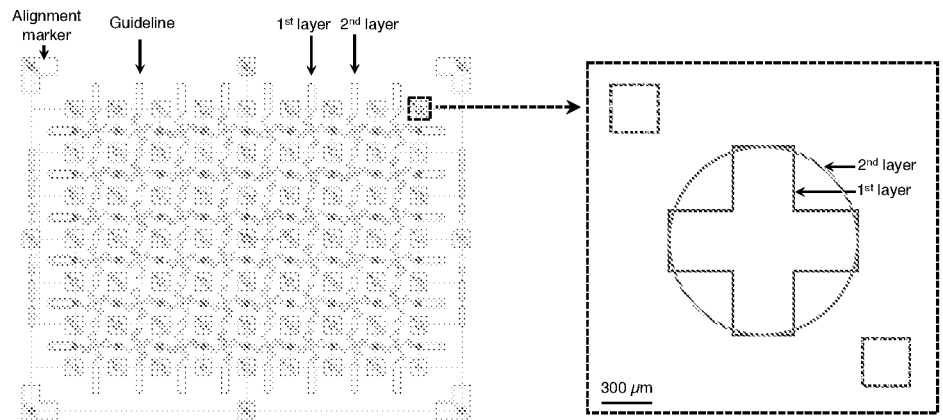
FIGS. 32A-32C illustrate the evaluation of the error in the aligned transfer printing process.
Figure 32B:
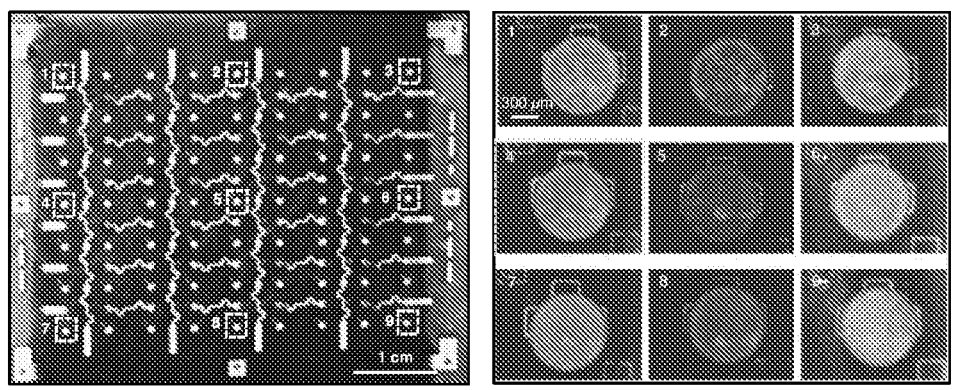
Figure 32C:
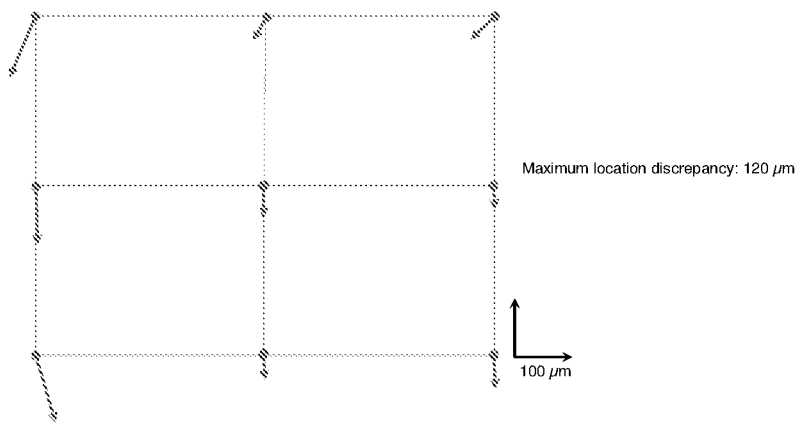

FIGS. 32A-32C illustrate the evaluation of the error in the aligned transfer printing process. (A) shows a two-layer pattern design for the transfer error evaluation. Shown on the right is the ideal alignment of the markers. (B) The integrated two-layer device after transfer printing. Shown on the right are the marker distribution on the device. After checking the marker shift, the aligned transfer printing error is evaluated, as shown in (C). The maximum error is ~120 μm.

Figure 33A:
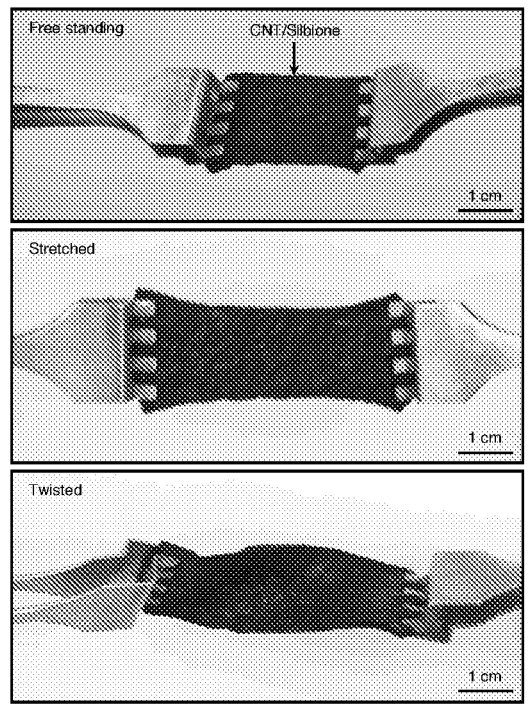
FIGS. 33A-33B demonstrate the mechanical properties of the soft CNT/Silbione EP sensors.
Figure 33B:
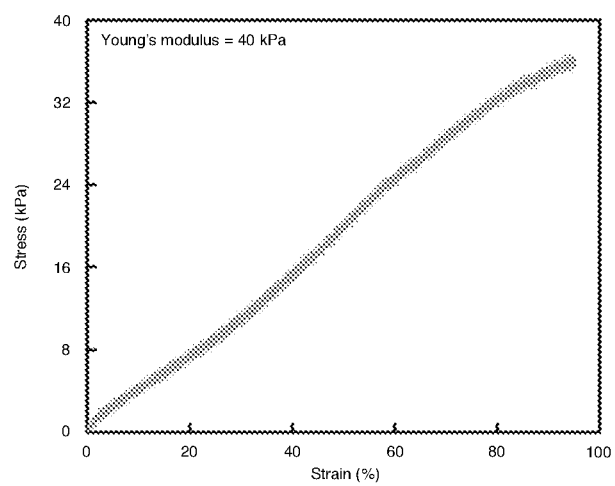

FIGS. 33A-33B demonstrate the mechanical properties of the soft CNT/Silbione EP sensors. (A) presents optical images showing the sensor can be stretched and twisted. (B) shows the stress vs. strain relationship of the EP sensor indicating its ultra-low Young's modulus of 40 kPa.

Figure 34A:
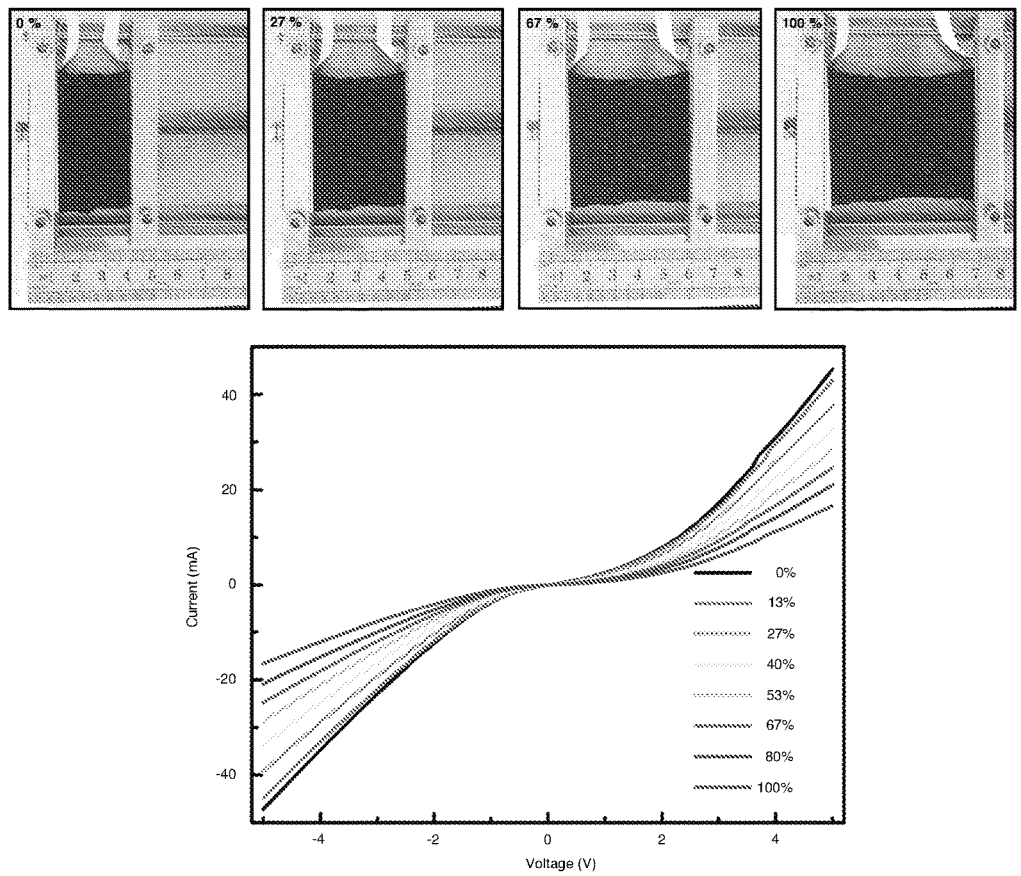
FIGS. 34A-34B demonstrate the electrical properties of the soft CNT/Silbione EP sensors.
Figure 34B:
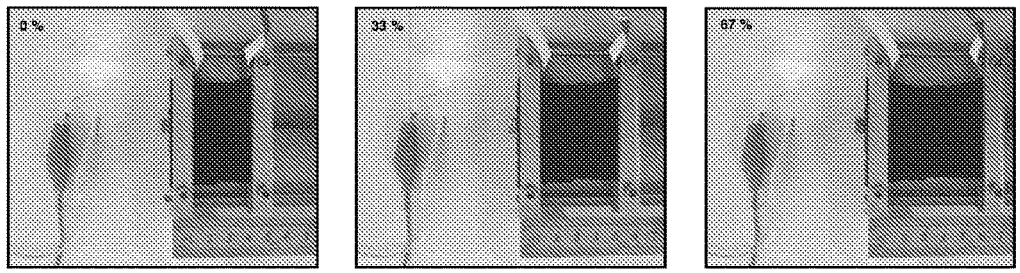
Figure 35A:
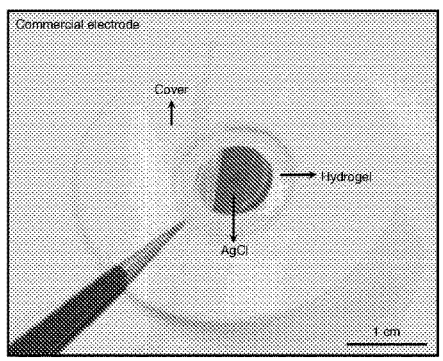
FIGS. 35A-35B show commercial electrodes and homemade soft CNT/Silbione electrodes, respectively.
Figure 35B:
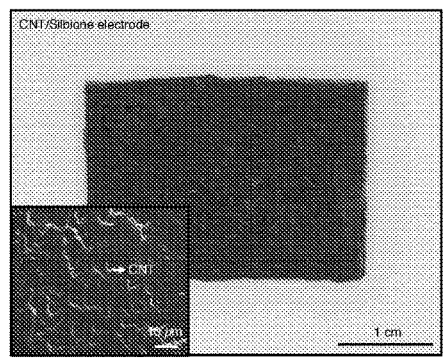
Figure 35C:
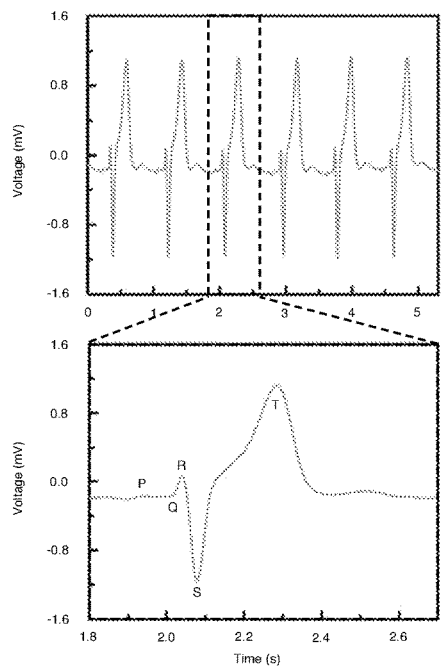
FIGS. 35C-35D shows ECG signals from the electrodes.
Figure 35D:
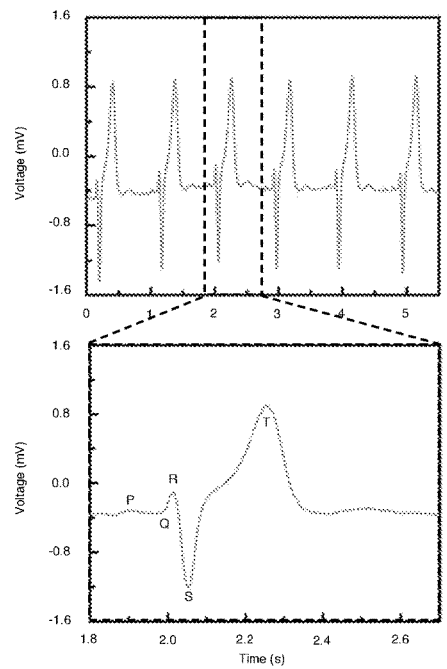

FIGS. 34A-34B demonstrate the electrical properties of the soft CNT/Silbione EP sensors. (A) presents optical images of the sensor (with dimensions ~30×56×1 (L×W×T) $mm^3$) under different levels of uniaxial strain and associated I-V curves. (B) shows that the sensor itself can be used as a stretchable electrical connection to light up a LED at 3 V.

FIGS. 35A-35D show ECG signals acquired with fresh commercial electrodes and homemade soft CNT/Silbione electrodes. The similar results of these two types of electrodes with high signal-to-noise-ratios (SNR) and the well defined P, Q, R, S, and T waveforms indicate the excellent sensing capability of the soft EP sensors. Optical images of (A) the commercial AgCl/Ag-hydrogel electrode and (B) soft CNT/Silbione electrode, respectively. The inset of (B) shows the magnified CNT/Silbione composites in SEM. ECG signals acquired from the chest with (C) the commercial and (D) CNT/Silbione electrodes, respectively.

Figure 36A:
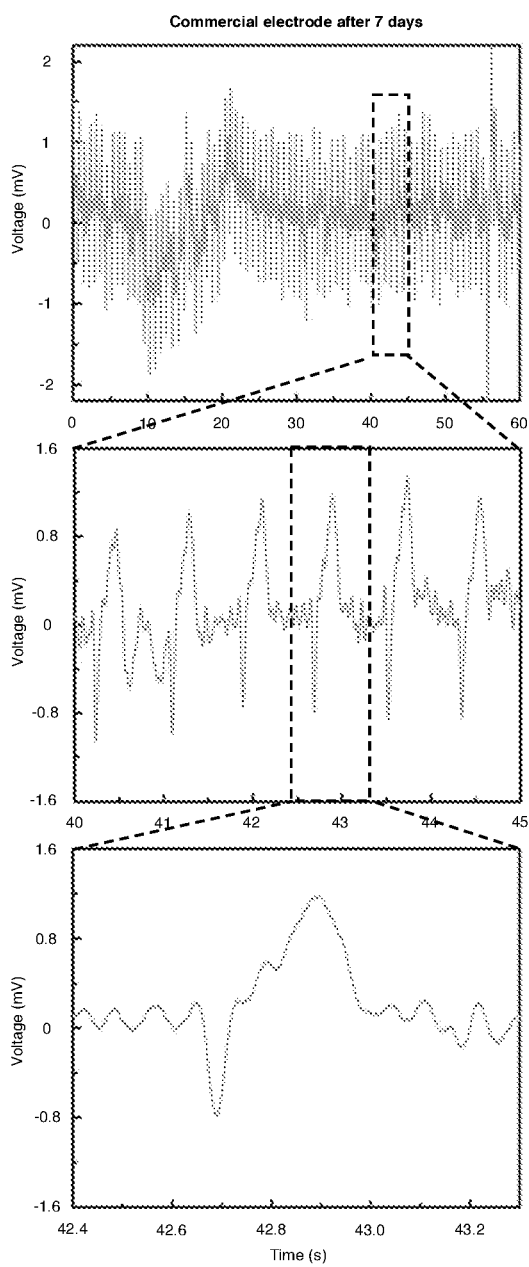
FIGS. 36A-36B compare the durability between the commercial electrode and a soft CNT/Silbione electrode.
Figure 36B:
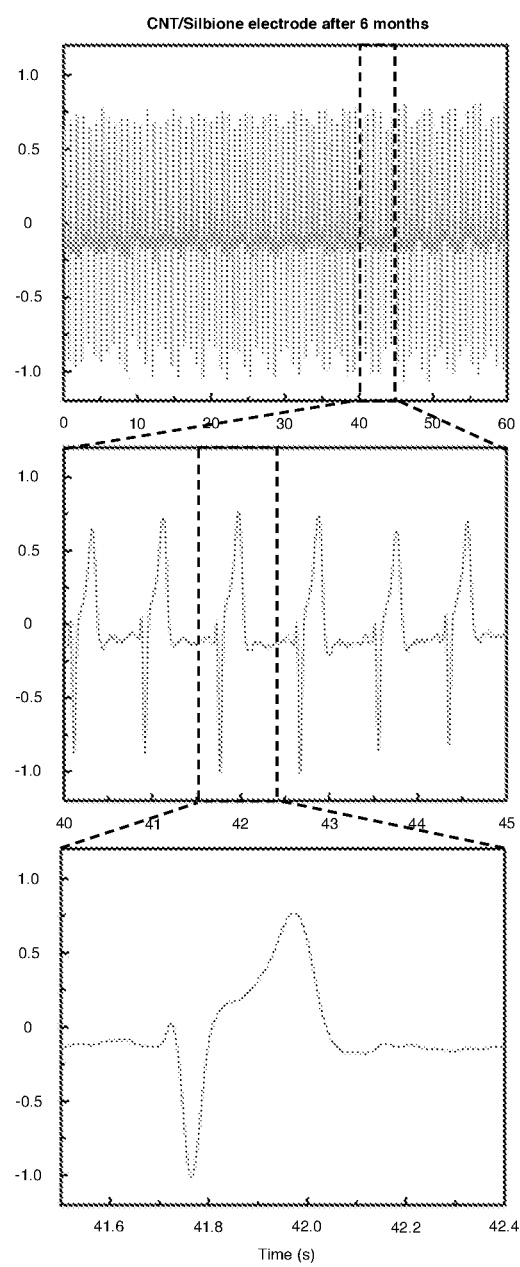

FIGS. 36A-36B compare the durability between the commercial electrode and the soft CNT/Silbione electrode described herein. (A) shows the ECG signals acquired by the commercial electrode, which has been exposed in air for 7 days with the plastic covers removed. The fluctuating and noisy signals are due to the hydrogel that is dried out when exposed in air, which increases the impedance between the electrode and the skin. (B) shows the stable ECG signals acquired by the CNT/Silbione electrode, which has been exposed in air for around 6 months, showing the electrode's superb durability.

Figure 37:
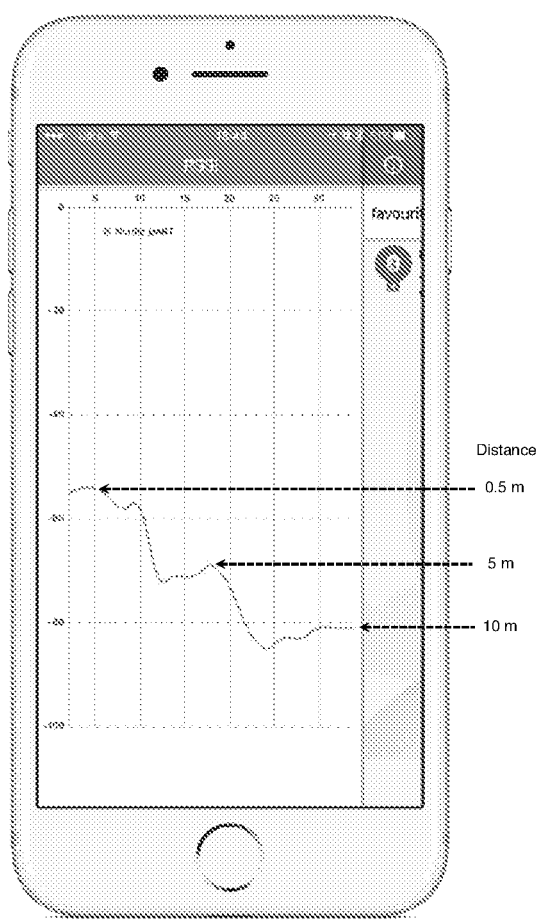
FIG. 37 shows test results of the Bluetooth signal strength from the multilayered stretchable device by the received-signal-strength-indicator (RSSI).

FIG. 37 shows test results of the Bluetooth signal strength from the multilayered stretchable device by the received-signal-strength-indicator (RSSI). The measurement hardware is a smartphone (iPhone 6 Plus with software NRF Connect).

FIG. 38 is a summary of the circuit design for the multilayered stretchable system. There are six primary parts: strain gauge, electrophysiological potential sensor, temperature sensor, two-channel posture sensor, three-channel acceleration sensor, and the Bluetooth. Low power medical instrumentation amplifiers (AD627B) are used to amplify signals for the strain and EP sensors. A matching circuit is designed to adjust the impedance of the Bluetooth to match the 2.4 GHz antenna impedance (50 Ohm), which helps increase the Bluetooth signal strength.

Figure 39:
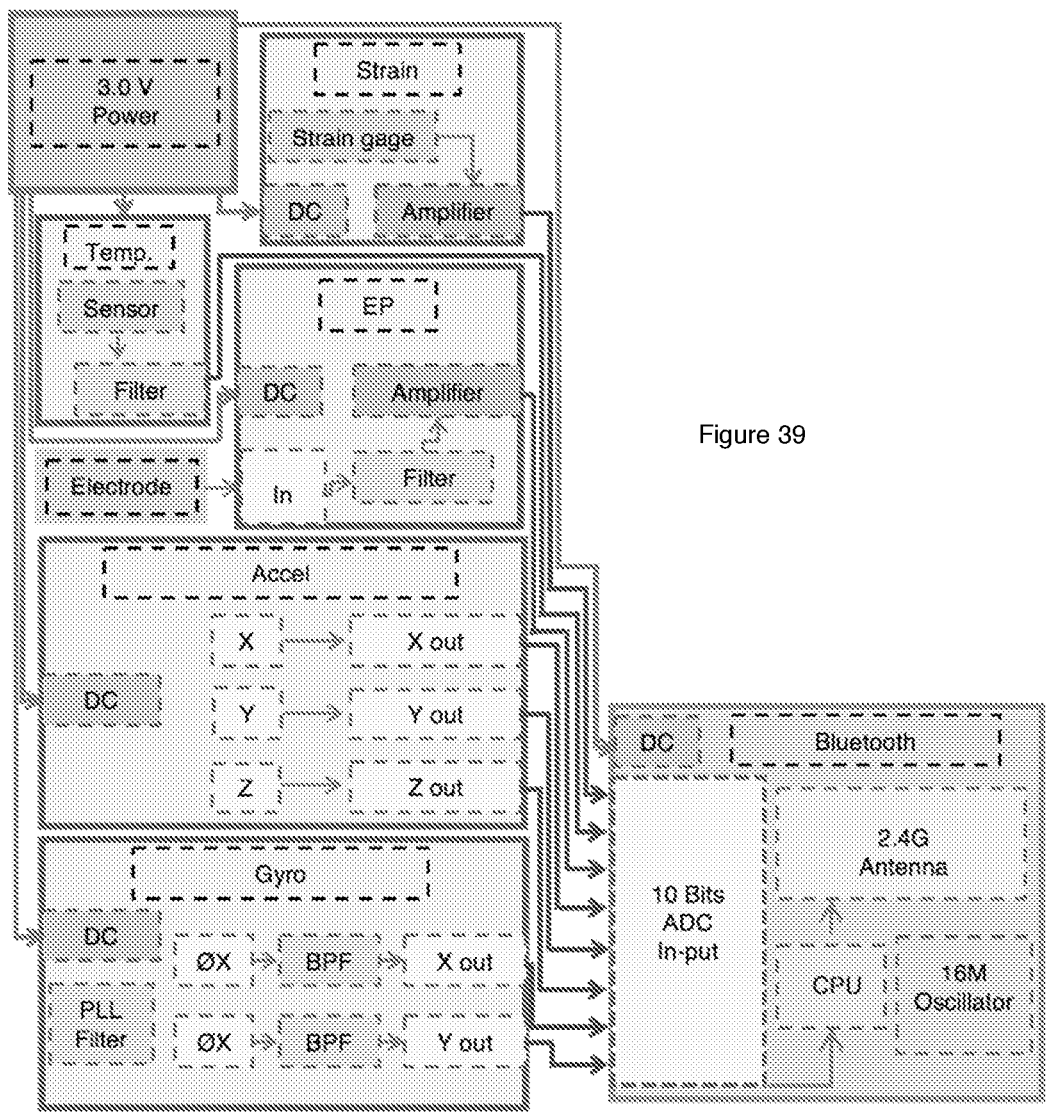
FIG. 39 is a flow diagram showing signal transmission through the multifunctional device.
Figure 41A:
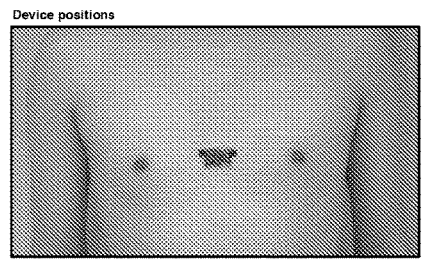
FIGS. 41A-41B shows the multilayered device located on different parts of the body and FIGS. 41C-41D shows ECG signals acquired from different positions of the human body.
Figure 41B:
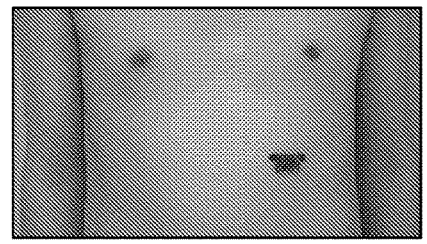
Figure 41C:
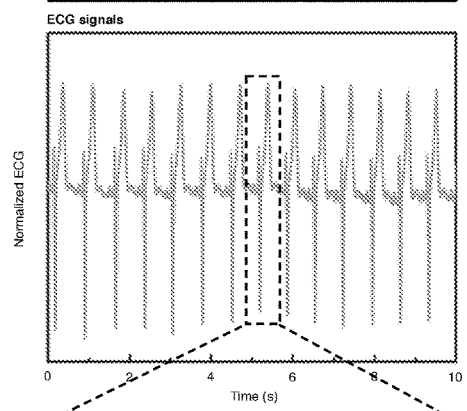
Figure 41D:
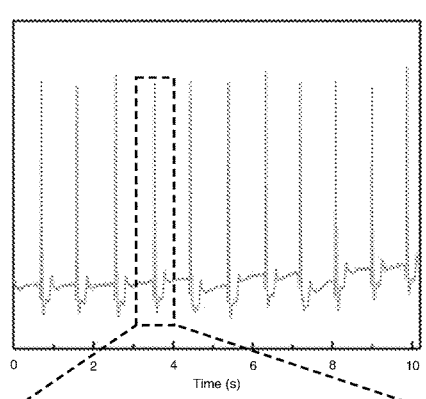

FIG. 39 is a flow diagram showing signal transmission through the multifunctional device. All the five sensing parts are connected with the Bluetooth for wireless data transmission. Analog sensing data are converted into digital signals with the built-in ADC from multi-protocol Bluetooth SOC (System on Chip). And then the data are transferred wirelessly with a 2.4 GHz antenna, oscillated by a 16 MHz external crystal. Both the sensing and wireless communication parts are powered by a 3 V battery.

FIG. 40 summaries the chips used in the illustrative multilayered stretchable system. In total, 56 components, in 31 different types, are used in the design. All thick active components, such as the amplifiers, Bluetooth, antenna, gyroscope, and accelerometer, are integrated in the $3^{rd}$ and $4^{th}$ layer with an offset method to avoid direct overlap of thick chips.

FIGS. 41A-41D shows ECG signals acquired from different positions of the human body. Images showing the device attached on (A) the chest and (B) the abdominal area. The power source for these measurements is omitted in the images for clarity purposes. Corresponding ECG signals acquired from (C) the chest and (D) the abdominal area, respectively.

FIG. 42 are optical images showing the positions where the EP signals are acquired: on the forearm for EMG, on the chest for ECG, on the side head for EOG, and on the forehead for EEG. The power source for these measurements is omitted in the images for clarity purposes.

FIGS. 43A-43C show EMG signals acquired from the forearm to show the signal frequency spectrum. (A) shows EMG time-domain signals with 60 Hz notch filter. (B) shows EMG signals from Fast Fourier Transform (FFT) analysis, showing the frequency distribution of the signals. The dip at around 60 Hz is from the notch filter. (C) shows the EMG power spectral density analyzed by Short-Time Fourier Transform (STFT), showing the time-domain EMG power distribution.

Figure 44A:
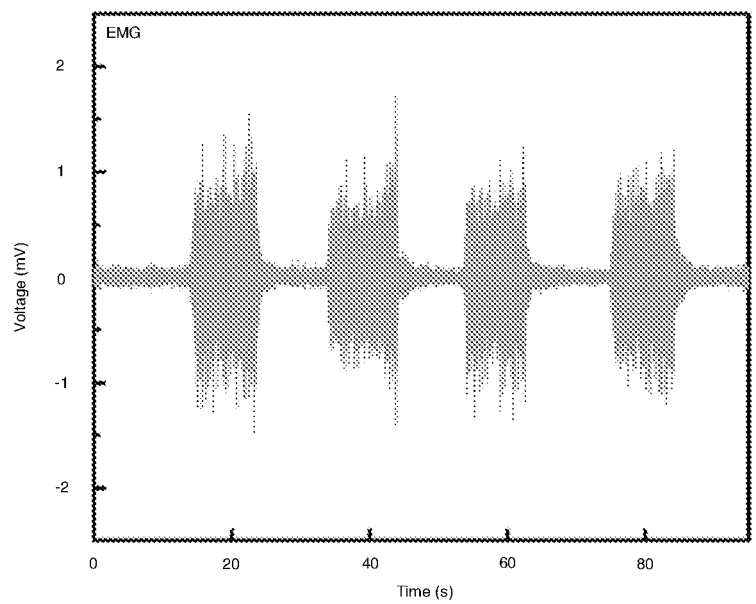
FIGS. 44A-44B show an EMG power analysis with root-mean-square envelope.
Figure 44B:
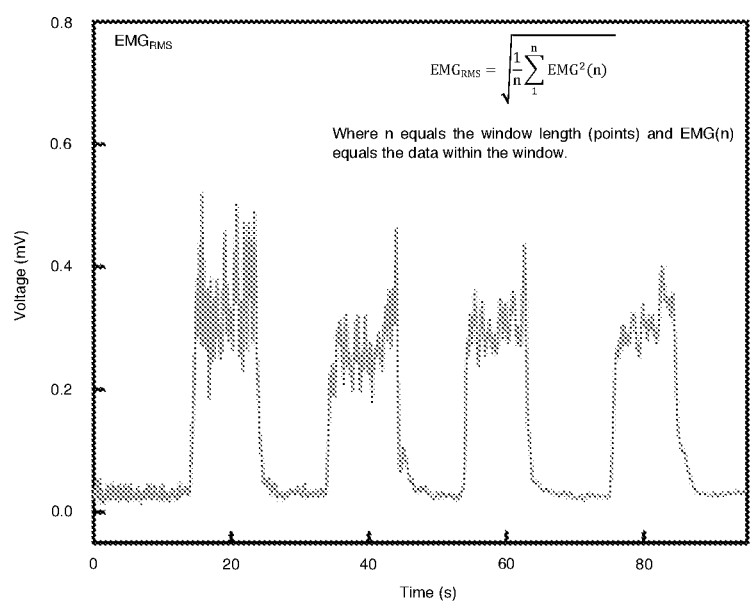

FIGS. 44A-44B show an EMG power analysis with root-mean-square envelope. (A) shows the raw data of EMG signals acquired from the forearm with periodic clinching. (B) shows an amplitude analysis with root-mean-square EMG envelope to quantify the signals.

Figure 45A:
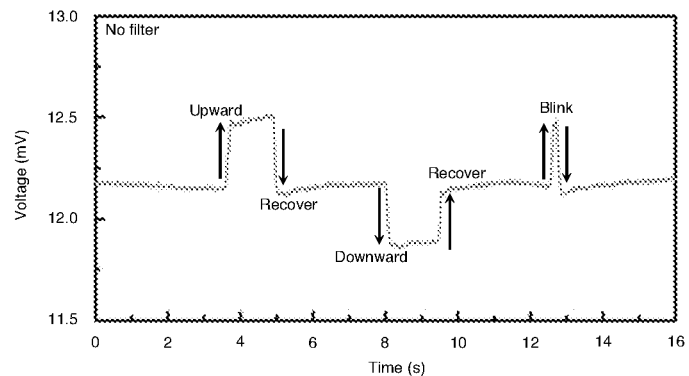
FIGS. 45A-45C show EOG signals processed with different filters.
Figure 45B:
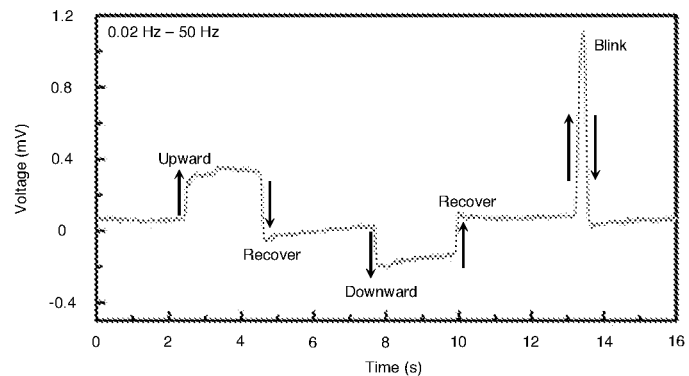
Figure 45C:
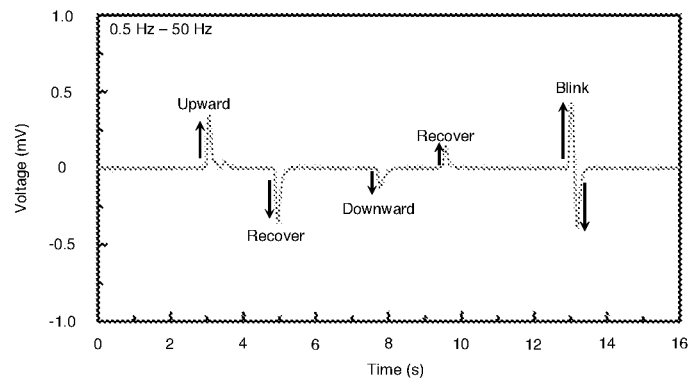

FIGS. 45A-45C show EOG signals processed with different filters. (A) shows EOG signals without a filter. There is a bias voltage of ~12.2 mV in the baseline, which is due to the charge accumulation between the two EP sensors. EOG signals with band-pass filters of (B) 0.02 Hz-50 Hz and (c) 0.5 Hz-50 Hz. The low frequency signal bias is removed. In (C) the EOG signals are also largely distorted from the original one. For our study, the filter of 0.02 Hz-50 Hz is chosen.

Figure 46:
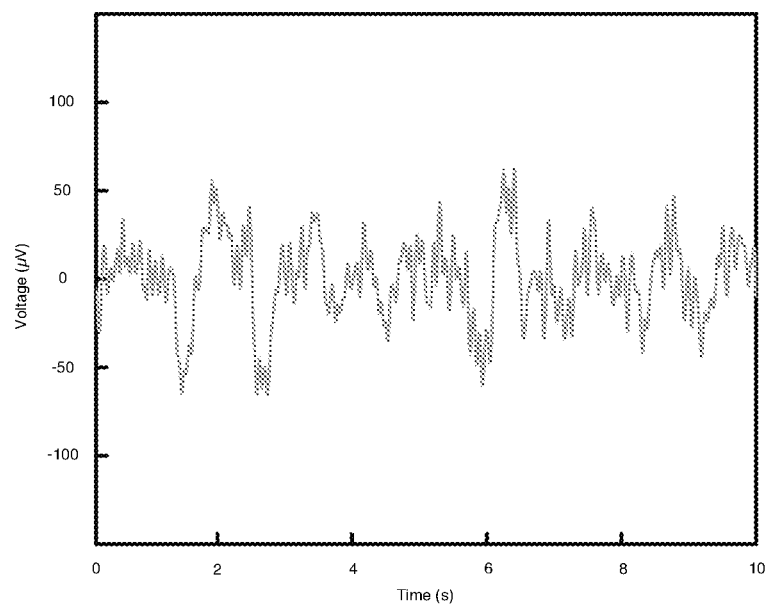
FIG. 46 shows EEG signals in the voltage-time domain.

FIG. 46 shows the EEG signals in the voltage-time domain. The signal noise level is 305 around 15 μV with a signal/noise ratio ~7 for this measurement.

FIGS. 47A-47C show a robotic arm controlling system. (A) is a work flow diagram of the controlling system. (B) shows that the device is powered by a lithium polymer battery connected by the anisotropic conductive film (ACF) cables. The battery is fixed on the arm by a wristband. (C) A picture showing the overall setup of the controlling system.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A method of fabricating a stretchable and flexible electronic device, comprising forming at least three functional layers, by, for each of the functional layers;
  forming a conductive interconnect pattern on an elastomer substrate, the conductive interconnect structure including islands interconnected by bridges;
  applying a conductive paste to the islands;
  positioning at least one functional electronic component on each of the islands;
  applying heat to cause the conductive paste to reflow;
  forming an elastomer encapsulant over the functional electronic components and the conductive interconnect pattern on each of the functional layers, the elastomer encapsulant having a Young's modulus equal to or less than a Young's modulus of the elastomer substrate, the elastomer encapsulant including a colored pigment that increases absorption of a selected laser wavelength by the elastomer encapsulant;
stacking the functional layers one over another;
laser ablating at least one via that provides electrical connection to any two layers in the three functional layers using laser light at the selected laser wavelength; and
filling the at least one via with solder paste and applying heat to cause the conductive paste to reflow, thereby establishing a bond and an electrical connection between the functional layers.

2. The method of claim 1 wherein forming the elastomer encapsulant includes spin coating the elastomer encapsulant over the functional electronic components and the conductive interconnect pattern on each of the functional layers.

3. The method of claim 1 further comprising defining the conductive interconnect pattern by laser ablating a predefined pattern in a bilayer that includes a metal layer and a polymide layer disposed on a substrate and transferring the conductive interconnect pattern to the functional layer using a water-soluble tape.

4. The method of claim 1 wherein filling the at least one via with solder paste includes dispensing solder paste into the at least one via by screen printing or dropping casting.

5. The method of claim 1 further comprising establishing an electrical connection between two of the functional layers by vertically arranging a zero-resistance jumper between the two functional layers.

6. The method of claim 1 wherein the bridges interconnecting the islands in the conductive interconnect pattern have a serpentine configuration.

7. The method of claim 1 wherein the functional electronic components are selected from the group consisting of sensors, active electronic components, and passive electronic components.

8. The method of claim 7 wherein the active electronic components are selected from the group consisting of amplifiers and RF components.

9. The method of claim 1 wherein the passive electronic components are selected from the group consisting of resistors, capacitors, and inductors.

10. The method of claim 1 wherein at least one of the functional electronic components includes a multichannel sensing system having a wireless communication circuit.

11. The method of claim 1 wherein at least one of the functional electronic components includes an accelerometer.

12. The method of claim 11 wherein at least another of the functional electronic components includes a gyroscope.

13. The method of claim 11 wherein at least another of the functional electronic components includes a strain sensor.

14. The method of claim 11 wherein at least another of the functional electronic components includes a temperature sensor.

15. The method of claim 11 wherein at least another of the functional electronic components includes a local field potential sensor.

16. A stretchable and flexible electronic device formed in accordance with the method of claim 1.

17. A stretchable and flexible electronic device, comprising
- at least three functional layers stacked one upon another, each of the functional layers including an elastomer substrate, a conductive interconnect pattern located on an elastomer substrate, the conductive interconnect structure including islands interconnected by bridges, at least one functional electronic component located on and in electrical communication with one of the islands;
- an elastomer encapsulant formed over the functional electronic components and the conductive interconnect pattern on each of the functional layers, the elastomer encapsulant having a Young's modulus equal to or less than a Young's modulus of the elastomer substrate, the elastomer encapsulant including a colored pigment that increases absorption of a selected laser wavelength by the elastomer encapsulant;
- at least one laser ablated via that provides electrical connection to any two layers in the three functional layers; and
- solder paste filling the laser ablated via, the solder paste establishing a bond and an electrical connection between the functional layers.

18. The stretchable and flexible electronic device of claim 17 wherein the functional electronic components are selected from the group consisting of sensors, active electronic components, and passive electronic components.

19. The stretchable and flexible electronic device of claim 18 wherein the active electronic components are selected from the group consisting of amplifiers and RF components.

20. The stretchable and flexible electronic device of claim 17 wherein at least one of the functional electronic components includes a multichannel sensing system having a wireless communication circuit.

* * * * *